US012582717B2

(12) United States Patent (10) Patent No.: US 12,582,717 B2
Vergauwen et al. (45) Date of Patent: Mar. 24, 2026

(54) PROTEIN BASED EXCIPIENT FOR ACTIVE PHARMACEUTICAL INGREDIENTS

(71) Applicant: ROUSSELOT B.V., Son (NL)

(72) Inventors: Bjorn Vergauwen, Lokeren (BE); Guy Van De Mooter, Pellenberg (BE)

(73) Assignee: Dispersome IP APS, Denmark (NL)

( * ) Notice: Subject to any disclaimer, the term of this patent is extended or adjusted under 35 U.S.C. 154(b) by 0 days.

(21) Appl. No.: 17/390,185

(22) Filed: Jul. 30, 2021

(65) Prior Publication Data

US 2022/0072136 A1 Mar. 10, 2022

Related U.S. Application Data

(62) Division of application No. 16/086,549, filed as application No. PCT/EP2017/060143 on Apr. 28, 2017, now abandoned.

(30) Foreign Application Priority Data

Apr. 29, 2016 (BE) ................................. 2016/5302
Dec. 26, 2016 (BE) ................................. 2016/5977

(51) Int. Cl.

| A61K 47/42 | (2017.01) |
|---|---|
| A61K 9/16 | (2006.01) |
| A61K 9/19 | (2006.01) |
| A61K 31/192 | (2006.01) |
| A61K 31/216 | (2006.01) |
| A61K 31/277 | (2006.01) |
| A61K 31/343 | (2006.01) |
| A61K 31/405 | (2006.01) |
| A61K 31/4166 | (2006.01) |
| A61K 31/4184 | (2006.01) |
| A61K 31/437 | (2006.01) |
| A61K 31/4422 | (2006.01) |
| A61K 31/495 | (2006.01) |
| A61K 31/496 | (2006.01) |
| A61K 31/55 | (2006.01) |
| A61K 31/5513 | (2006.01) |
| A61K 31/635 | (2006.01) |
| A61K 47/34 | (2017.01) |

(52) U.S. Cl.
CPC ............ *A61K 47/42* (2013.01); *A61K 9/1658* (2013.01); *A61K 9/19* (2013.01); *A61K 31/192* (2013.01); *A61K 31/216* (2013.01); *A61K 31/277* (2013.01); *A61K 31/343* (2013.01); *A61K 31/405* (2013.01); *A61K 31/4166* (2013.01); *A61K 31/4184* (2013.01); *A61K 31/437* (2013.01); *A61K 31/4422* (2013.01); *A61K 31/495* (2013.01); *A61K 31/496* (2013.01); *A61K 31/55* (2013.01); *A61K 31/5513* (2013.01); *A61K 31/635* (2013.01); *A61K 47/34* (2013.01)

(58) Field of Classification Search
None
See application file for complete search history.

(56) References Cited

U.S. PATENT DOCUMENTS

| 5,384,129 A | 1/1995 | Wunderlich et al. |
|---|---|---|
| 5,902,606 A | 5/1999 | Wunderlich et al. |
| 5,916,596 A | 6/1999 | Desai et al. |
| 9,066,870 B2 | 6/2015 | Hu et al. |
| 2003/0109639 A1 | 6/2003 | Lippold et al. |
| 2004/0175328 A1* | 9/2004 | Sutton .................. A61K 9/1688 |
| | | 424/491 |
| 2005/0031692 A1 | 2/2005 | Beyerinck et al. |
| 2007/0087022 A1* | 4/2007 | Desai ..................... A61K 9/107 |
| | | 514/449 |
| 2012/0225118 A1* | 9/2012 | Chen .................. A61K 31/5517 |
| | | 514/356 |
| 2014/0206717 A1 | 7/2014 | Higgins et al. |
| 2015/0265720 A1 | 9/2015 | Levine et al. |
| 2016/0073668 A1 | 3/2016 | Gilmer et al. |

FOREIGN PATENT DOCUMENTS

| CN | 1422618 A | 6/2003 |
|---|---|---|
| CN | 1515244 A | 7/2004 |
| CN | 102048695 A | 5/2011 |
| CN | 102327230 A | 1/2012 |
| CN | 103732216 A | 4/2014 |
| JP | H11-189548 A | 7/1999 |
| WO | WO 1998/014174 A1 | 4/1998 |
| WO | WO 2001/017504 A1 | 3/2001 |
| WO | WO 2001/062226 A2 | 8/2001 |
| WO | WO 2008/066899 A2 | 6/2008 |
| WO | WO 2009/063367 A1 | 5/2009 |
| WO | WO 2011/031462 A2 | 3/2011 |
| WO | WO 2016/041995 A1 | 3/2016 |

OTHER PUBLICATIONS

Shah et al. (Journal of Pharmacuetical Sciences, vol. 102, No. 3, Mar. 2013).*
Indian Journal of Pharmaceutical Sciences (Nov.-Dec. 1997 pp. 333-335).*
Carstensen, Advanced Pharmaceutical Solids, China Medical Science and Technology Press, p. 77, Oct. 31, 2004.
Chen, Pharmaceutics, Xi'an Jiaotong University Press, pp. 315-318, Jan. 31, 2014.
Imai et al., "Enhancement of Dissolution and Absorption of Mefenamic Acid by Egg Albumin", Journal of Pharmaceutical Sciences, May 1991, 80(5): 484-487.
International Preliminary Report on Patentability for International Patent Application No. PCT/EP2017/060143, mailed Jul. 13, 2018.

(Continued)

*Primary Examiner* — Bennett M Celsa
*Assistant Examiner* — Garen Gotfredson
(74) *Attorney, Agent, or Firm* — Judith Stone-Hulslander; James Velema; Lathrop GPM LLP

(57) ABSTRACT

Provided herein is a pharmaceutical formulation comprising a protein based excipient in combination with an active pharmaceutical ingredient (API) wherein said formulation is substantially amorphous and form a substantially homogenous mixture; and further a method for producing said pharmaceutical formulation; and said pharmaceutical formulation for use as a medicament.

20 Claims, 33 Drawing Sheets

(56) References Cited

OTHER PUBLICATIONS

International Search Report and Written Opinion for International Patent Application No. PCT/EP2017/060143, mailed Aug. 17, 2017.

Kaur et al., "Optimization of spray drying process for formulation of solid dispersion containing polypeptide-k powder through quality by design approach", Powder Technology, 2015, 284: 1-11.

Ki et al., "Characterization of gelatin nanofiber prepared from gelatin-formic acid solution", Polymer, 2005, 46(14): 5094-5102.

Pan et al., "Enhanced dispersibility and bioactivity of curcumin by encapsulation in Casein Nanocapsules", Journal of Agricultural and Food Chemistry, Jun. 4, 2013, pp. 6036-6043.

Tsuji et al., "Pharmacological and Pharmaceutical properties of freeze-dried formulations of egg albumin, indomethacin, olive oil, or fatty acids", Biol Pharm Bull., Jul. 1993, 16(7): 675-678.

Vialpando et al., "Evaluation of Three Amorphous Drug Delivery Technologies to Improve the Oral Absorption of Flubendazole", Journal of Pharmaceutical Sciences, 2016, 105(9): 2782-2793.

Wahlang et al., "Identification of permeability-related hurdles in oral delivery of curcumin using the Caco-2-cell model", European journal of Pharmceutics and Biopharmaceutics, Dec. 13, 2010, pp. 275-282.

U.S. Appl. No. 16/086,549 2019/0083629, filed Sep. 19, 2018 Mar. 21, 2019, Bjorn Vergauwen, Protein Based Excipient for Active Pharmaceutical Ingredients.

U.S. Appl. No. 17/390,185 2022/0072136, filed Jul. 30, 2021 Mar. 10, 2022, Bjorn Vergauwen, Protein Based Excipient for Active Pharmaceutical Ingredients.

Notice of Opposition against European Patent Application No. 17722708.9, dated Mar. 14, 2023, filed by Evonik Operations GmbH.

Bhende et al., "Moringa Coagulant as a Stabilizer for Amorphous Solids: Part I", AAPS PharmSciTech, Jun. 2012, 13(2): 400-410. (D1 Cited in Notice of Opposition against European Patent Application No. 17722708.9, dated Mar. 14, 2023, filed by Evonik Operations GmbH.).

European Pharmcopoeia 11—Ibuprofen, Jan. 2017. (D6c Cited in Notice of Opposition against European Patent Application No. 17722708.9, dated Mar. 14, 2023, filed by Evonik Operations GmbH.).

European Pharmcopoeia 11—Indomacetin, Apr. 2019. (D6d Cited in Notice of Opposition against European Patent Application No. 17722708.9, dated Mar. 14, 2023, filed by Evonik Operations GmbH.).

Hui et al., "Preparation and characterization of itraconazole albumin nanosuspension", Journal of China Pharmaceutical University, 2008, 39(6): 510-514, including English translation. (D4 and D4a Cited in Notice of Opposition against European Patent Application No. 17722708.9, dated Mar. 14, 2023, filed by Evonik Operations GmbH.).

Summary of experimental data for examples 1, 2 and 8 of JPH 11-189548 A (Jul. 13, 1999.) (D6b Cited in Notice of Opposition against European Patent Application No. 17722708.9, dated Mar. 14, 2023, filed by Evonik Operations GmbH.).

Suzuki et al., "Application of Solid Dispersion to Enhance Dissolution Properties of Mefenamic Acid with Casein", Japanese Journal of Hospital Pharmacy, Oct. 1991, 17(5): 298-305, including English translation. (D2 and D2a Cited in Notice of Opposition against European Patent Application No. 17722708.9, dated Mar. 14, 2023, filed by Evonik Operations GmbH.).

Baek et al., "Design of a gelatin microparticle-containing self-microemulsifying formulation for enhanced oral bioavailability of dutasteride", Drug Design, Development, and Therapy, 2015, 9: 3231-3238. (D10 Cited in Notice of Opposition against European Patent Application No. 17722708.9, dated Mar. 14, 2023, filed by Evonik Operations GmbH.).

Federal Register, Wednesday, Dec. 24, 1997, vol. 62, No. 247, pp. 67377-67388. (D11 Cited in Notice of Opposition against European Patent Application No. 17722708.9, dated Mar. 14, 2023, filed by Evonik Operations GmbH.).

Notice of Opposition against European Patent Application No. 17722708.9, dated Mar. 14, 2023, filed by GELITA AG.

Jachowicz et al., "Enhanced release of oxazepam from tablets containing solid dispersions", International Journal of Pharmaceutics, 1997, 159: 149-158. (D7 Cited in Notice of Opposition against European Patent Application No. 17722708.9, dated Mar. 14, 2023, filed by Gelita Ag.).

Paudel et al., "Manufacturing of solid dispersions of poorly water soluble drugs by spray drying: Formulation and process considerations", International Journal of Pharmaceutics, Aug. 2013, 453(1): 253-284. (D8 Cited in Notice of Opposition against European Patent Application No. 17722708.9, dated Mar. 14, 2023, filed by GELITA AG.).

Ceballos et al., "Exploring flubendazole formulations for use in sheep. Pharmacokinetic evaluation of a cyclodextrin-based solution", BMC Veterinary Research, May 28, 2012, 8(71): 1-10.

Lin et al., "Stability of Human Serum Albumin During Bioprocessing: Denaturation and Aggregation During Processing of Albumin Paste," Pharm Res., 2000, 17: 391-396.

Mishra et al. "Whey proteins as stabilizers in amorphous solid dispersion", European Journal of Pharmaceutical Sciences, 2019, 128: 144-151.

* cited by examiner

PROTEIN BASED EXCIPIENT FOR ACTIVE PHARMACEUTICAL INGREDIENTS

RELATED APPLICATIONS

This application is a division of U.S. patent application Ser. No. 16/086,549, filed Sep. 19, 2018, which is a 35 U.S.C. § 371 filing of International Patent Application No. PCT/EP2017/060143, filed Apr. 28, 2017, which claims the benefit of priority to Belgian Patent Application Nos. 2016/5302, filed Apr. 29, 2016, and 2016/5977, filed Dec. 26, 2016. The entire contents of these applications are incorporated herein by reference for all purposes.

FIELD OF THE INVENTION

Provided herein is a pharmaceutical formulation comprising a protein based excipient in combination with an active pharmaceutical ingredient (API) wherein said formulation is substantially amorphous and form a substantially homogenous mixture; and further a method for producing said pharmaceutical formulation; and said pharmaceutical formulation for use as a medicament.

BACKGROUND

In order to perform to their full potential, an 'active pharmaceutical ingredient' (API) must surmount a number of obstacles to reach its (biological) target. Poor solubility and long dissolution rates (i.e., disintegration times) can impede the delivery speed of an API. An especially poorly soluble API may have its bioavailability (i.e., the administered dose of the unchanged API that reaches the systemic circulation) severely diminished.

Due to their chemical properties most API candidates are subjected to dissolution problems during drug development. In some cases these solubility problems are resolved in the research centers and the API candidates may become the active ingredient of a medicament. However, for a large group of difficult-to-formulate API candidates the low absorption rates when administered orally are so extensive that the API candidates eventually require alternative intake means, or in a worst case scenario be prevented from altogether reaching the commercial market. It is estimated that almost 60-70% of API currently in development are poorly soluble in water, with almost 40% being practically insoluble.

The commonly preferred dosage form for an API is a solid dosage form, such as a tablet or a capsule. Usually, the solid dosage form not only contains the API, which is the drug itself, but at least one ingredient other than the API. Traditionally, said additional ingredient is pharmaceutically inert and does not react biologically with the API itself, aside from stabilizing the formulation. These inactive ingredients are commonly referred to as excipients in pharmaceutical contexts. Thus in contrast to the API, which is chosen primarily for its active properties, the excipient is chosen primarily for its non-active properties.

Currently various designer polymers (e.g. Polymethylmethacrylate-sorbitol) are developed to fulfill the role of an excipient and create a soluble formulation. For example, polymers used in amorphous solid dispersions were shown to exhibit solubility enhancing properties. However, the applicability of polymers in the pharmaceutical industry has also created new challenges associated with their development, processing and manufactory.

Polymers have the distinct disadvantage of not originating from a biologically relevant source. Considering that many of the intermolecular interactions and complexations (e.g. H-bonding, ionic, and/or van der Waal's interactions) of hydrophilic polymers with the API are adjusted to balance the solubility and stability of the formulation, it becomes often unpredictable whether or not the presence of polymers may have additional, undesired effects on the medicament, or alternatively, may lack or lose certain desired interactions. More so the costs of developing, testing and subsequently producing said designer polymer excipients may even surpass the productions costs of the API itself, especially so for off-the shelf pharmaceuticals.

Also, certain APIs have their active properties diminished or altogether lost due to the physical conditions (e.g. temperature, humidity, flow, etc.) present in the development and/or manufacturing stage of the formulation. Exposure to excessive temperature and humidity causes structural degradation and chemical behavior changes in an API. For example, certain APIs have shown to be incompatible with hot melt extrusion, a common polymer production method.

Moreover, certain APIs also display a chemical interaction with residual solvents commonly applied for polymer processing, or in certain cases the APIs may even react with the polymer itself when joined together; in particular for C—O, C—N, and double bonds. For example, at C-O bonds oxidation, reduction, cleavage, addition and elimination can readily occur. All these situations lead to impurities in the API formulation which have no therapeutic value and are even potentially harmful (i.e. genotoxic). For example, the application of alcohols like methanol or ethanol, which are common solvents used during polymer manufactory, will cause certain API to form sulphonate esters exhibiting genotoxic properties.

The solubility and the dissolution level of the API used in the formulation directly affect the bioavailability and supersaturation state. Therefore, it is very important to increase the solubility and the dissolution levels of the API, especially for API exhibiting a low solubility and/or bioavailability. Achieving a state of supersaturation, and subsequently maintaining said supersaturation state for as long as possible, results in even more favorable results of the API. Additionally, an improvement in bioavailability and maintained supersaturation will increase the absorption speed of the API, which may result in a lowered total weight/volume (dosage) required of the API in a formulation.

Accordingly, a need arises to obtain an effective and stable excipient that can be combined in a formulation to enhance the solubility and dissolution level for an API. Additionally, said excipient preferably also enhances the bioavailability of said APIs, and further enables and maintains a state of supersaturation. Concretely, there is a need for such an excipient for APIs exhibiting a low solubility and dissolution rate and/or levels. State of art excipients do not reach the combined safety and bio relevance/interaction, improved supersaturation and bioavailability, and processing scale, costs and times in a way achieved by the present invention.

SUMMARY OF THE INVENTION

The present invention relates to an excipient as described herein, a method of producing said excipient, and by extension, a formulation comprising said excipient in combination with an API.

While many APIs are known in the art, several classes of APIs can be distinguished based on their solubility and/or bioavailability. APIs exhibiting low solubility and/or bio-availability have been described in the art and are known to the skilled person. In a particular embodiment of the present invention, the (protein-based) excipient according to the present invention is combined with an API. In particular, said API is an API which exhibits a poor solubility and/or bioavailability, thereby benefiting from the solubility and bioavailability enhancing properties of the excipient according to the present invention. In particular embodiments, said API is selected from Flubendazole, Carbamazepine, Griseofulvin, Phenytoin, Nifedipine, Verapamil, Azithromycin, Nitrofurantoin, Iopanoic acid, Itraconazole, Ibuprofen, Indomethacin, Glibenclamide, Bicalutamide, Ezetimibe, Aceclofenac, Ketoconazole, Oxfendazole, Ritonavir, Saquinavir, Fenofibrate, Cinnarizin, Darunavir, Diazepam, Bifonazole, Testosterone undecanoate, or Naproxen; preferably Flubendazole, Ibuprofen, Indomethacin, Ritonavir, Naproxen, Phenytoin, Nifedipine, Vemurafenib, Griseofulvin, Itraconazole, or Verapamil; most preferably Flubendazole.

Accordingly, the present invention relates to a formulation comprising:

a protein based excipient obtained from a protein composition or a hydrolysate thereof which comprises proteins—as per monomer—of at least 10 amino acids in length; and
  an active pharmaceutical ingredient (API);
  characterized therein that said protein based excipient and said API are both substantially amorphous and form a substantially homogenous mixture.

In particular, the formulation as disclosed herein provides that said protein based excipient and said API are both completely amorphous and/or form a completely homogenous mixture.

In particular, the formulation as disclosed herein provides that said protein based excipient and said API form an amorphous solid dispersion.

In particular, the formulation as disclosed herein provides that the protein based excipient is substantially not denaturized, preferably completely not denaturized; and/or retains at least part of its biological activity, preferably substantially retains its biological activity; more preferably retains almost completely its biological activity, most preferably retains completely its biological activity.

In particular, the formulation as disclosed herein provides that the protein based excipient is obtained from a protein composition or a hydrolysate thereof which comprises proteins—as per monomer—of at least 20 amino acids in length; preferably at least 50 amino acids in length; more preferably at least 100 amino acids in length; most preferably at least 250 amino acids in length, for example 500 amino acids or 700 amino acids.

In particular, the formulation as disclosed herein provides that at least one protein of the protein composition or a hydrolysate thereof is chosen from soy protein, pea protein, blood proteins, Immunoglobulins, milk proteins, gelatine, keratin, corn, wheat, hemp, rye, oats, peanut, barley, casein, albumin, whey protein (lactalbumin), Hydrolysed Whey Protein Isolate (HWPI), hydrolyzed collagen, plasma proteins, serum albumin, bovine serum albumin (BSA), human serum albumin (HSA), egg albumin, fish albumin, elastin, collagen, recombinant or artificial proteins, recombinant versions of natural or artificial binding scaffolds, or a combination thereof; preferably HSA, BSA, gelatine and/or a combination thereof.

In particular, the formulation as disclosed herein provides that the API exhibits a low solubility, dissolution level, supersaturation state and/or bioavailability.

In particular, the formulation as disclosed herein provides that the API is classified as poorly or not soluble, poorly or not permeable, and/or slowly dissolving according to the biopharmaceutics classification system.

In particular, the formulation as disclosed herein provides that the API is a class II, class III or a class IV API; preferably a class II or a class IV API; most preferably a class II API according to the biopharmaceutics classification system.

In particular, the formulation as disclosed herein provides that the API is selected from the following list: Flubendazole, Carbamazepine, Griseofulvin, Phenytoin, Nifedipine, Verapamil, Azithromycin, Nitrofurantoin, Iopanoic acid, Itraconazole, Ibuprofen, Indomethacin, Glibenclamide, Bicalutamide, Ezetimibe, Aceclofenac, Ketoconazole, Oxfendazole, Ritonavir, Saquinavir, Fenofibrate, Cinnarizin, Darunavir, Diazepam, Bifonazole, Testosterone undecanoate, or Naproxen; more in particular from the following list: Flubendazole, Ibuprofen, Indomethacin, Ritonavir, Naproxen, Phenytoin, Nifedipine, Vemurafenib, Griseofulvin, Itraconazole, or Verapamil.

In particular, the formulation as disclosed herein provides that said API is Flubendazole and wherein said protein based excipient obtained from a protein composition or a hydrolysate thereof which comprises serum albumin (HSA, BSA) and/or gelatin.

In particular, the formulation as disclosed herein provides that said formulation is characterized by having a particle size between 1 μm and 1 mm; preferably between 5 μm and 50 μm; most preferably between 10 μm and 20 μm.

In particular, the formulation as disclosed herein provides that the mass ratio (w/w) of API to excipient is between at least 5% API and at most 95% excipient, to at least 95% API and at most 5% excipient; wherein 100% is defined as the total mass of the API and excipient.

In particular, the formulation as disclosed herein provides that the formulation comprises a mass ratio (w/w) of API to excipient (w/w) between at least 5% API and at most 95% excipient, to at most 60% API and at least 40% excipient; wherein 100% is defined as the total mass of the API and excipient. 15. The formulation according to any of the preceding claims 1 to 14, wherein said formulation is dosed in a solid-dosage form, preferably a tablet, pill or capsule, or as components for reconstituting an injectable.

In particular, the formulation as disclosed herein provides that it is provided in a solid-dosage form, preferably in a form adapted for oral administration such as a tablet, lozenge, pill or capsule, or as components for reconstituting an injectable.

In particular, the formulation as disclosed herein provides that the solid-dosage form is a unit-dose that contains a predetermined amount of API sufficient for one regular application or use of said API, and wherein the unit-dose is suitable for unit-dose packaging, such as blisters packs.

According to a further aspect, the present invention relates to a method for producing a pharmaceutical formulation comprising:

a protein based excipient obtained from a protein composition or a hydrolysate thereof which comprises proteins—as per monomer—of at least 10 amino acids in length; and
  an active pharmaceutical ingredient (API);

5 characterized therein that said protein based excipient and said API are both substantially amorphous and form a substantially homogenous mixture;

said method comprising at least the steps of:

(a) dissolving said API using a solvent to obtain a solution; and, (b) drying the solution of step (a) to obtain a powder that is substantially amorphous.

In particular, the method as disclosed herein provides that said protein based excipient and said API are both completely amorphous and the drying of step (b) drying is performed to obtain a powder that is completely amorphous.

In particular, the method as disclosed herein provides that said protein based excipient and said API form a completely homogenous mixture.

In particular, the method as disclosed herein provides that said protein based excipient and said API form an amorphous solid dispersion.

In particular, excipient is prepared through the steps of:

(i) dissolving an protein composition or hydrolysate thereof using a solvent to obtain a solution; and (ii) drying the solution of step (i) to obtain said protein based excipient.

In particular, wherein the solutions of steps (a) and (i) are dissolved using a common or different solvent.

In particular, the method as disclosed herein provides that the API and protein based excipient are either:

dissolved and dried together in the same solvent, thereby forming said pharmaceutical formulation;

dissolved separately in the same or a different solvent and subsequently dried together, thereby forming said pharmaceutical formulation;

dissolved in the same or a different solvent and dried separately and subsequently mixed, thereby forming said pharmaceutical formulation.

In particular, the method as disclosed herein provides that the solvent is an organic acid, preferably formic acid, trifluoroacetic acid, or acetic acid, a mixture of said acids, or a mixture comprising one or more organic acids, preferably formic acid, and/or trifluoroacetic acid, and/or acetic acid, and commonly used pharmaceutical solvents, such as methanol, ethanol, acetone, DCM, THF, methylene chloride, methyl ethyl ketone, acetonitrile, organosulfur compound, DMSO, polyethylene glycols.

In particular, the method as disclosed herein provides that the solvent is a solvent mixture comprising at least 5% of acetic acid and/or formic acid to at most 90% acetic acid and/or formic acid (v/v); preferably 10% to 90% acetic acid and/or formic acid; more preferably 15% to 90% acetic acid and/or formic acid; most preferably 20% to 90% acetic acid and/or formic acid.

In particular, the method as disclosed herein provides that the solvent is a binary solvent mixture comprising one organic acid, preferably chosen from acetic acid or formic acid, and one other (traditional) solvent, preferably chosen from alcohol, acetone, DCM, THF, methylene chloride, methyl ethyl ketone, acetonitrile, or polyethylene glycols.

In particular, the method as disclosed herein provides that the solvent is a ternary solvent mixture, comprising at least one organic acid, preferably chosen from acetic acid and/or formic acid, more preferably are acetic acid or formic acid, and at least one other (traditional) solvents, preferably chosen from alcohol, acetone, DCM, THF, methylene chloride, methyl ethyl ketone, acetonitrile, and/or polyethylene glycols.

In particular, the method as disclosed herein provides that the solvent is a solvent mixture comprising dimethyl sulfoxide (DMSO) in an amount of at least 5% to at most 90% (v/v); preferably 10% to 90% DMSO; preferably 10% to 90% DMSO; more preferably 15% to 90% DMSO; most preferably 20% to 90% DMSO.

In particular, the method as disclosed herein provides that the solvent is a binary solvent mixture comprising one organosulfur compound, preferably DMSO, and one other (traditional) solvent, preferably chosen from alcohol, acetone, DCM, THF, methylene chloride, methyl ethyl ketone, acetonitrile, DMSO, or polyethylene glycols.

In particular, the method as disclosed herein provides that the solvent is a ternary solvent mixture comprising at least one organosulfur compound, preferably DMSO, and at least one other (traditional) solvent, preferably chosen from alcohol, acetone, DCM, THF, methylene chloride, methyl ethyl ketone, acetonitrile, DMSO, or polyethylene glycols.

In particular, the method as disclosed herein provides that the solvent is a quaternary solvent mixture, comprising at least one organic acid, preferably chosen from acetic acid and/or formic acid, preferably are acetic acid and formic acid, and at least one other (traditional) solvents, preferably chosen from alcohol, acetone, DCM, THF, methylene chloride, methyl ethyl ketone, acetonitrile, DMSO, and/or polyethylene glycols.

In particular, the method as disclosed herein provides that the solvent is a quaternary solvent mixture, comprising at least one organosulfur compound, preferably DMSO, and at least one other (traditional) solvent, preferably chosen from alcohol, acetone, DCM, THF, methylene chloride, methyl ethyl ketone, acetonitrile, DMSO, and/or polyethylene glycols.

In particular, the method as disclosed herein provides that the drying is performed by spray drying, freeze drying, vacuum drying, flash drying, paddle drying, air drying, condensation drying, and/or a combination thereof; preferably by spray drying and/or freeze drying.

In particular, the method as disclosed herein provides that the solvent comprises an organic acid, preferably acetic acid and/or formic acid, and the drying is spray drying.

In particular, the method as disclosed herein provides that the solvent comprises an organosulfur compound, preferably DMSO, and the drying is freeze drying.

In particular, the method as disclosed herein provides that the drying process is followed by a solid dosage forming process, such as compression or molding.

In particular, the method as disclosed herein provides that the method is freeze drying and the formulation is freeze dried directly into a solid dosage form; for example freeze dried directly into blisters to produce a tablet or pill.

In particular, the method as disclosed herein provides that the protein based excipient is obtained from a protein composition or a hydrolysate thereof which comprises proteins—as per monomer—of at least 10 amino acids in length; preferably at least 20 amino acids in length; preferably at least 50 amino acids in length; more preferably at least 100 amino acids in length; most preferably at least 250 amino acids in length, for example 500 amino acids or 700 amino acids.

In particular, the method as disclosed herein provides that the API is classified as poorly or not soluble, poorly or not permeable, and/or slowly dissolving according to the biopharmaceutics classification system.

In particular, the method as disclosed herein provides that the API is a class II, class III or a class IV API; preferably a class II or a class IV API; most preferably a class II API according to the biopharmaceutics classification system.

In particular, the method as disclosed herein provides that the API is selected from the following list: Flubendazole, Carbamazepine, Griseofulvin, Phenytoin, Nifedipine, Verapamil, Azithromycin, Nitrofurantoin, Iopanoic acid, Itraconazole, Ibuprofen, Indomethacin, Glibenclamide, Bicalutamide, Ezetimibe, Aceclofenac, Ketoconazole, Oxfendazole, Ritonavir, Saquinavir, Fenofibrate, Cinnarizin, Darunavir, Diazepam, Bifonazole, Testosterone undecanoate, or Naproxen; more in particular from the following list: Flubendazole, Ibuprofen, Indomethacin, Ritonavir, Naproxen, Phenytoin, Nifedipine, Vemurafenib, Griseofulvin, Itraconazole, or Verapamil.

According to a further aspect, the present invention relates a use of a protein composition or a hydrolysate thereof comprising proteins—as per monomer—of at least 10 amino acids in length as a protein based excipient in a formulation according to an embodiment as disclosed herein.

In particular, the method as disclosed herein provides that the protein based excipient is substantially not denaturized, preferably completely not denaturized; and/or retains at least part of its biological activity, preferably substantially retains its biological activity; more preferably retains almost completely its biological activity, most preferably retains completely its biological activity.

In particular, the method as disclosed herein provides that the protein based excipient is obtained from a protein composition or a hydrolysate thereof which comprises proteins—as per monomer—of at least 10 amino acids in length; preferably at least 20 amino acids in length; preferably at least 50 amino acids in length; more preferably at least 100 amino acids in length; most preferably at least 250 amino acids in length, for example 500 amino acids or 700 amino acids.

In particular, the method as disclosed herein provides that at least one protein of the protein composition or a hydrolysate thereof is chosen from soy protein, pea protein, blood proteins, Immunoglobulins, milk proteins, gelatine, keratin, corn, wheat, hemp, rye, oats, peanut, barley, casein, albumin, whey protein (lactalbumin), Hydrolysed Whey Protein Isolate (HWPI), hydrolyzed collagen, plasma proteins, serum albumin, bovine serum albumin (BSA), human serum albumin (HSA), egg albumin, fish albumin, elastin, collagen, recombinant or artificial proteins, recombinant versions of natural or artificial binding scaffolds, and/or a combination thereof; preferably HSA, BSA, gelatine and/or a combination thereof.

According to a further aspect, the present invention relates to a formulation according to an embodiment as disclosed herein for use as a medicament.

70% gelatin: 20% FLU; (4) 80% gelatin: 20% FLU (4). The upper line is an XRD pattern of Flubendazole powder and serves as reference. The results can be found discussed further in Example 8.

Figure 10:
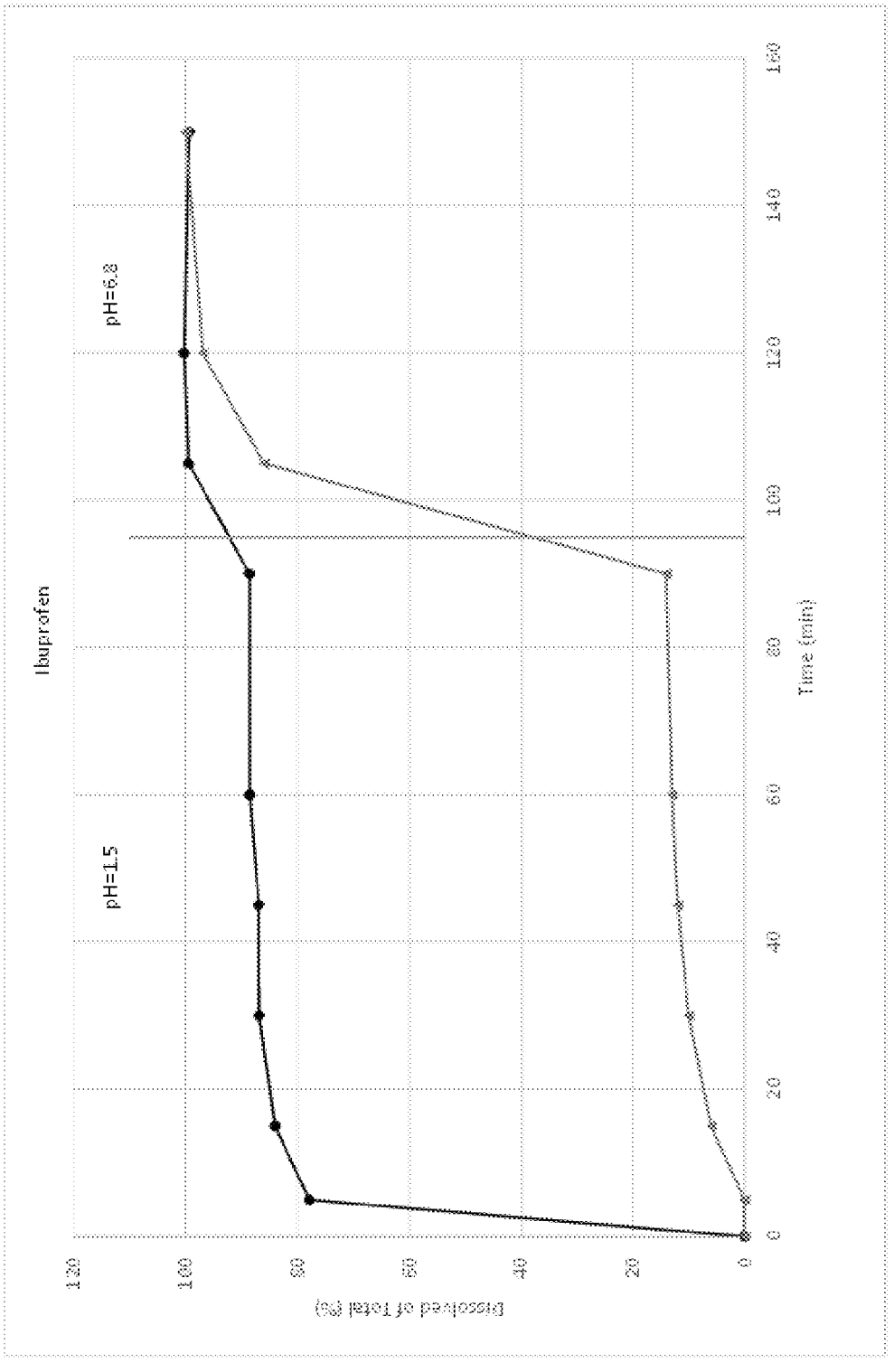

FIG. 10: Graph of a dissolution profile displaying the average dissolution (%) of a (spray dried) formulation comprising 20% Ibuprofen and 80% BSA (w/w) in function of the dissolution time (min). The results can be found discussed further in Example 9 and the legend is as follows: circle—as film; triangle—as powder.

Figure 11:
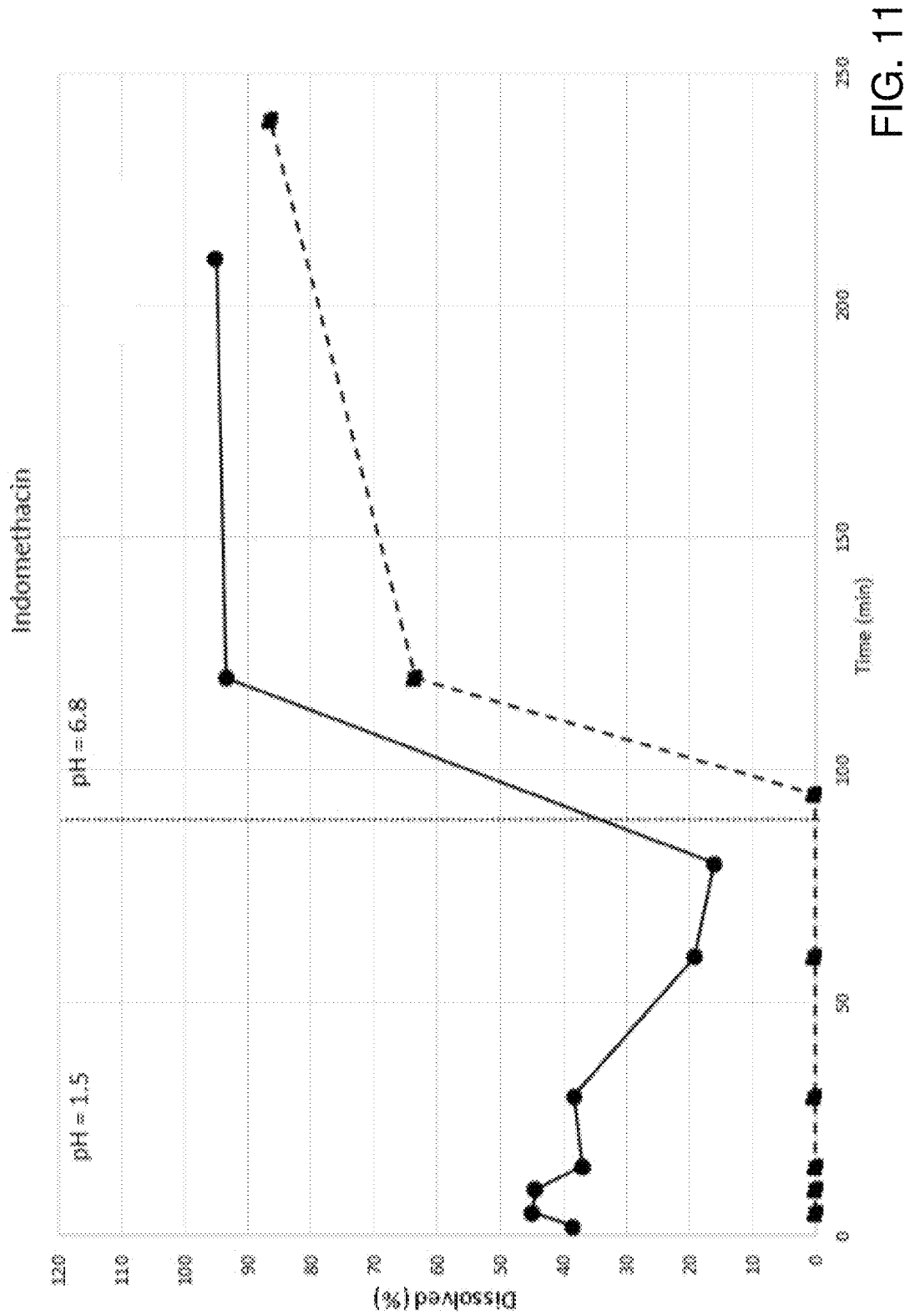

FIG. 11: Graph of a dissolution profile displaying the average dissolution (%) of a (spray dried) formulation comprising 20% Indomethacin and 80% BSA (w/w) in function of the dissolution time (min). The results can be found discussed further in Example 9 and the legend is as follows: circle with full line—as film; triangle with dotted line—as powder.

Figure 12:
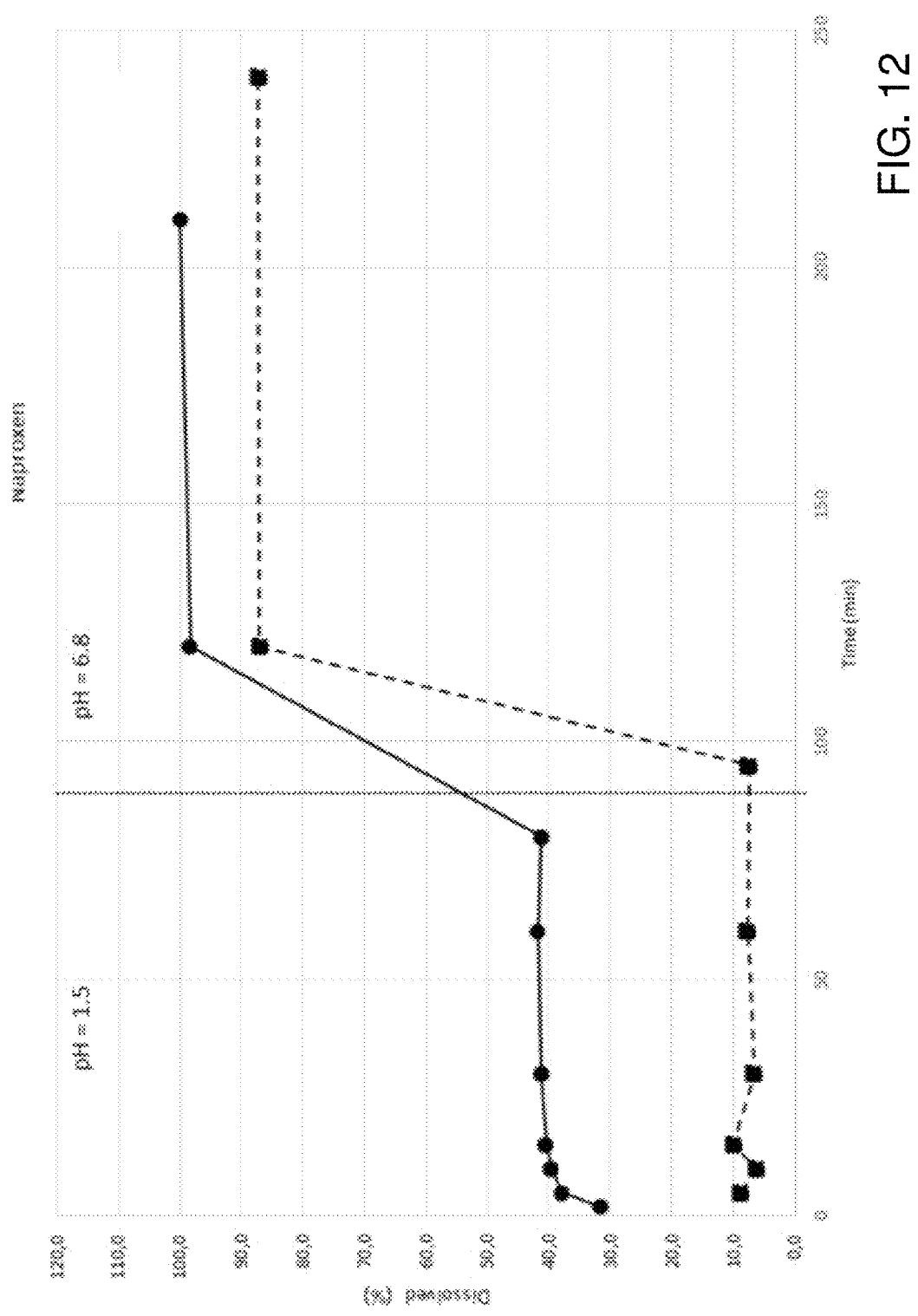

FIG. 12: Graph of a dissolution profile displaying the average dissolution (%) of a (spray dried) formulation comprising 20% Naproxen and 80% BSA (w/w) in function of the dissolution time (min). The results can be found discussed further in Example 9 and the legend is as follows: circle with full line—as film; triangle with dotted line—as powder.

Figure 13:
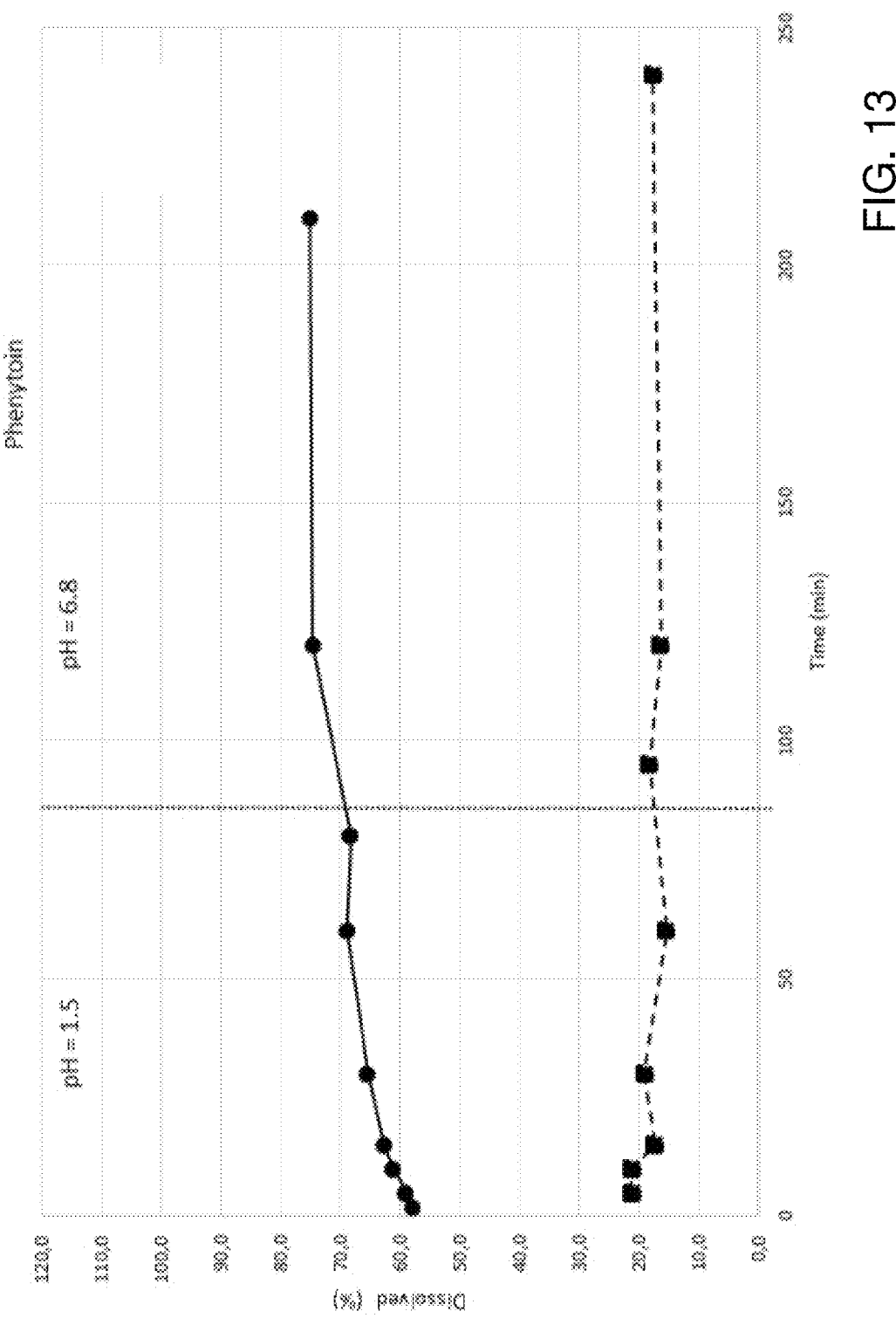

FIG. 13: Graph of a dissolution profile displaying the average dissolution (%) of a (spray dried) formulation comprising 20% Phenytoin and 80% BSA (w/w) in function of the dissolution time (min). The results can be found discussed further in Example 9 and the legend is as follows: circle with full line—as film; triangle with dotted line—as powder.

Figure 14:
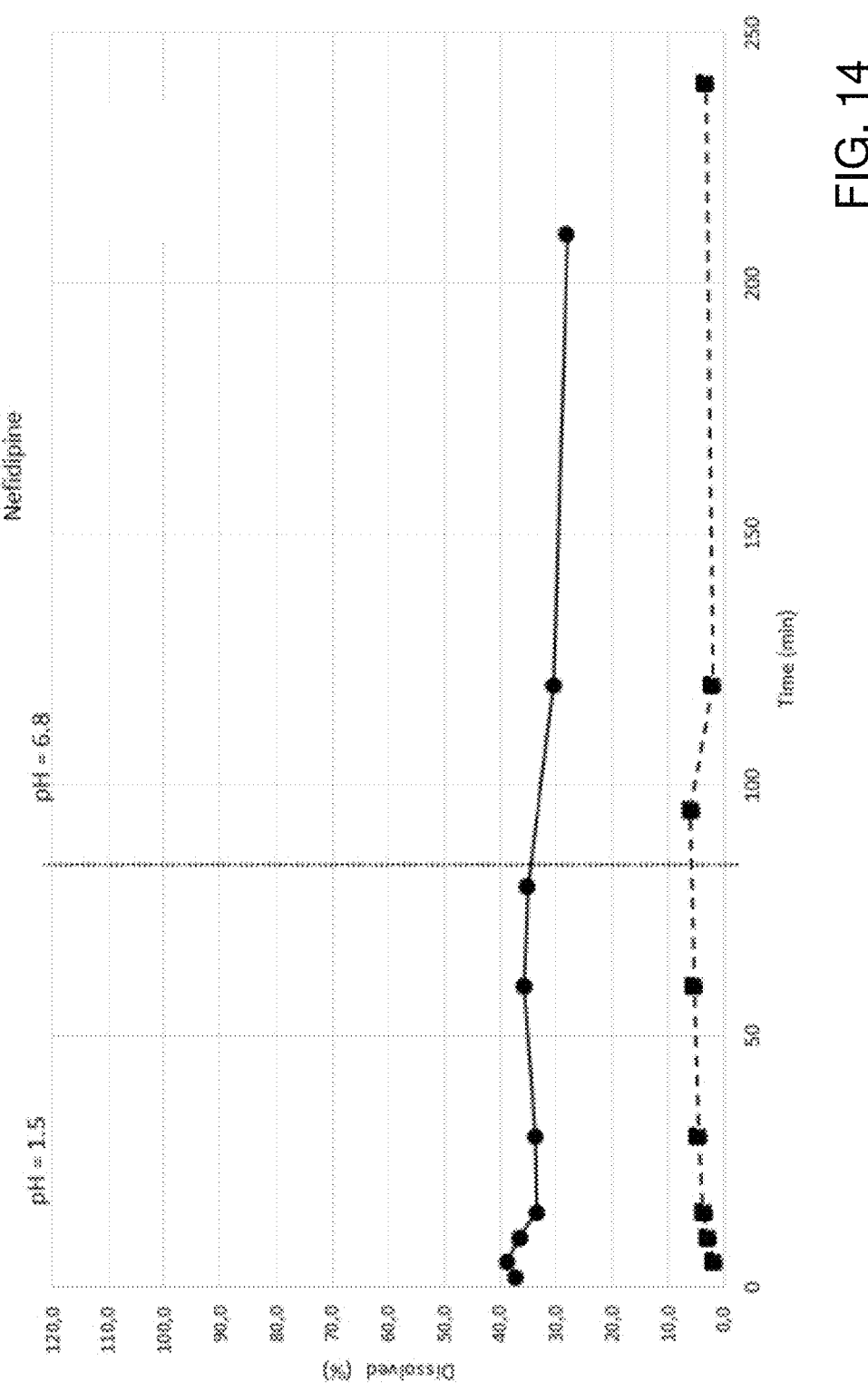

FIG. 14: Graph of a dissolution profile displaying the average dissolution (%) of a (spray dried) formulation comprising 20% Nifedipine and 80% BSA (w/w) in function of the dissolution time (min). The results can be found discussed further in Example 9 and the legend is as follows: circle with full line—as film; triangle with dotted line—as powder.

Figure 15:
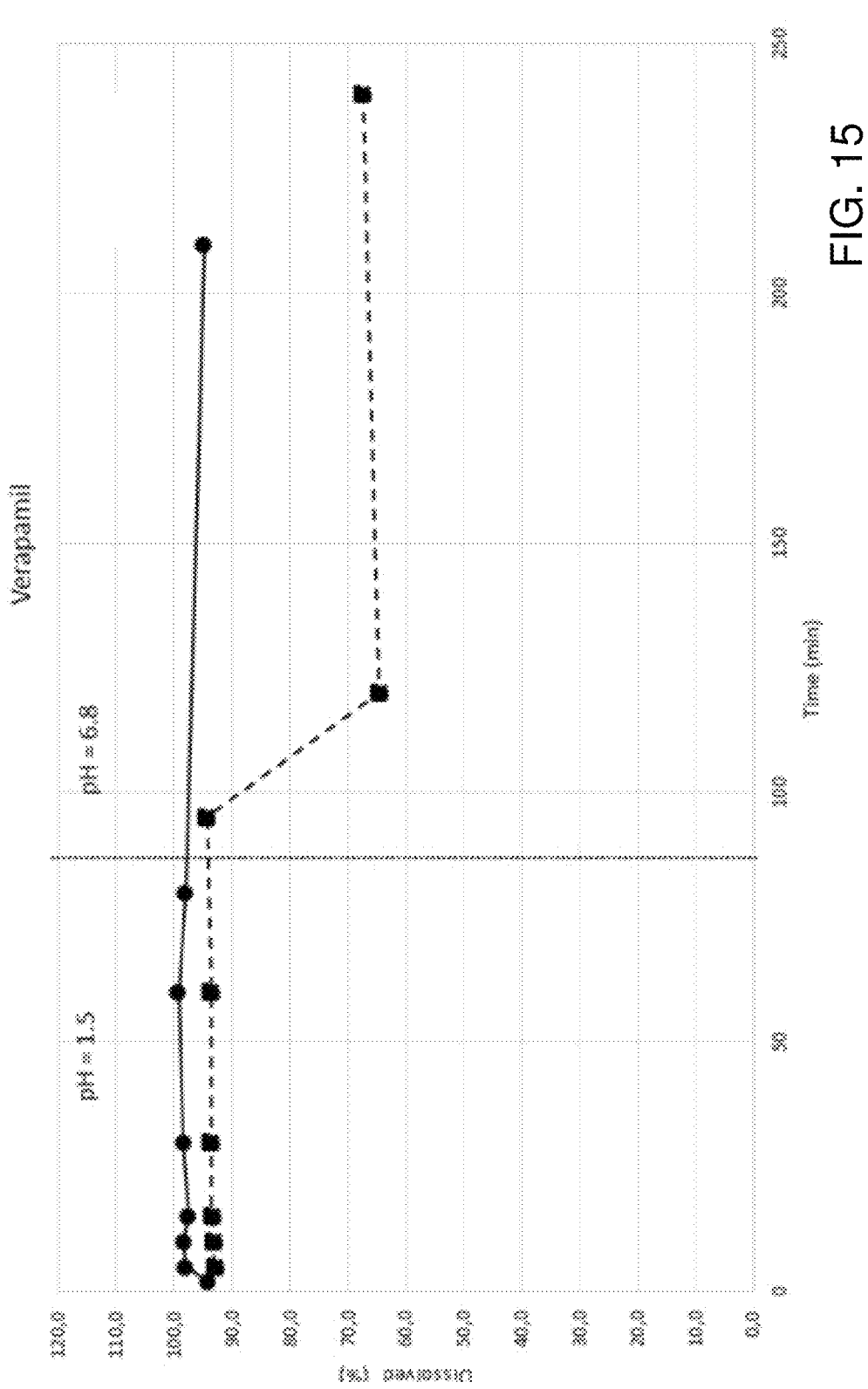

FIG. 15: Graph of a dissolution profile displaying the average dissolution (%) of a (spray dried) formulation comprising 20% Verapamil and 80% BSA (w/w) in function of the dissolution time (min). The results can be found discussed further in Example 9 and the legend is as follows: circle with full line—as film; triangle with dotted line—as powder.

Figure 16:
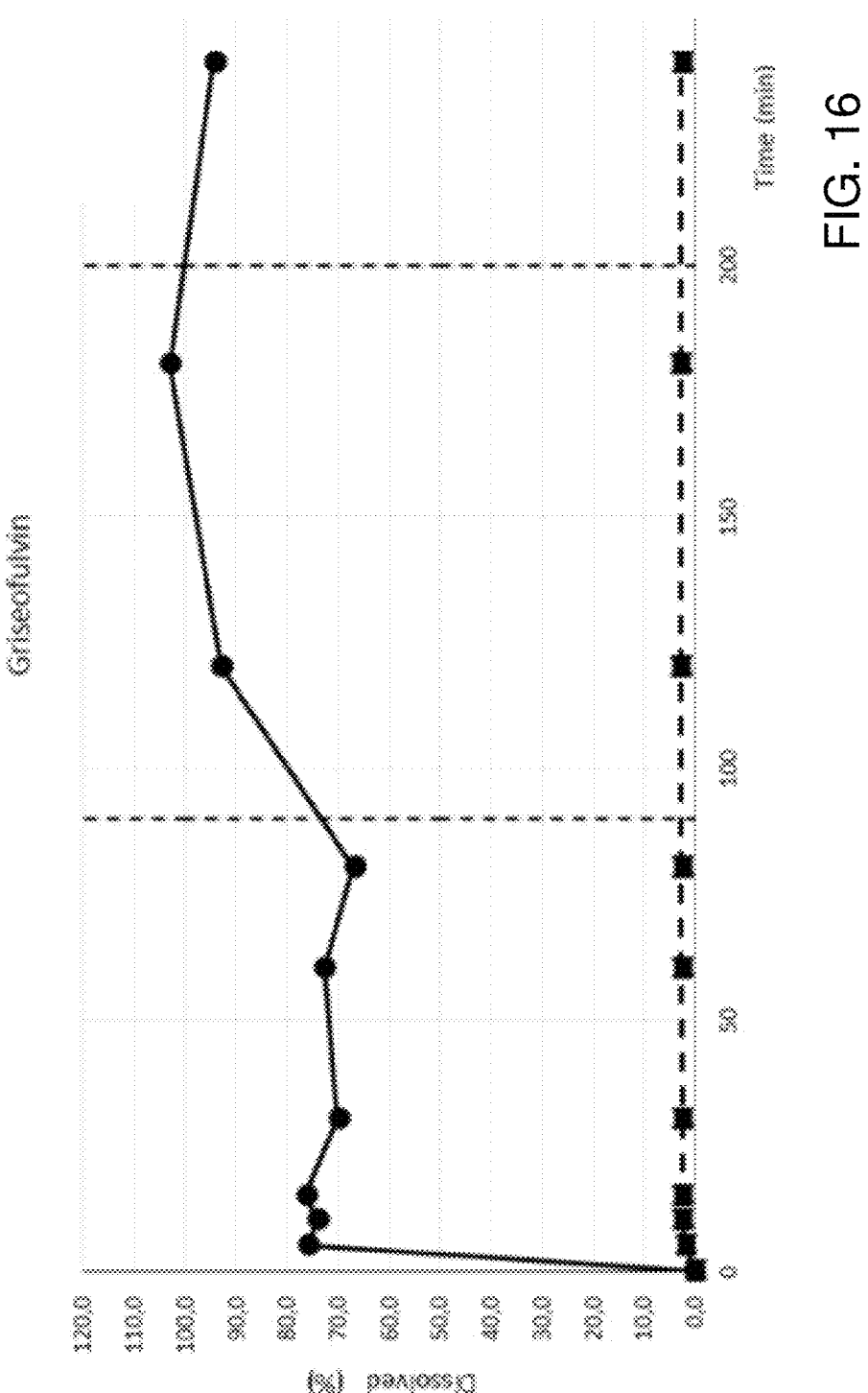

FIG. 16: Graph of a dissolution profile displaying the average dissolution (%) of a (spray dried) formulation comprising 20% Griseofulvin and 80% BSA (w/w) in function of the dissolution time (min). The results can be found discussed further in Example 9 and the legend is as follows: circle with full line—as film; triangle with dotted line—as powder.

Figure 17:
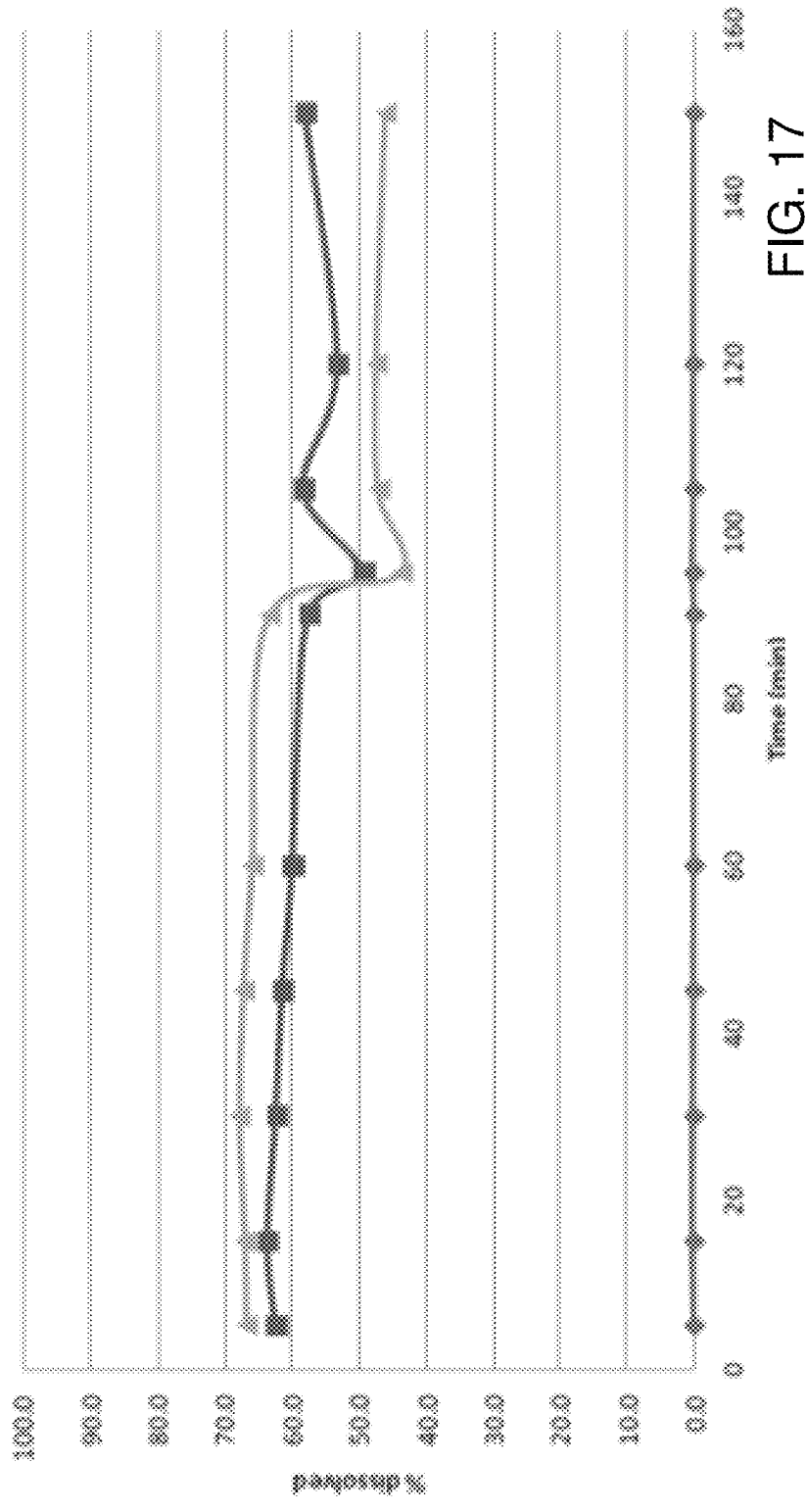

FIG. 17: Graph showing dissolution results for formulations comprising Vemurafenib in comparison with a commercially available product. The results can be found discussed further in Example 11 and the legend is as follows: squares—(30% Itraconazol and 70% BSA); triangles—(40% Itraconazol and 60% BSA); diamonds—reference (Sporanox).

Figure 18:
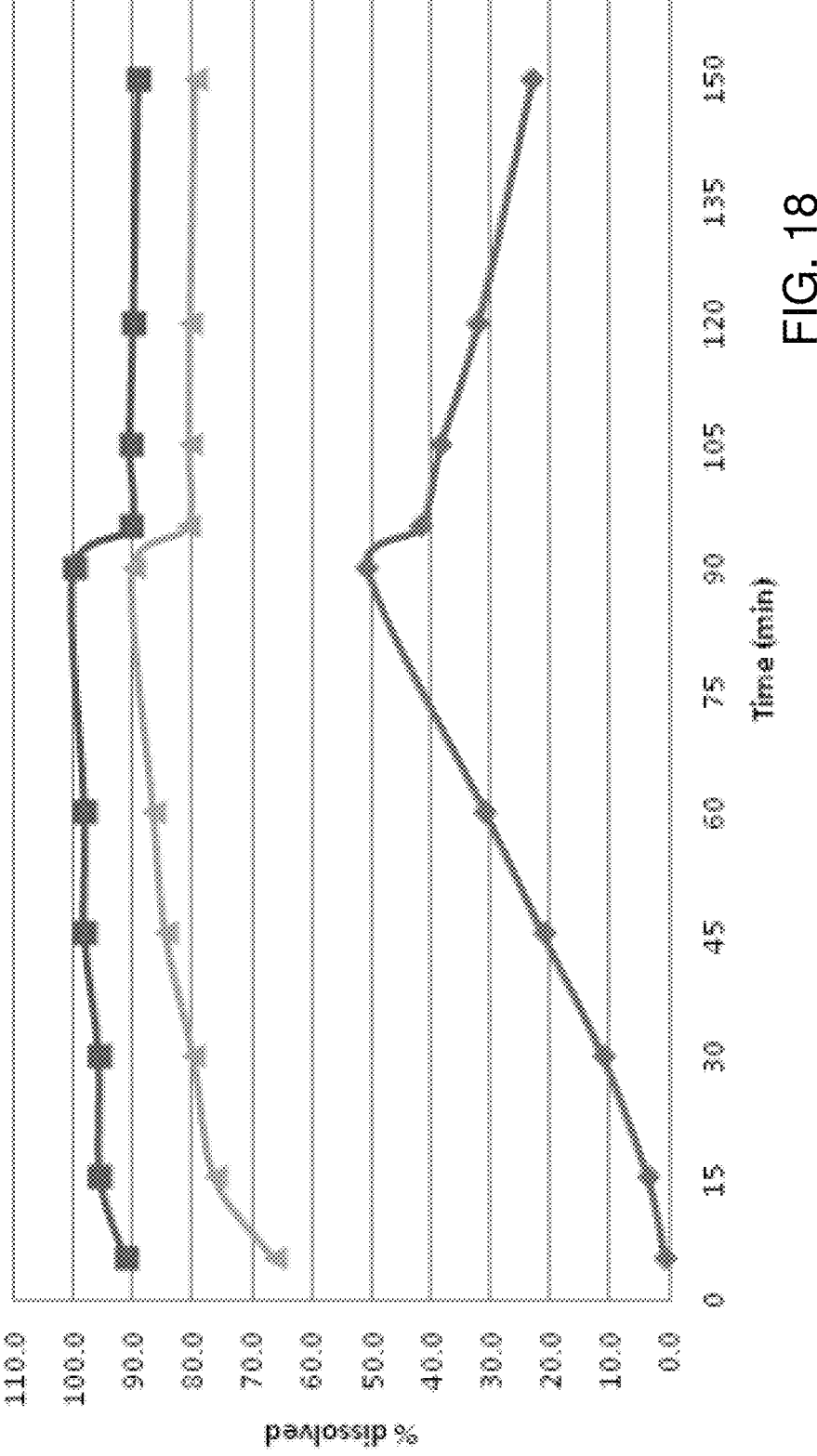

FIG. 18: Graph showing dissolution results for formulations comprising litraconazole in comparison with a commercially available product. The results can be found discussed further in Example 11 and the legend is as follows: the squares—(10% Vemurafenib and 90% BSA); triangles—(20% Vemurafenib and 80% BSA); diamonds—reference (Zelboraf).

Figure 19:
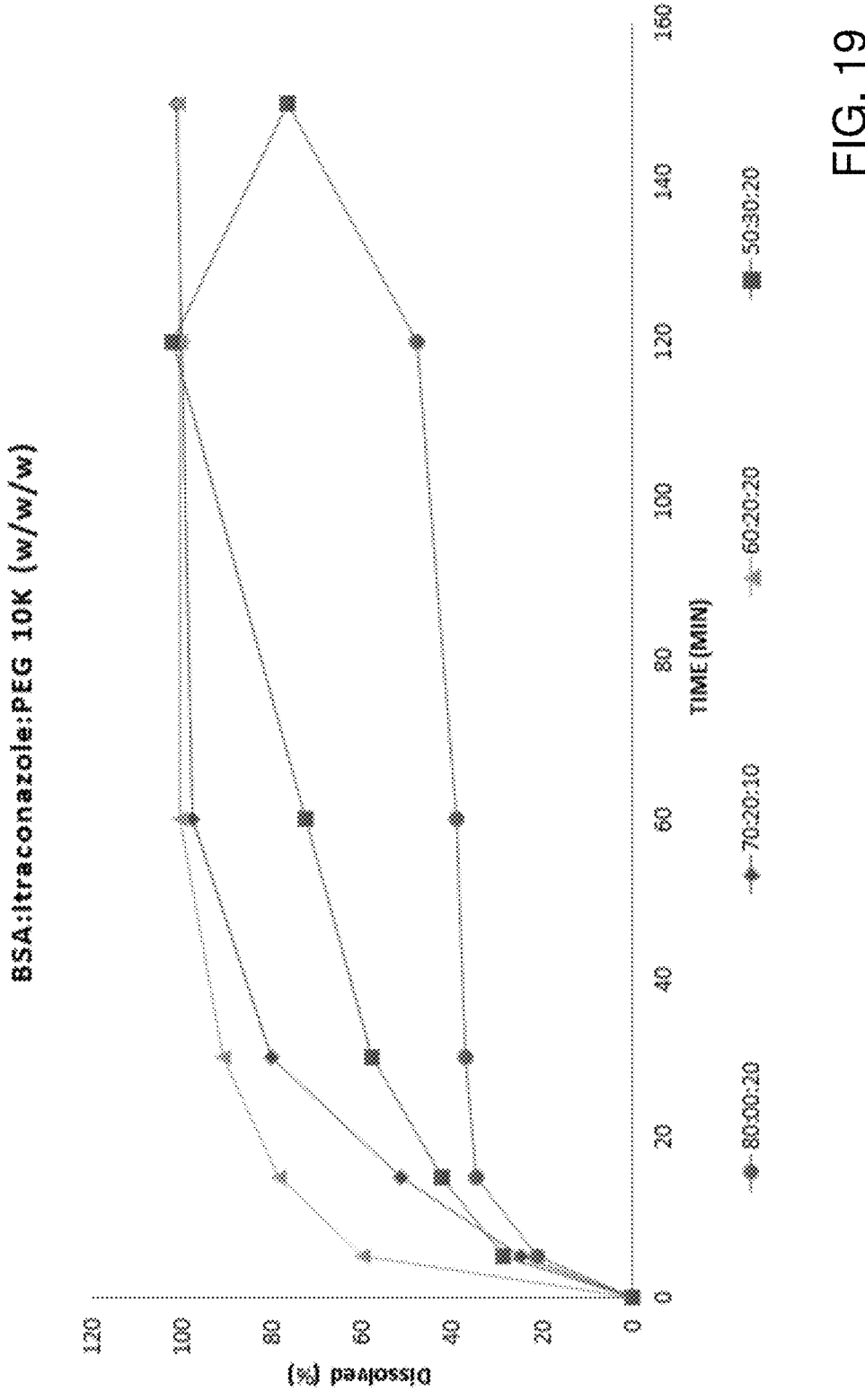

FIG. 19: shows a graph of a dissolution profile displaying the average dissolution (%) of formulations comprising BSA:ltraconazole:PEG 10K in function of the dissolution time (min). The results can be found discussed further in Example 12 and the legend is as follows: circles—(80% BSA and 20% Itraconazole); diamonds—(80% BSA, 20% Itraconazole and 10% PEG10K); triangles—(60% BSA, 20% Itraconazole and 20% PEG10K); squares (50% BSA, 30% Itraconazole and 20% PEG10K).

Figure 20:
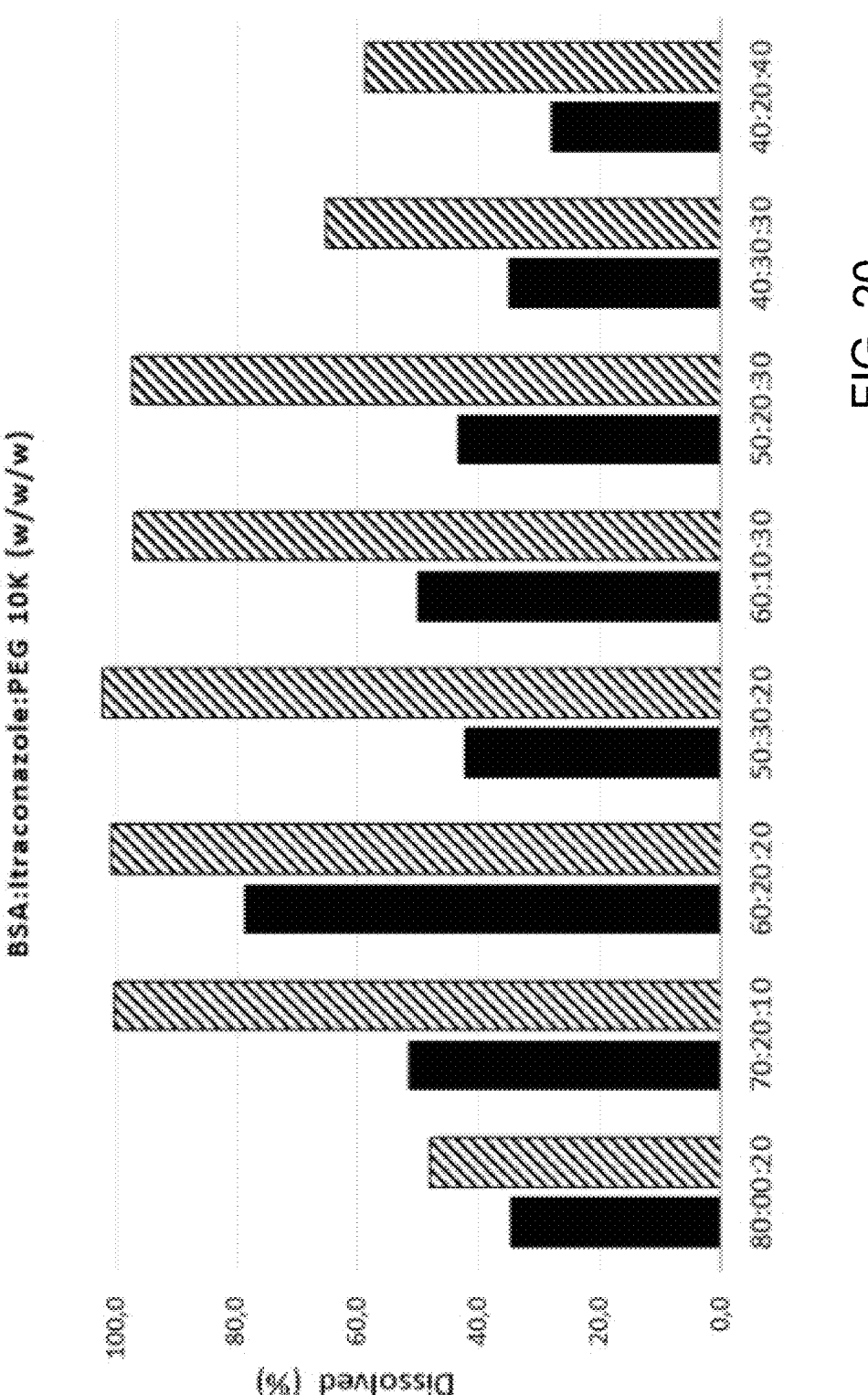

FIG. 20: shows comparative charts displaying the average dissolution (%) of formulations comprising BSA:ltraconazole:PEG 10K after 15 min (full black) and after 120 min (downward diagonal) of dissolution time. The numbers underneath the bars represent the BSA:ltraconazole:PEG 10K ratios and the results can be found discussed further in Example 12.

Figure 21:
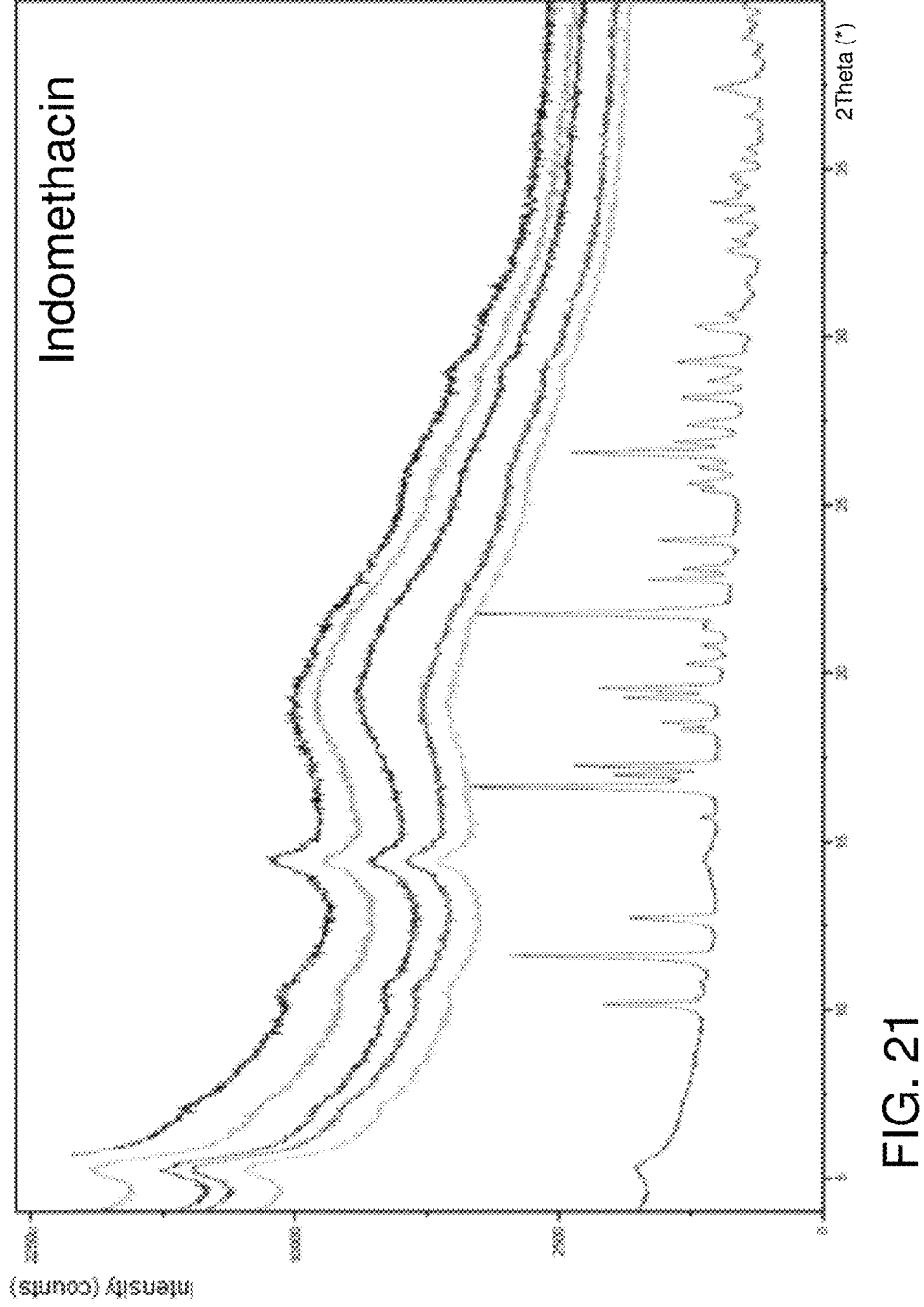

FIG. 21: Graph of XRD patterns of (freeze dried) formulations comprising Indomethacin as API and gelatin as excipient; wherein the bottom line represents sample 1 (pure Indomethacin) and serves as reference, next, from the bottom up, the following lines represent sample 6 (mean 5%), sample 5 (mean 10%), sample 4 (mean 20%), sample 3 (mean 30%), and sample 2 (mean 40%), respectively. The results can be found discussed further in Example 13.

Figure 22:
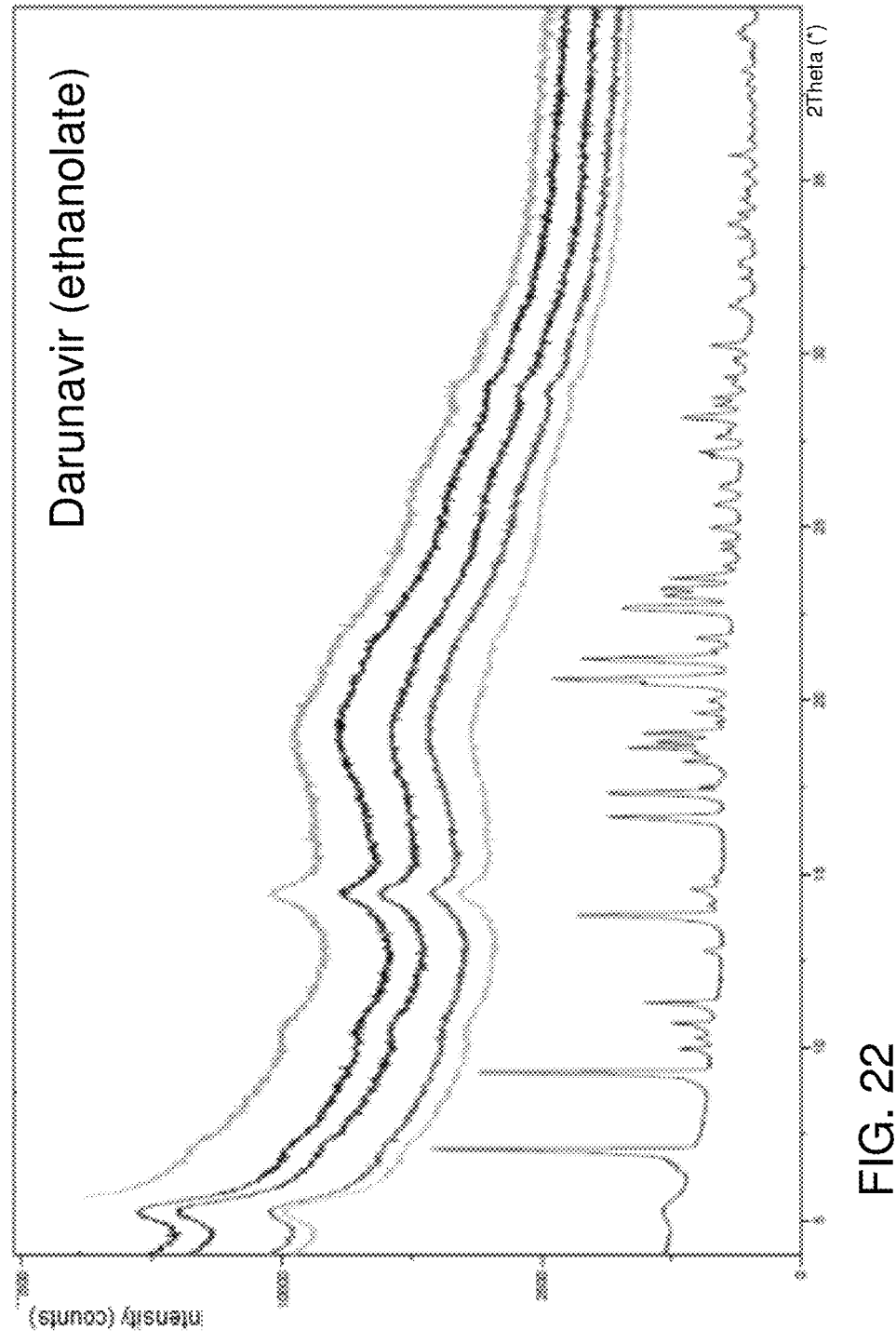

FIG. 22: Graph of XRD patterns of (freeze dried) formulations comprising Darunavir as API and gelatin as excipient; wherein the bottom line represents sample 1 (pure Darunavir) and serves as reference, next, from the bottom up, the following lines represent sample 6 (mean 5%), sample 5 (mean 10%), sample 4 (mean 20%), sample 2 (mean 40%), and sample 3 (mean 30%), respectively, The results can be found discussed further in Example 13.

Figure 23:
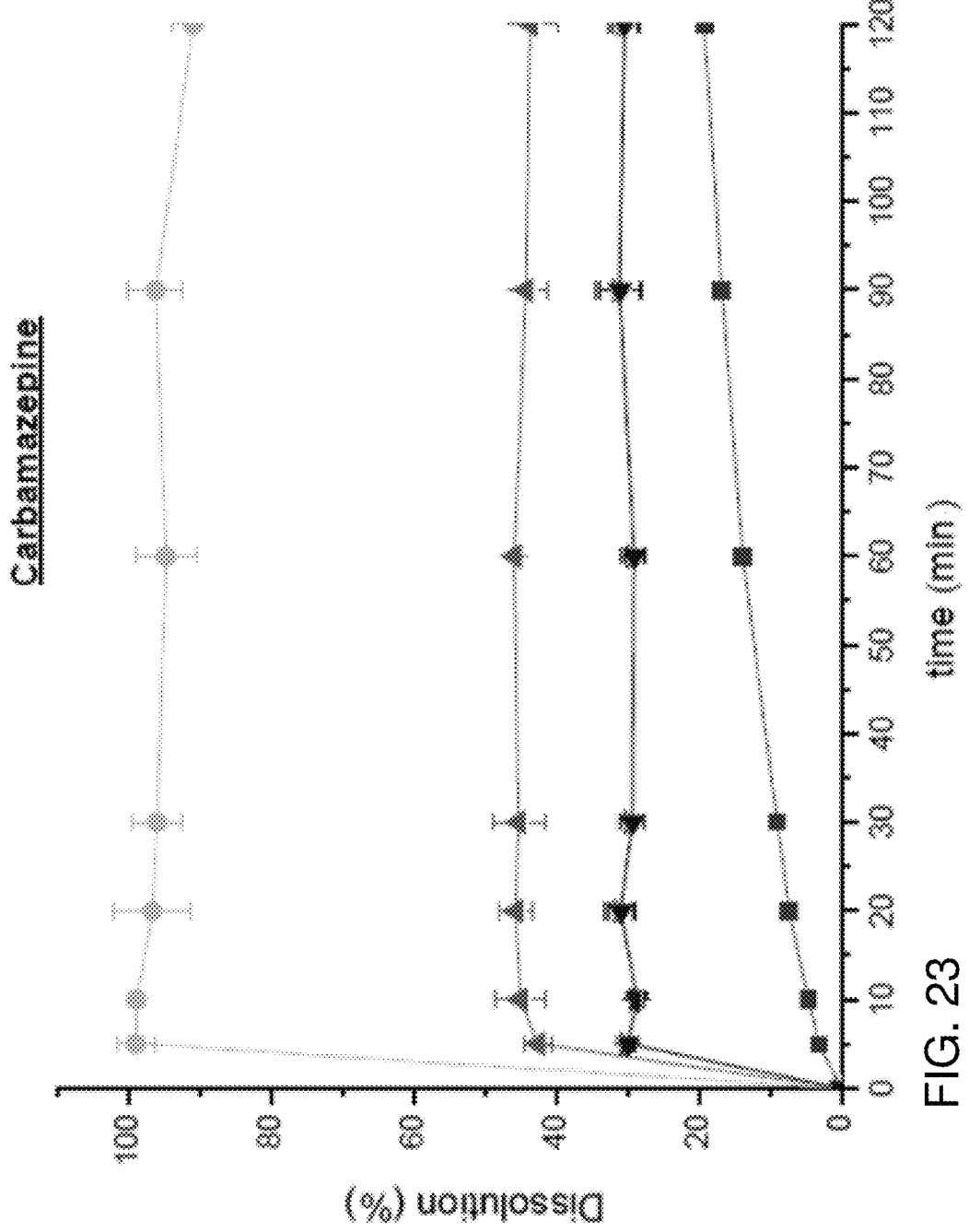

FIG. 23: Graph of a dissolution profile displaying the average dissolution (%) of a (freeze dried from DMSO solubilized feedstock) formulation comprising Carbamazepine and gelatin in function of the dissolution time (min). The results can be found discussed further in Example 14 and the legend is as follows: squares—pure Carbamazepine; circle—mean 5%; triangle (pointing up)—mean 10%; inverse triangle (pointing down)—mean 20%; diamond—mean 30%; cut triangle (pointing left)—mean 40%.

Figure 24:
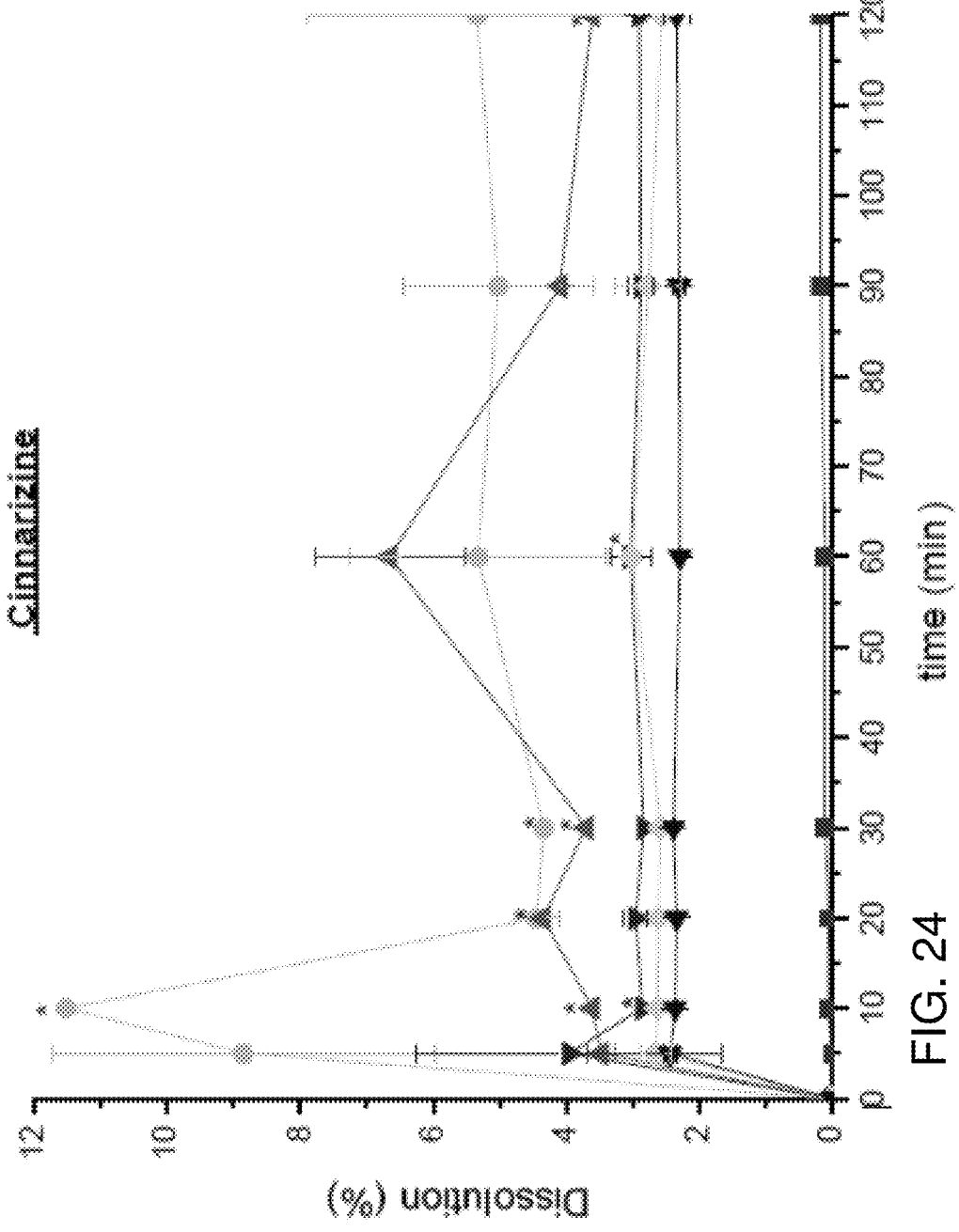

FIG. 24: Graph of a dissolution profile displaying the average dissolution (%) of a (freeze dried from DMSO solubilized feedstock) formulation comprising Cinnarizine and gelatin in function of the dissolution time (min). The results can be found discussed further in Example 14 and the legend is as follows: squares—pure Carbamazepine; circle—mean 5%; triangle (pointing up)—mean 10%; inverse triangle (pointing down)—mean 20%; diamond—mean 30%; cut triangle (pointing left)—mean 40%.

Figure 25:
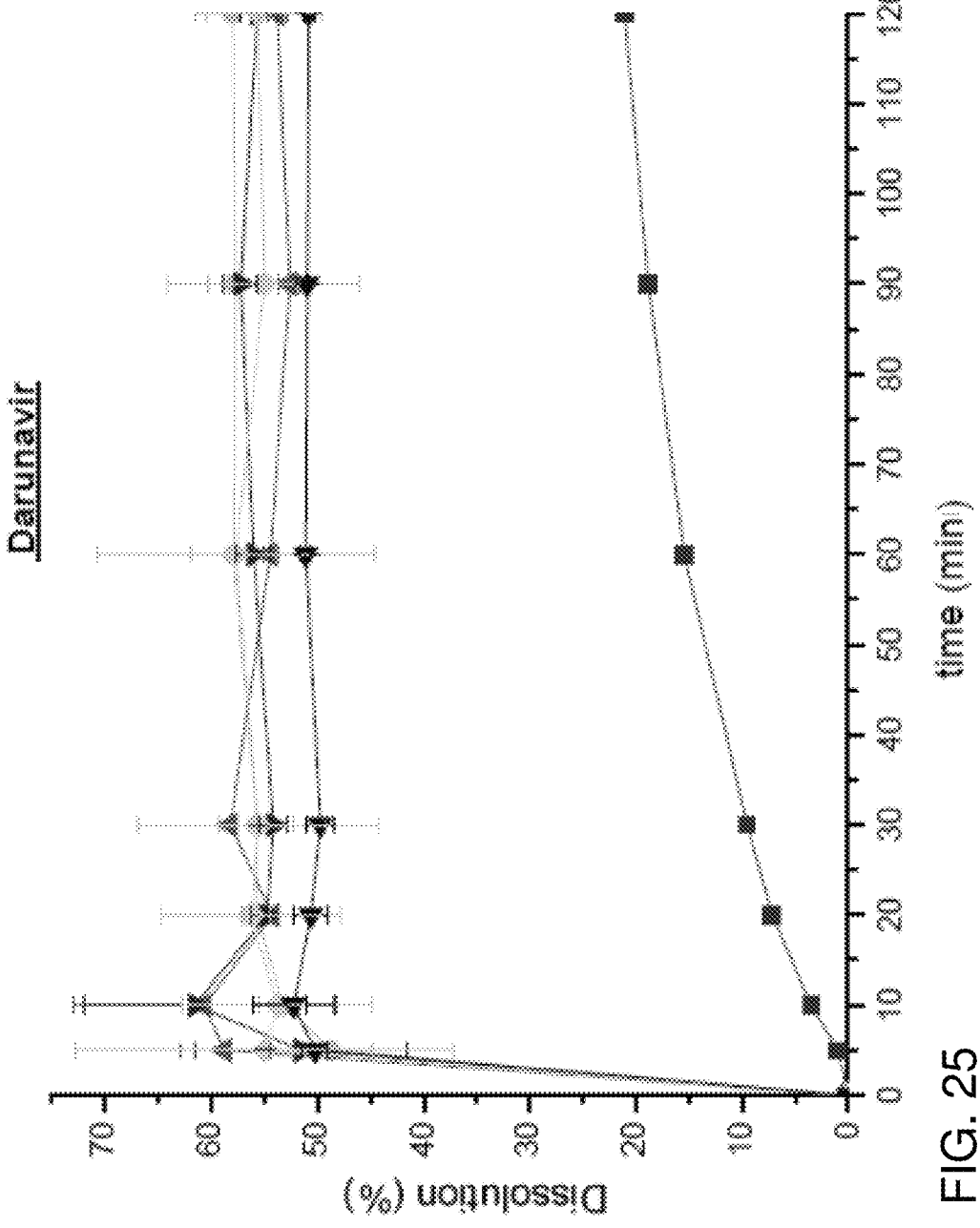

FIG. 25: Graph of a dissolution profile displaying the average dissolution (%) of a (freeze dried from DMSO solubilized feedstock) formulation comprising Darunavir (ethanolate) and gelatin in function of the dissolution time (min). The results can be found discussed further in Example 14 and the legend is as follows: squares—pure Carbamazepine; circle—mean 5%; triangle (pointing up)—mean 10%; inverse triangle (pointing down)—mean 20%; diamond—mean 30%; cut triangle (pointing left)—mean 40%.

Figure 26:
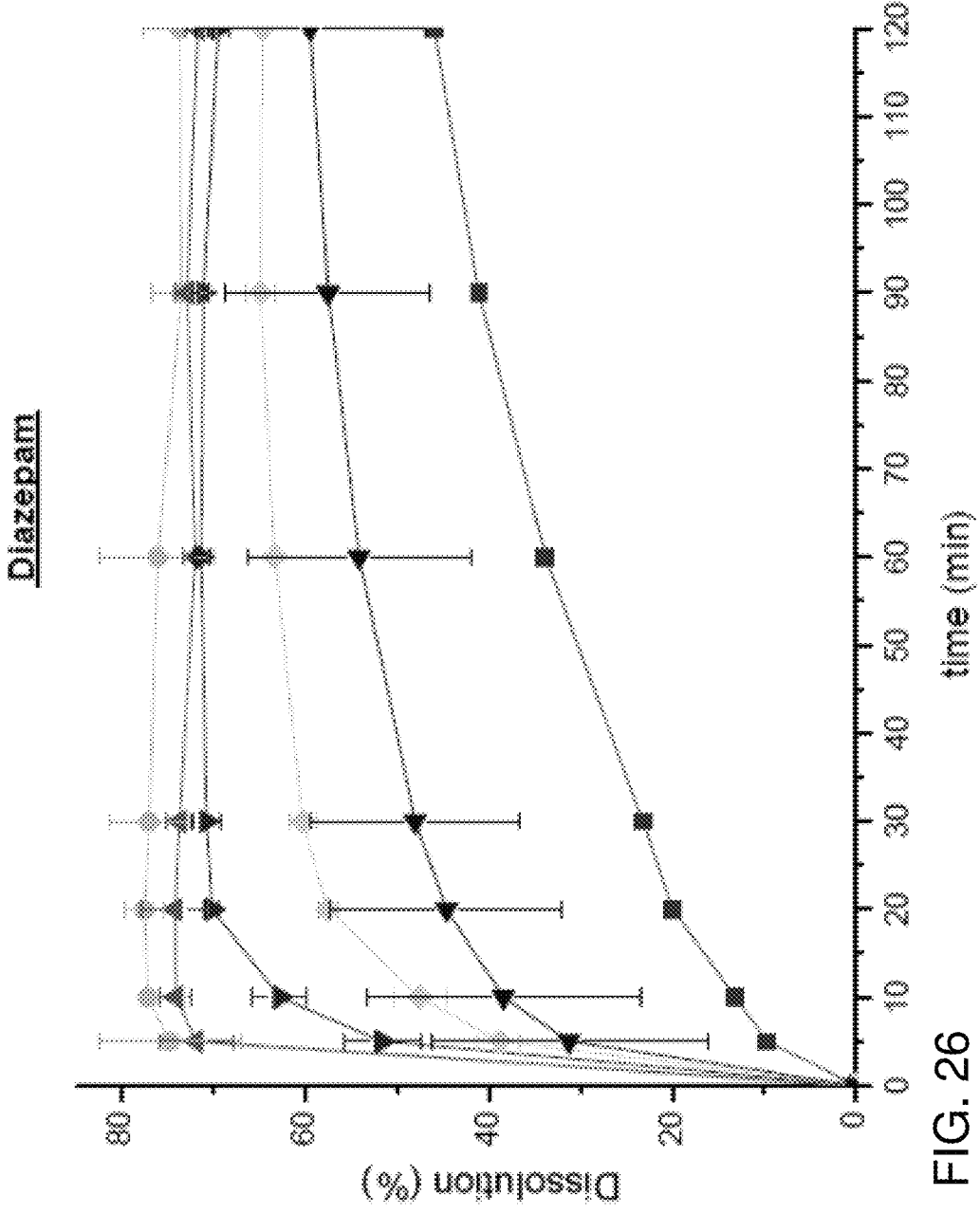

FIG. 26: Graph of a dissolution profile displaying the average dissolution (%) of a (freeze dried from DMSO solubilized feedstock) formulation comprising Diazepam and gelatin in function of the dissolution time (min). The results can be found discussed further in Example 14 and the legend is as follows: squares—pure Carbamazepine; circle—mean 5%; triangle (pointing up)—mean 10%;

inverse triangle (pointing down)—mean 20%; diamond—mean 30%; cut triangle (pointing left)—mean 40%.

Figure 27:
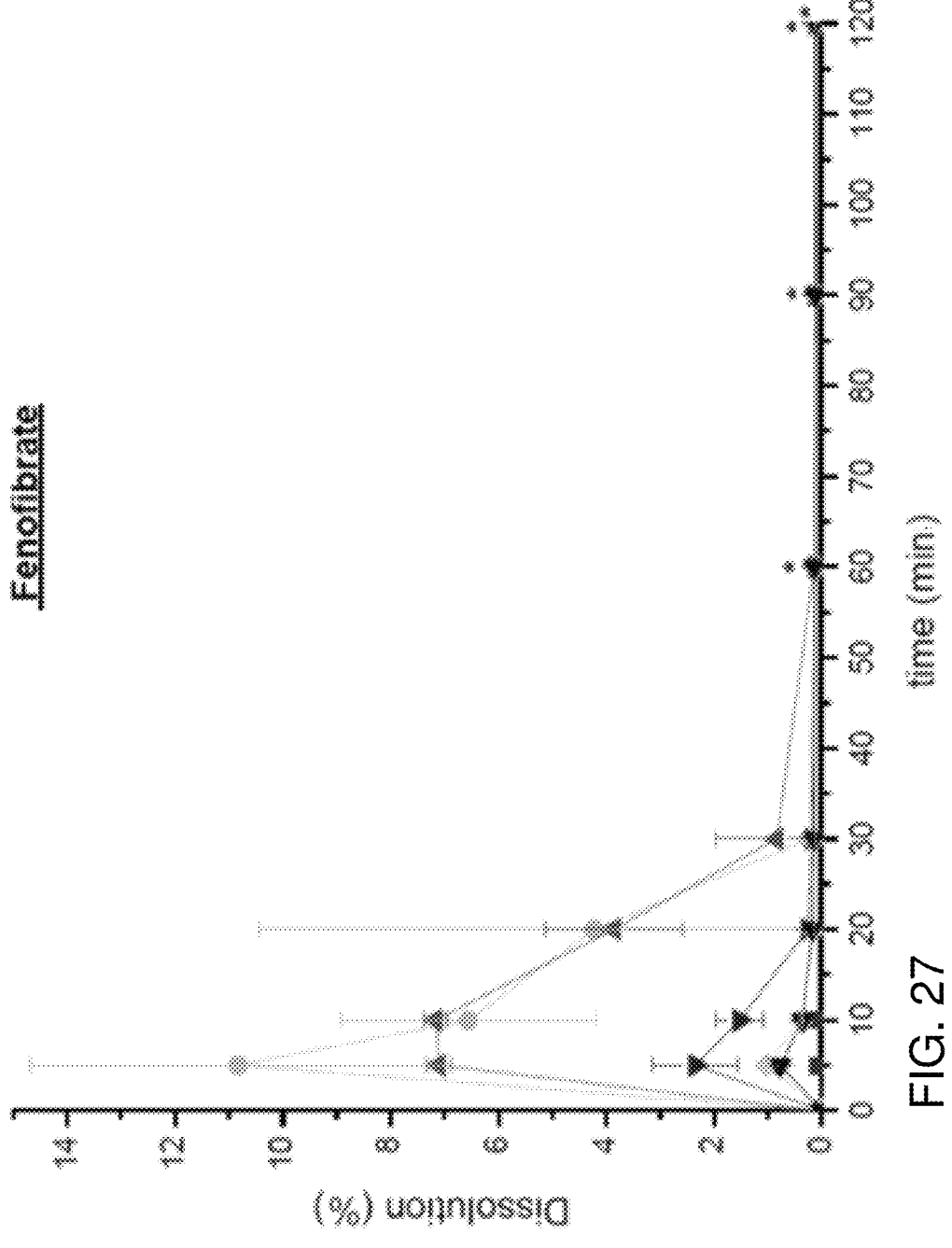

FIG. 27: Graph of a dissolution profile displaying the average dissolution (%) of a (freeze dried from DMSO solubilized feedstock) formulation comprising Fenofibrate and gelatin in function of the dissolution time (min). The results can be found discussed further in Example 14 and the legend is as follows: squares—pure Carbamazepine; circle—mean 5%; triangle (pointing up)—mean 10%; inverse triangle (pointing down)—mean 20%; diamond—mean 30%; cut triangle (pointing left)—mean 40%.

Figure 28:
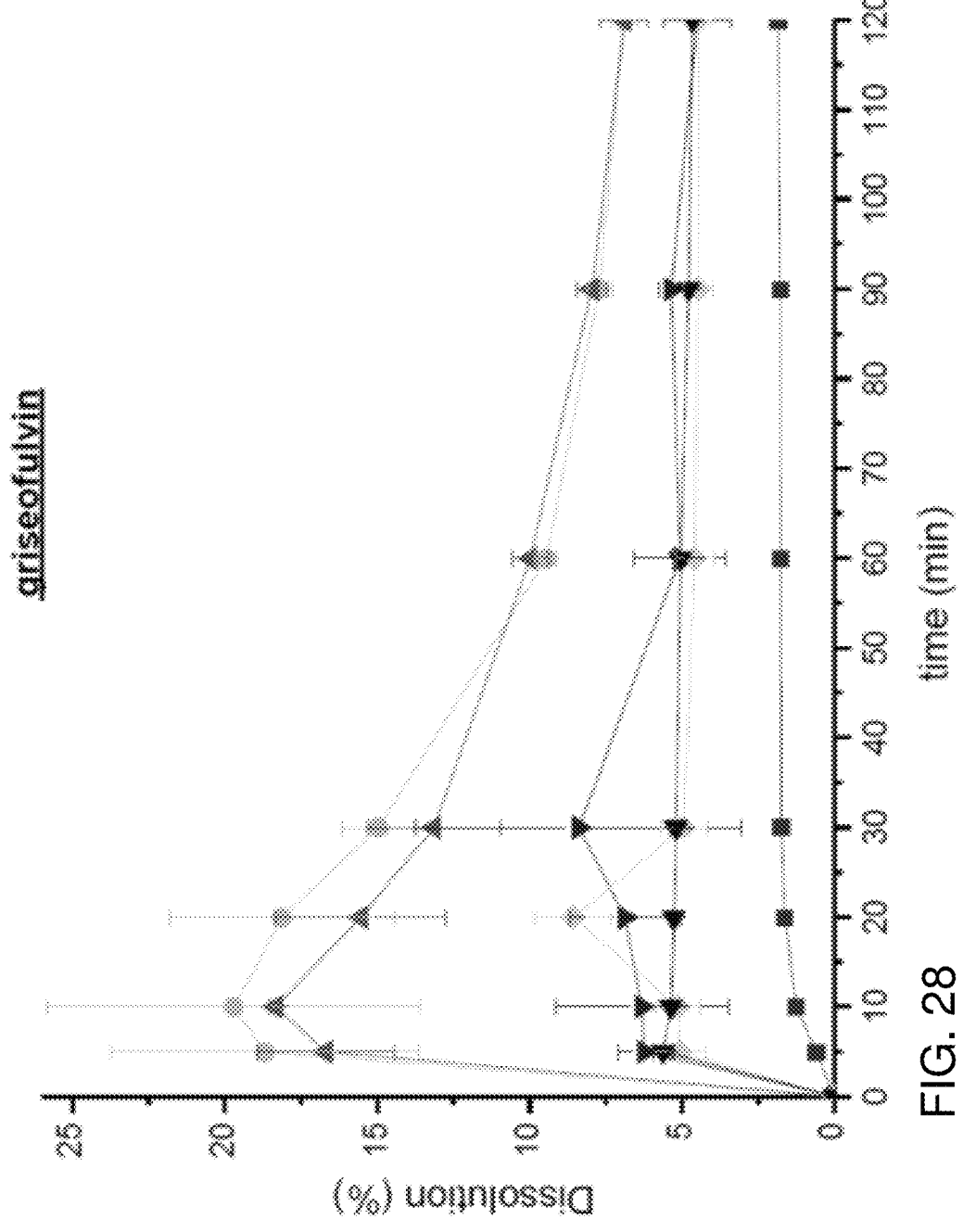

FIG. 28: Graph of a dissolution profile displaying the average dissolution (%) of a (freeze dried from DMSO solubilized feedstock) formulation comprising Griseofulvin and gelatin in function of the dissolution time (min). The results can be found discussed further in Example 14 and the legend is as follows: squares—pure Carbamazepine; circle—mean 5%; triangle (pointing up)—mean 10%; inverse triangle (pointing down)—mean 20%; diamond—mean 30%; cut triangle (pointing left)—mean 40%.

Figure 29:
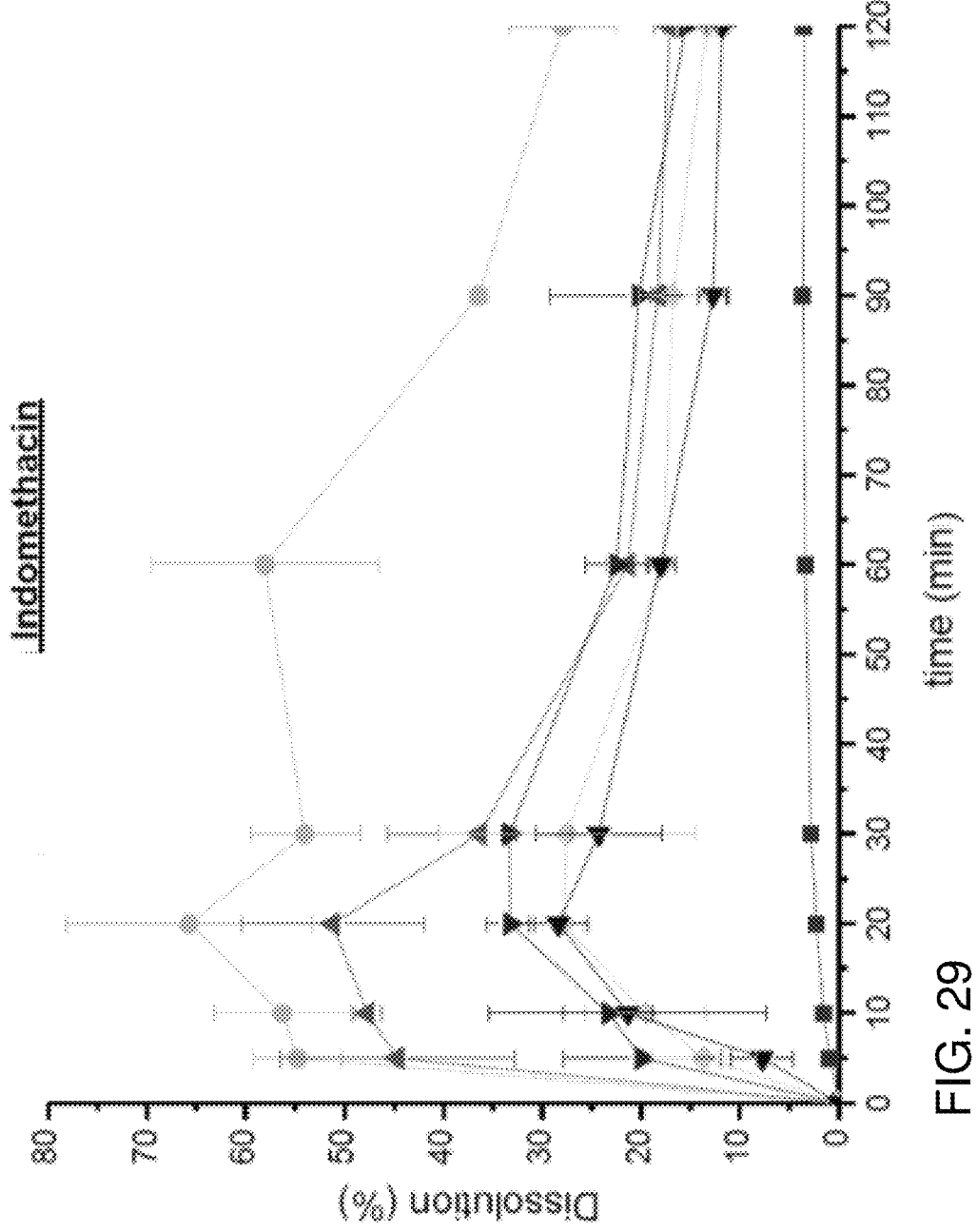

FIG. 29: Graph of a dissolution profile displaying the average dissolution (%) of a (freeze dried from DMSO solubilized feedstock) formulation comprising Indomethacin and gelatin in function of the dissolution time (min). The results can be found discussed further in Example 14 and the legend is as follows: squares—pure Carbamazepine; circle—mean 5%; triangle (pointing up)—mean 10%; inverse triangle (pointing down)—mean 20%; diamond—mean 30%; cut triangle (pointing left)—mean 40%.

Figure 30:
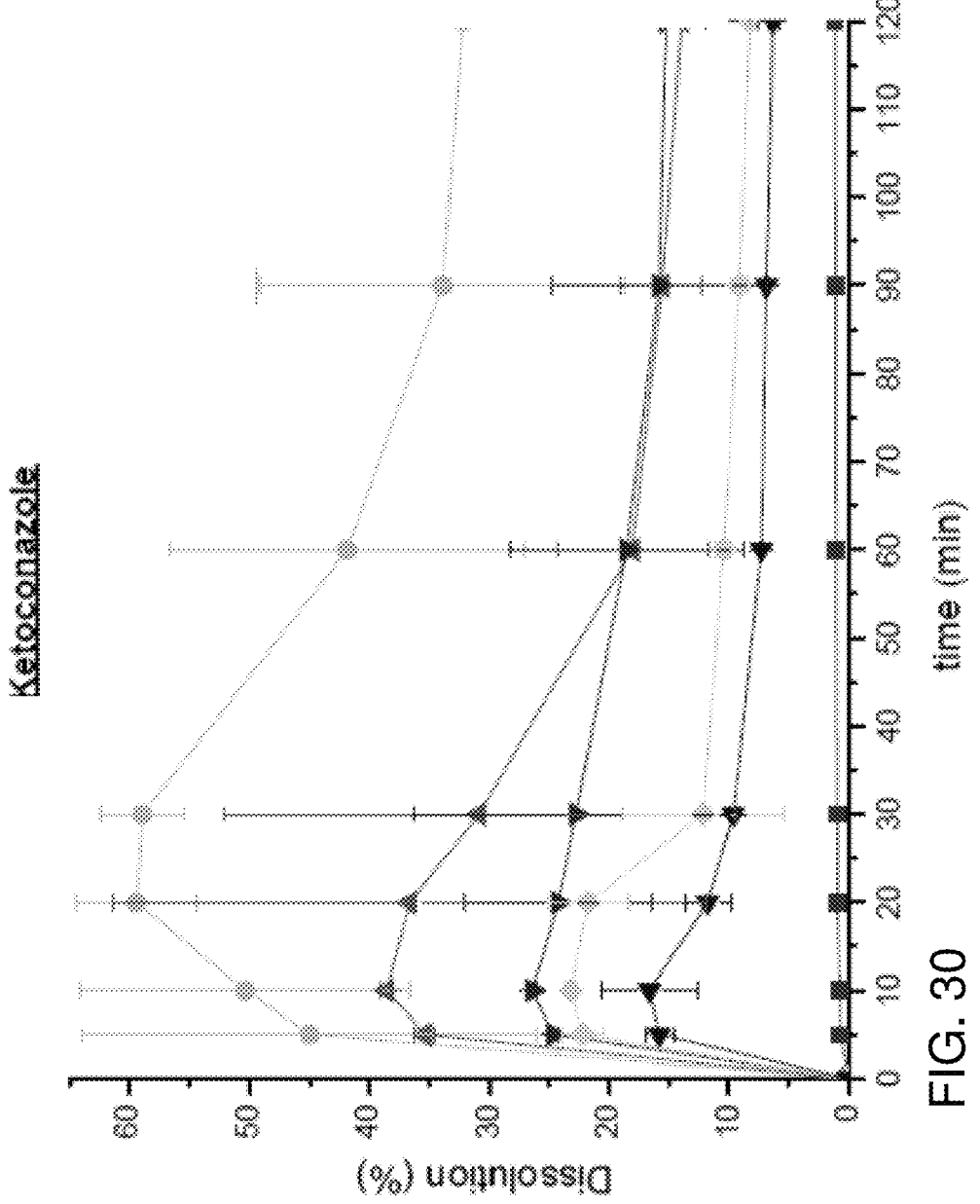

FIG. 30: Graph of a dissolution profile displaying the average dissolution (%) of a (freeze dried from DMSO solubilized feedstock) formulation comprising Ketoconazole and gelatin in function of the dissolution time (min). The results can be found discussed further in Example 14 and the legend is as follows: squares—pure Carbamazepine; circle—mean 5%; triangle (pointing up)—mean 10%; inverse triangle (pointing down)—mean 20%; diamond—mean 30%; cut triangle (pointing left)—mean 40%.

Figure 31:
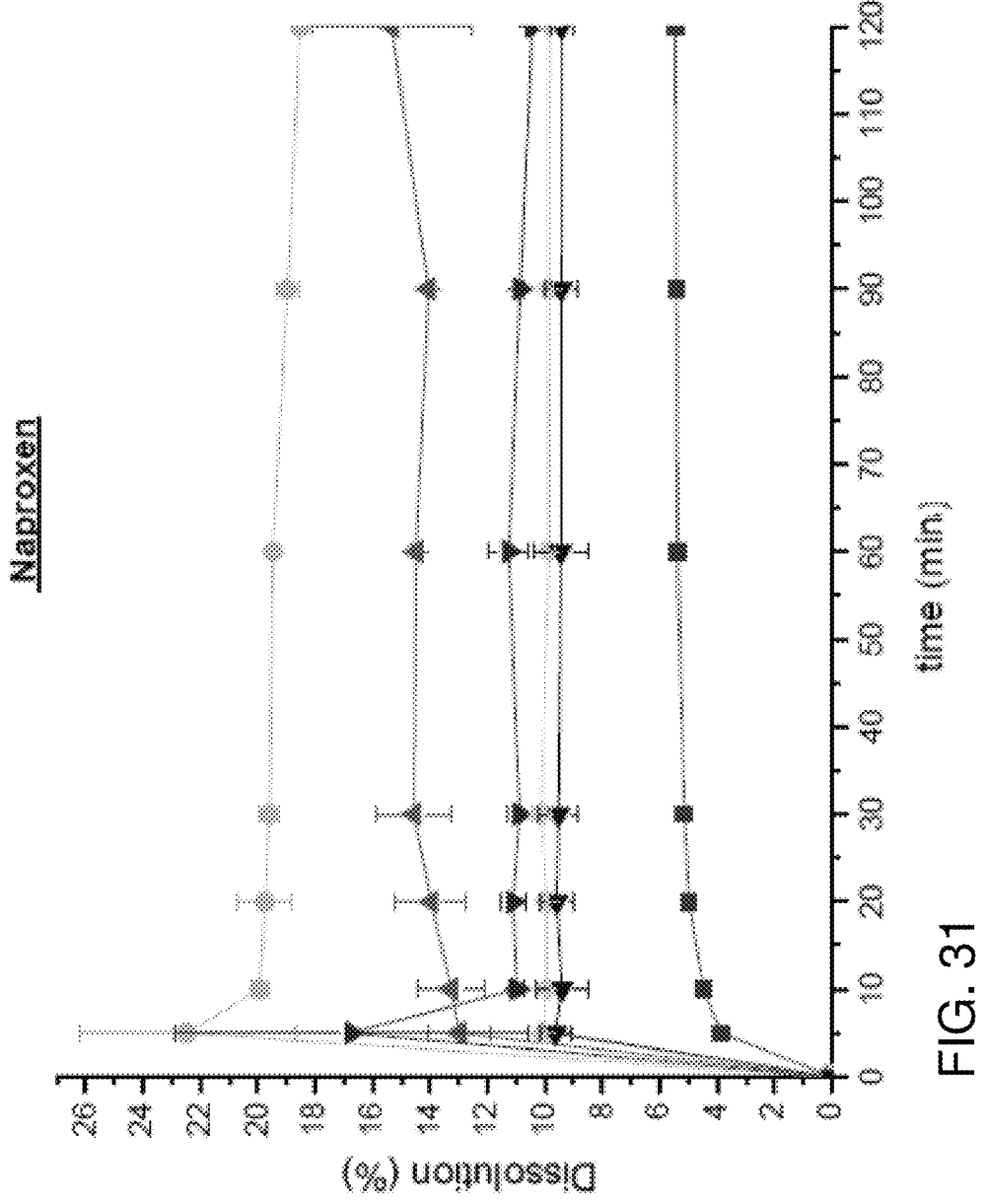

FIG. 31: Graph of a dissolution profile displaying the average dissolution (%) of a (freeze dried from DMSO solubilized feedstock) formulation comprising Naproxen and gelatin in function of the dissolution time (min). The results can be found discussed further in Example 14 and the legend is as follows: squares—pure Carbamazepine; circle—mean 5%; triangle (pointing up)—mean 10%; inverse triangle (pointing down)—mean 20%; diamond—mean 30%; cut triangle (pointing left)—mean 40%.

Figure 32:
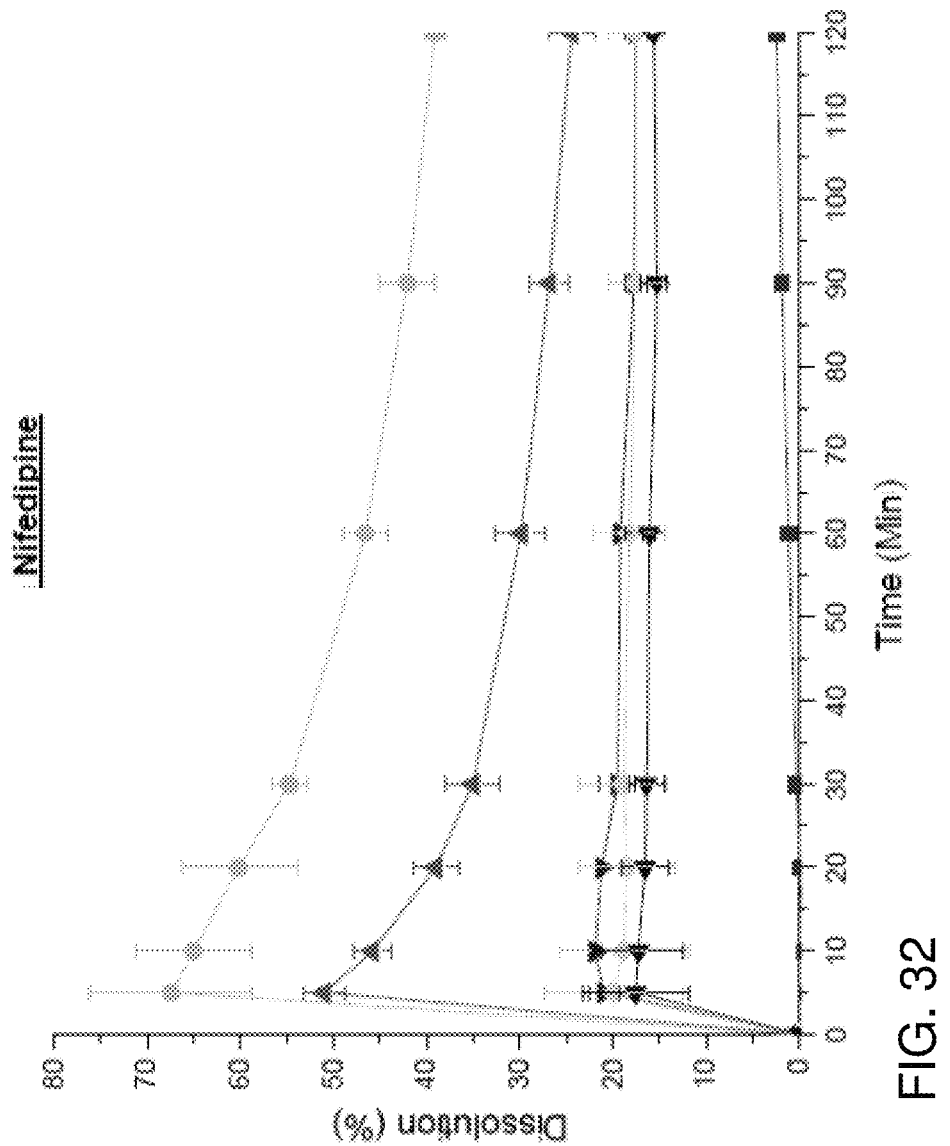

FIG. 32: Graph of a dissolution profile displaying the average dissolution (%) of a (freeze dried from DMSO solubilized feedstock) formulation comprising Nifedipine and gelatin in function of the dissolution time (min). The results can be found discussed further in Example 14 and the legend is as follows: squares—pure Carbamazepine; circle—mean 5%; triangle (pointing up)—mean 10%; inverse triangle (pointing down)—mean 20%; diamond—mean 30%; cut triangle (pointing left)—mean 40%.

Figure 33:
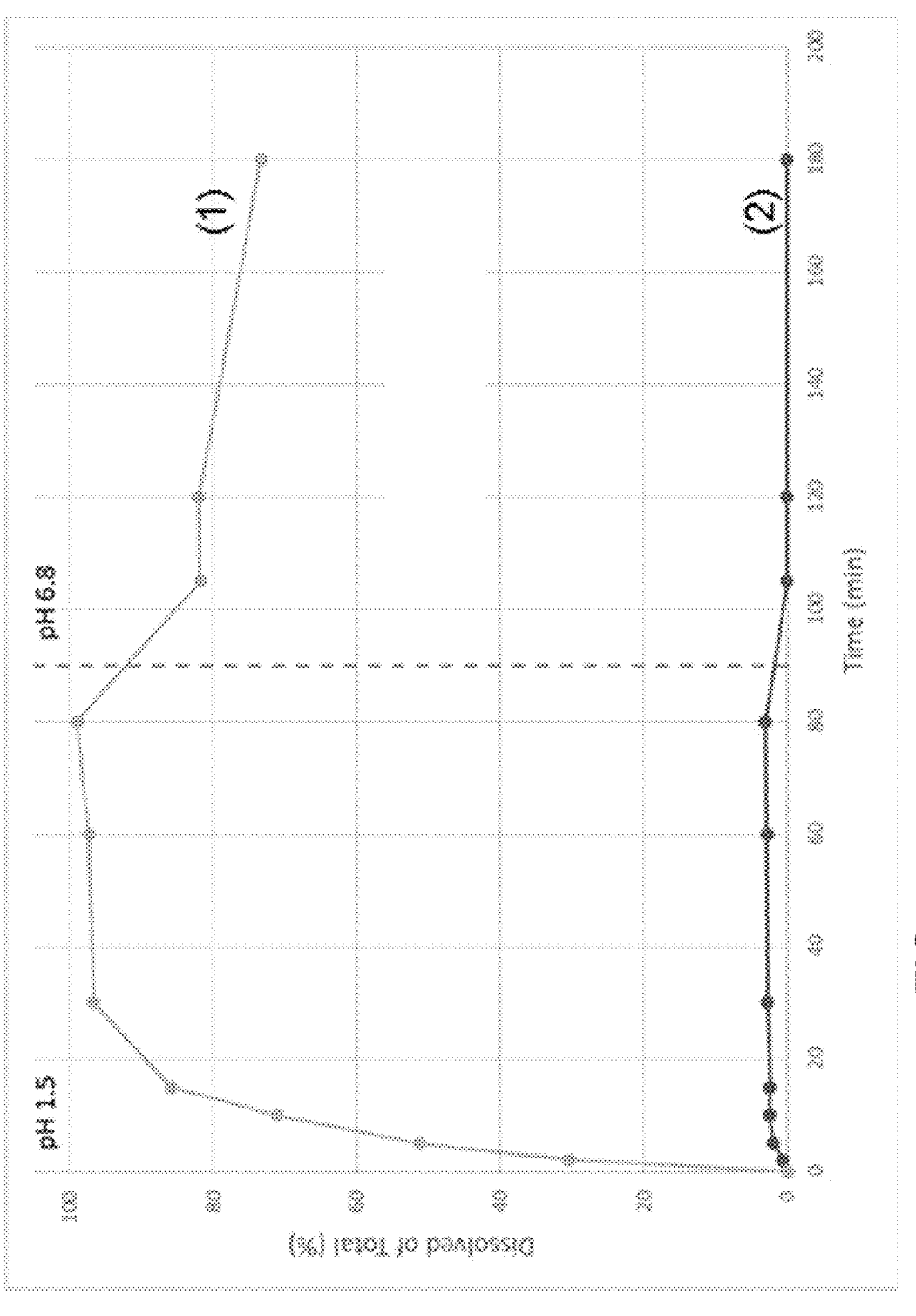

FIG. 33: Graph of a dissolution profile displaying the average dissolution (%) of a (freeze dried from DMSO (pH 2.3) solubilized feedstock) formulation comprising Itraconazole and BSA in function of the dissolution time (min). The results can be found discussed further in Example 15 and the legend is as follows: bottom line (1)—freeze dried formulation (as amorphous solid dispersionD); top line (2)—crystalline Itraconazole.

DETAILED DESCRIPTION OF THE INVENTION

Before the present system and method of the invention are described, it is to be understood that this invention is not limited to particular systems and methods or combinations described, since such systems and methods and combinations may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of".

The recitation of numerical ranges by endpoints includes all numbers and fractions subsumed within the respective ranges, as well as the recited endpoints.

The term "about" or "approximately" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

In the present description of the invention, reference is made to the accompanying drawings that form a part hereof, and in which are shown by way of illustration only of specific embodiments in which the invention may be practiced. Parenthesized or emboldened reference numerals affixed to respective elements merely exemplify the elements by way of example, with which it is not intended to limit the respective elements. It is to be understood that other embodiments may be utilised and structural or logical changes may be made without departing from the scope of the present invention. The following detailed description, therefore, is not to be taken in a limiting sense, and the scope of the present invention is defined by the appended claims.

Any drug is generally composed of two components or aspects. The first is the actual API which is the central ingredient. The second is known as an excipient. This refers to the substance inside the drug or tablet. If it is in syrup form, then the excipient will be the liquid that has been used.

As used herein the term "active pharmaceutical ingredient" (API) generally refers to a substance in a pharmaceutical formulation that is biologically active and is meant to produce the desired effect in the body. Other terms such as "active substance", "active constituent" and "active ingredient" designate a shared definition and may be used interchangeably.

The APIs are categorized into four classes according to the biopharmaceutics classification system, which differentiates APIs based on their solubility, (intestinal) permeability and dissolution (rate). This system is particularly suitable to classify orally administered API, but may also serve as a general classification system. More information can be found in the "Waiver of In Vivo Bioavailability and Bioequivalence Studies for Immediate-Release Solid Oral Dosage Forms Based on a Biopharmaceutics Classification System Guidance for Industry" issued by the U.S. Department of Health and Human Services Food and Drug Administration Center for Drug Evaluation and Research (ref: CDER waiver on API classes).

The solubility class boundary is based on the highest dose strength of an immediate release product. An API is considered 'highly soluble' when the highest dose strength is fully soluble in 250 ml (or less) of solvent (e.g. aqueous media) over the pH range of 1 to 7.5. An API is considered 'poorly soluble' when the highest dose strength is not fully soluble in 250 ml (or more) of solvent over the pH range of 1 to 7.5; it is considered 'not soluble' or 'insoluble' when the dose reaches less than 0.1 g per 100 mL of solvent. The volume estimate of 250 ml is derived from typical bioequivalence study protocols that prescribe administration of a drug product to fasting human volunteers with a glass of water. Detailed technical information (e.g. protocols and equipment) on determining the API's solubility class may be found in the CDER waiver on API classes.

The permeability class boundary is based on the measurement of rates of mass transfer across human intestinal membrane, or indirectly on the extent of absorption of an API in humans. An API is considered 'highly permeable' when the extent of absorption in humans is determined to be 90% or more, for example 95% or 100%, of the administered dose based on a mass-balance determination or in comparison to an intravenous dose. An API is considered 'poorly permeable' when the extent of absorption in humans is determined to be 50% or less, for example 30% or 40%, of the administered dose based on a mass-balance determination or in comparison to an intravenous dose; it is considered 'not permeable' when the extent of absorption in humans is determined to be 10% or less, for example 5% or 0%. Alternatively, non-human systems (e.g. pigs) capable of predicting API absorption in humans can be used. Detailed technical information on determining the API's permeability class may be found in the CDER waiver on API class.

The dissolution (rate) class boundary is based on the highest measurable concentration level a solid product achieves in a set amount of time when submerged in a solvent (e.g. liquid aqueous media) over the pH range of 1 to 7.5. An immediate release product (comprising an API) is considered 'rapidly dissolving' when no less than 85% of the labelled amount of the API substance dissolves within 15 minutes using a standardized dissolution apparatus stirring 100 RPM in a volume of 900 ml or less in two different simulating media, the first medium having a pH of 4.5 (i.e. gastric fluid) and the second 6.8 (i.e. intestinal fluid). An immediate release product (comprising an API) is considered as 'slowly dissolving' when less than 50% of the labelled amount of the API substance dissolves within 15 minutes using a standardized dissolution apparatus stirring 100 RPM in a volume of 900 ml or less in two different simulating media with a pH of 4.5 and 6.8. Detailed technical information on determining the API's dissolution (rate) class may be found in the CDER waiver on API classes.

The Class I APIs show a high permeability and high solubility, which allows them to be well absorbed over the intestinal mucosa. An example of a Class I API is metoprolol. The Class II APIs are characterized by a high permeability but a low solubility, which causes the bioavailability of these API to be limited by their dissolution rate. Examples of a Class II API include Flubendazole, Carbamazepine, Griseofulvin, Phenytoin, Nifedipine, Verapamil, Azithromycin, Nitrofurantoin, Iopanoic acid, Itraconazole, Indomethacin, Glibenclamide, Bicalutamide, Ezetimibe, Aceclofenac, Ketoconazole, Oxfendazole, Fenofibrate, Cinnarizin, Darunavir, Diazepam, Testosterone undecanoate, or Naproxen, and others. The Class III APIs are characterized by a high solubility but a low permeability, which causes their absorption to be limited by the permeation rate. An example of a class III API is cimetidine. Lastly, the Class IV APIs show a low permeability and a low solubility, which causes a low absorption rate and a poor bioavailability is thus expected. Examples of a class IV API include Ritonavir, Saquinavir, Bifonazole, and others.

Traditionally the term excipient refers to a biologically inactive substance used in a pharmaceutical formulation, which serves as a medium for the substance that is active. However, for the purposes of the present invention the protein based excipient is preferably not biologically inactive, but instead interacts with the API thereby keeping it in solution or supersaturation. Generally speaking, the excipient thus serves as a solubility enhancer for the API. Thus a distinction is made between the 'protein based excipient', as used in the present invention, which is obtained from a natural substance, in particular protein-based, comprising a protein composition or hydrolysates thereof, and 'traditional excipients', which commonly are derived from a natural or synthetic substance, for example polymers. The traditional excipients may also be designated by other terms such as "inactive substance", "inactive constituent" and "inactive ingredient" which share a definition and may be used interchangeably. As used herein the term "excipient" generally refers to 'protein based excipient', unless mentioned otherwise (e.g. polymer excipient).

In a (first) general aspect the present invention relates to a formulation comprising a protein-based excipient and an API which are both substantially amorphous.

In particular, the present invention relates to a formulation comprising:

- a protein based excipient obtained from a protein composition or a hydrolysate thereof which comprises proteins—as per monomer—of at least 10 amino acids in length; and
- an active pharmaceutical ingredient (API);

characterized therein that said protein based excipient and said API are both substantially amorphous; preferably completely amorphous. Advantageously, said protein based excipient and said API form a substantially homogenous mixture, more preferably a completely homogenous mixture as an amorphous solid dispersion (ASD).

As used herein the term "formulation" generally refers to a material or mixture prepared according to a formula. For the purposes of the present the formulation comprises at least one (protein-based) excipient according to the present invention and at least one API, in particular an API exhibiting a low solubility, dissolution rate and/or bioavailability, thereby forming 'a pharmaceutical formulation'. Other terms such as "mixture" or "combination" generally designate a shared definition, unless indicated otherwise, and may be used interchangeably. A particular embodiment of a formulation is a "solid dispersion", which refers to a solid state system comprising of at least two different components, wherein a first component (e.g. the API) is effectively dispersed as amorphous phase in the matrix of the second component (e.g. the excipient). An (amorphous) solid dispersion (ASD) is a substantially homogeneous mixture; preferably a completely homogenous mixture. As used herein the terms "homogenous" or "non-heterogeneous" generally relate to the level of uniformity of a (solid) mixture lacking a clear structural distinction between the components of the mixture. A homogenous mixture is uniformly mixed and the components cannot be easily separated, contrary to a heterogeneous mixture that allows a clear distinction and/or separation of components (e.g. encapsulated materials, beads, shells, etc.). For the purposes of the present invention, a powder or solid dispersion is referred to as "substantially homogenous" when it contains almost no traces of heterogeneity, i.e. less than 10% preferably less than 7%; and it is referred to as "completely homogenous" when it contains no traces of heterogeneity, i.e. less than 5%; more preferably less than 3%, most preferably less than 1%. The homogeneity and/or heterogeneity can be verified experimentally (e.g., X-ray Powder Diffraction spectroscopy (XRD), Differential scanning calorimetry (DSC) for most powders or solid dispersions.

As used herein the term "protein" generally refers to a polymer chain, or multiple polymer chains, made of amino acids linked together by peptide (amide) bonds. Peptides as known in the art are biologically occurring short chains of amino acid monomers, wherein the shortest peptide may consist of two amino acids joined by a single peptide bond. Proteins are usually distinguished from peptides based on the arrangement of the amino acids in a biologically functional way. The excipient according to the present invention advantageously retains at least part of their biological activity; the excipient is therefore protein based.

For the purposes of the present invention, the proteins—as per monomer—incorporate at least 10 amino acids into their primary structure. Amino acids are natural monomers that polymerize at ribosomes to form proteins (polypeptides). In some embodiments of the present invention the protein based excipient is characterized in that it is obtained from a protein composition or a hydrolysate thereof which comprises proteins—as per monomer—of at least 10 amino acids in length; preferably at least 20 amino acids in length; preferably at least 50 amino acids in length; more preferably at least 100 amino acids in length; most preferably at least 250 amino acids in length, for example at least 250 amino acids, at least 500 amino acids, at least 750 amino acids, at least 1000 amino acids, or more. It is noted that the use of size, (amino acid) length or weight boundaries to distinguish peptides from proteins is not absolute and varies arbitrarily in research. As such, the protein's biological functionality is used as the primary point of distinction instead. Accordingly, no distinction is made based on the origin of the protein; that is, a native protein having functionality as a naturally occurring in a biological source (e.g. human, animal, plant, etc.); a recombinant protein that had its functionality improved or modified (e.g. cell cultures, yeast, etc.); or an artificial protein or scaffolds mimicking the functionality of a protein (e.g. alphabody, affimer, etc.). As used herein the terms "amorphous" or "non-crystalline" generally relate to a state of solid lacking a definite or clear shape or form, which would instead be characteristic of an (ordered) crystalline structure. An amorphous solid (mixture) lacks a structural long-range order and the components cannot be arranged in an periodic structure, contrary to a crystalline solid (mixture) that has a (highly) ordered microscopic structure that extends in all directions and can be arranged in a crystal lattice (e.g. salt, diamond, etc.). For the purposes of the present invention, a powder or solid dispersion is referred to as 'substantially amorphous' when it contains almost no traces of crystallinity, i.e. less than 10%, more preferably less than 7%; and it is referred to as 'completely amorphous' when it contains no traces of crystallinity, i.e. less than 5%, more preferably less than 3%, most preferably less than 1%. The amorphous and/or crystalline state can be verified experimentally (e.g., X-ray Powder Diffraction spectroscopy (XRD), Differential scanning calorimetry (DSC) for most powders or solid dispersions.

Currently, the main problem in boosting saturation has been that where free API concentrations rise above equilibrium solubility this leads to drug precipitation or crystallization. The inventors have found a formulation which is substantially amorphous and prevents said crystallization. In effect, this formulation demonstrated higher levels of API supersaturation and maintained these higher supersaturation levels for prolonged periods. Considering the high number of poorly water-soluble API in contemporary drug discovery pipelines, the concept of supersaturation may serve as an effective formulation approach for enhancing bioavailability. The formulation is intended to yield significantly high gastrointestinal concentrations of the API by achieving a state of supersaturation and further also maintaining said supersaturation state for a prolonged period. This way the state of supersaturation may enhance the intestinal absorption of the API, which can subsequently bring about an improved bioavailability of said API. This supersaturation effect may be further steered through customized (i.e. improved or selective) dissolution rates and/or levels as described below. Moreover, the formulation is intended to yield said high API concentrations in physiological media in order to achieve effective clinical performance of injectable formulations of the drug. Indeed, since the formulation might be comprised solely of non-allergic protein excipient and API, surfactants and other potentially allergic and/or toxic excipients are avoided leading to a safer product having reduced allergic potential and other side effects.

As used herein the term "supersaturation" generally refers to a state of a solution that contains more of the dissolved material than could be dissolved by the solvent under normal circumstances. Specifically for the present invention the state of supersaturation refers a state wherein the formulation dissolves more absorbable material, i.e. the API, than could be dissolved under normal circumstances, i.e. without the excipient as described by the present invention, preferably in the gastrointestinal area and/or in physiological media of use as injectable. As used herein the term "bioavailability" generally refers to the administered dose of the unchanged API that reaches the systemic circulation; commonly being exposed to digestions and absorption in the gastrointestinal area. Thus for a formulation the bioavailability indicates the systemically available fraction of the API. By definition, when an API is administered intravenously, its bioavailability is 100%. The bioavailability for orally administered API, however, depends various biological and chemicals factors, most notably the solubility and intake rate. The bioavailability for orally administered API can be measured experimentally (e.g., in-vivo) and is typically known in the art for most of APIs. An API is considered to have a 'high bioavailability' when more than 80% of the administered dose of the unchanged API reaches the systemic circulation; and a 'poor bioavailability' when less than 50% of the administered dose of the unchanged API reaches the systemic circulation; and 'very poor bioavailability' when less than 25% reaches the systemic circulation. Detailed technical information (e.g. protocols and equipment) on determining the API's bioavailability may be found in the CDER waiver on API classes.

In some embodiments the API is a class I API In some preferred embodiments the API is a class II API. In some other embodiments the API is a class III API. In some other preferred embodiments the API is a class IV API. For the API classes which are inherently well dissolving (e.g. Class I and Class III), it is usually unnecessary to combine them with a solubility enhancer such as an excipient. Although it is noted that certain well dissolving API would still benefit from an even more improved solubility as this could further improve the bioavailability of the API, such as API that show a borderline solubility or a solubility dependent on the pH. For example, Ibuprofen shows high solubility at pH 6.8 but a low solubility at pH 4.5; depending on the dosage form it could thus still benefit from a solubility enhancer. However; the classes that will likely benefit the most from solubility enhancing effects of an excipient are those showing an inherently low solubility (e.g. Class II and Class IV). This is particularly important for Class II APIs because a direct correlation between their (in-vitro) solvation and its (in-vivo) bioavailability has been scientifically documented. Additionally, resulting from improvements in solubility and/or bioavailability, other benefits may also be anticipated. For instance, it could be possible to produce dosage forms containing lower API concentrations because less of the API will be required to achieve the dissolution levels necessary for proper intake by the intestinal mucosa. Additionally, certain APIs which were previously deemed as not orally administrable may be reconsidered at least for commercial purposes. Moreover, in case the protein excipient is made from human serum albumin (HSA), the said improvements in solubility may yield high API concentrations in physiological media in order to achieve effective clinical performance of injectable formulations of either BCS Class II or IV drugs. Indeed, since said formulation is solely comprised of non-allergic protein excipient and API, surfactants and other potentially allergic and/or toxic excipients are avoided leading to a safer product having reduced allergic potential and other side effects.

In a most preferred embodiment the formulation comprises: a protein based excipient obtained from a protein composition or a hydrolysate thereof which comprises proteins—as per monomer—of at least 20 amino acids in length; and a Class II active pharmaceutical ingredient (API); characterized therein that said protein based excipient and said API are both substantially amorphous.

In another most preferred embodiment the formulation comprises: a protein based excipient obtained from a protein composition or a hydrolysate thereof which comprises proteins—as per monomer—of at least 20 amino acids in length; and a Class IV active pharmaceutical ingredient (API); characterized therein that said protein based excipient and said API are both substantially amorphous. Advantageously, the protein—as per monomer—is at least 50 amino acids in length; more preferably at least 100 amino acids in length; most preferably at least 250 amino acids in length, for example at least 300 amino acids or at least 500 amino acids. Generally the formulation according to the present invention exhibits at least one of the following measurable improvements compared to a control formulation comprising the API without the protein based excipient as described by the present invention: (a) an increase in maximum API concentration of at least about 25%; (b) an increase in the dissolution rate of at least about 25%; (c) an increase of the time period for which a state of supersaturation is achieved and maintained for at least about 25%; (d) an increase in bioavailability of the API of at least about 25%. The experimental data to support said improvements is presented in the examples.

In a particular embodiment of the present invention the protein-based excipient is characterized in that said excipient is obtained through dissolving or solubilizing a protein composition or a hydrolysate thereof in a solvent to obtain a protein solution and drying said protein solution to obtain the excipient. Essentially the excipient according to a particular embodiment of the invention is a protein-based excipient comprising a naturally occurring protein from a (biologically) natural source; for example of animal, natural (i.e., vegetable) and/or microbial origin. In another particular embodiment of the invention the protein-based excipient is derived from improved or modified recombinant proteins. In another particular embodiment of the invention the protein-based excipient is derived from artificial (mimicking) proteins or scaffolds. For the purposes of the invention the term protein based excipient may be a naturally occurring, recombinant, artificial protein, and/or a combination thereof.

In a further aspect the present invention relates to an API which is substantially amorphous, characterized in that said API is obtained through dissolving or solubilizing an API in a solvent to obtain an API solution and drying said API solution to obtain the API which is substantially amorphous. In some particular embodiments the API according to the present invention is substantially amorphous, more in particular almost completely amorphous, and preferably in particular completely amorphous.

The inventors have observed that the excipient according to the present invention combined with an API forms a stable, amorphous formulation following the drying of the solution comprising said excipient, an API and a solvent. This formulation attains solubility, dissolution rates and levels, supersaturation and/or bioavailability above that achieved using traditional (e.g. hydrophilic polymer) excipients (confirmed experimentally).

In particular embodiments the formulation according to the present invention is characterized in that the protein based excipient is obtained through dissolving or solubilizing a protein composition or a hydrolysate thereof in a solvent to obtain a protein solution and drying said protein solution to obtain a protein based excipient, and further characterized in that the amorphous API is obtained through dissolving or solubilizing a API in a solvent, similar or different from the solvent used for the protein solution, to obtain an API solution and drying said API solution to obtain an API which is substantially amorphous, preferably completely amorphous, and further combining said dried excipient and said dried API to obtain a formulation which is substantially amorphous, preferably completely amorphous, according to an embodiment of the invention.

Alternatively, in some other embodiments the formulation is characterized in that the formulation is obtained through dissolving or solubilizing a protein composition or a hydrolysate thereof together with an API in a common solvent and drying said protein-API solution to obtain a formulation which is substantially amorphous, preferably completely amorphous, according to an embodiment of the invention.

Alternatively, in some other embodiments the formulation is characterized in that the formulation is obtained through dissolving or solubilizing an API in a solvent and drying said API solution to obtain an API which is substantially amorphous, and further combining said dried API with a provided protein based excipient which is preferably substantially not denaturized, preferably completely not denaturized, to obtain a formulation which is substantially amorphous, preferably completely not amorphous, according to an embodiment of the invention.

As used herein the term "protein composition" generally refers to a mixture comprising similar proteins from a similar source, similar proteins from different sources, different proteins from a similar source, or different proteins from different source. For the purposes of the present invention the protein composition refers to a mixture of different proteins or hydrolysates thereof.

The term "solvent" generally refers to a substance (liquid, solid or gas) that dissolves a solute (i.e. a substance which is chemically different from the solvent) to result in a solution. For the purposes of the present invention the solvent is usually a liquid wherein a solid (e.g. protein composition or hydrolysate thereof, and/or an API) is dissolved.

In a particular embodiment the solvent is an organic acid or is a mixture that comprises an organic acid, preferably the organic acid is chosen from formic acid, trifluoroacetic acid, or acetic acid. This particular embodiment is particularly well suited for spray drying of a solution comprising a solution comprising a formulation according to an embodiment of the present invention.

In another particular embodiment the solvent is an organosulfur compound or is a mixture that comprises an organosulfur compound, preferably the organosulfur compound is dimethyl sulfoxide (DMSO). This particular embodiment is particularly well suited for freeze drying of a solution comprising a formulation according to an embodiment of the present invention.

Additionally, the above mixtures comprising an organic acid and/or an organosulfur compound may further comprise one or more (traditional) solvents; examples of traditional solvents suitable for the present invention include alcohols (e.g. methanol, ethanol), acetone, DCM, THF, methylene chloride, methyl ethyl ketone, acetonitrile, or polyethylene glycols.

After extraction from a biological source most protein compositions are amorphous. However, during processing the protein composition are exposed to solvent, such as organic acids, which commonly denature the proteins, i.e., the process in which proteins or nucleic acids lose the quaternary structure, tertiary structure and/or secondary structure which is present in their native state. Since their biological activity (i.e. the interaction with foreign molecules, such as the API) of the proteins relies on the fully folded structure of the protein molecule, it is commonly assumed that this denaturation process will reduce the proteins to a biologically inactive state. In particular, the formulation as disclosed herein provides that the protein based excipient is substantially not denaturized and/or retains at least part of its biological activity.

As used herein the term "denaturation" generally refers to the process in which proteins or nucleic acids lose the quaternary, tertiary and/or secondary structure which is present in their native state, by application of some external stress (e.g. temperature, radiation, etc.) or compounds (e.g. a strong acid or base, a concentrated inorganic salt, certain organic solvents, etc.). Often if proteins are denatured, this results in a reduction or disruption of their biological activity. For the purposes of the present invention, a protein is referred to as 'substantially not denaturized' when it contains almost no traces of denaturation, i.e. less than 10%, preferably less than 5%; and it is referred to as 'completely not denaturized' when it contains no traces of denaturation, i.e. less than 5%, preferably less than 3%, most preferably less than 1%. The denaturation state can be verified experimentally (e.g., dual-polarization interferometry, circular dichroism, quartz crystal microbalance) for most proteins either directly or through associated loss of biological activity.

In some embodiments of the present invention the excipient is substantially not denaturized. In some embodiments of the present invention the excipient is completely not denaturized.

In some other embodiments of the present invention the excipient retains at least part of its biological activity. In some other embodiments of the present invention the excipient retains substantially its biological activity. In some other embodiments of the present invention the excipient retains almost completely its biological activity. In some other preferred embodiments of the present invention the excipient retains completely its biological activity. For the purposes of the present invention, a protein's biological activity is referred to as 'partially retained' when it displays a measurable technical effect of its full biological activity (=100%) as measured in vivo, i.e. at least 10%, preferably at least 20%, more preferably at least 30%, most preferably at least 40%; it is referred to as 'substantially retained' when it displays a significantly measurable technical effect of its full biological activity (=100%), i.e. at least 50%, preferably at least 60%, more preferably at least 70%, most preferably at least 80%; it is referred to as 'almost completely retained' when it displays almost all of its biological activity (=100%), i.e. at least 90%, preferably at least 92%, most preferably at least 94%; it is referred to as 'completely retained' when it displays all of its biological activity (=100%), i.e. at least 95%, preferably at least 98%, more preferably at least 99%, most preferably 100%.

The inventors have observed that the protein based excipient may biologically interact with the API to keep it in solution and/or supersaturation. A proteins' biological activity is associated with the secondary, tertiary and quaternary structure of said protein; thus denaturation can be linked with a reduction or loss of biological activity. The inventors have thus found that by retaining the biological activity of the proteins comprising the protein based excipient, the formulation comprising said protein based excipient may exhibit various benefits over traditional (polymer) excipient according to the state of art. The benefits may include enhanced solubility, dissolution rate and/or levels, achieving a state of supersaturation, maintaining said state of supersaturation over a prolonged time period (confirmed experimentally). As a consequence, the formulation may further enhance the gastrointestinal absorption of the API, which can subsequently bring about an improved bioavailability of said API. Moreover, in case the protein excipient is made from human serum albumin (HSA), the said benefits may yield high API concentrations in physiological media in order to achieve effective clinical performance of injectable formulations of the drug. Indeed, since said formulation is solely comprised of non-allergic protein excipient and API, surfactants and other potentially allergic and/or toxic excipients are avoided leading to a safer product having reduced allergic potential and other side effects.

In particular, the formulation as disclosed herein provides that at least one protein of the protein composition or a hydrolysate thereof is chosen from soy protein, pea protein, blood proteins, Immunoglobulins, milk proteins, gelatine, keratin, corn, wheat, hemp, rye, oats, peanut, barley, casein, albumin, whey protein (lactalbumin), Hydrolysed Whey Protein Isolate (HWPI), hydrolyzed collagen, plasma proteins, serum albumin, bovine serum albumin (BSA), human serum albumin (HSA), egg albumin, fish albumin, elastin, collagen, recombinant or artificial proteins, recombinant versions of natural or artificial binding scaffolds, and/or a combination thereof; preferably HSA, BSA, gelatine and/or a combination thereof. The former list comprises proteins obtained via one or more extraction methods from a naturally occurring source, otherwise known as 'natural proteins'. The former list also comprises variants that are optimized using recombination technology, otherwise known as 'recombinant proteins'; the recombinant proteins may have been modified using different pre- or post-processing methods to alter or improve their physical, biological and/or chemical properties in comparison with the naturally occurring variant (e.g. antibodies, nanobodies, etc.). The former list also comprises variants that are produced to mimic the functionality of a naturally occurring or recombinant variant, known as protein mimetics; examples include artificial binding scaffolds (Alphabodies™, Affimers, etc.). Accordingly, for the purposes of the invention no distinction is made based on the origin of the protein; that is, the term 'proteins' refers equally to naturally occurring, recombinant or artificial proteins, unless stated otherwise. Additionally, the combination of the protein composition or a hydrolysate thereof as may be a combination regardless of the type or origin of the protein; for example, a combination of native proteins, recombinant proteins and/or artificial proteins; for example a combination of only naturally occurring BSA or gelatin.

In an embodiment of the present invention, the excipient according to the present invention is prepared from a protein composition or a hydrolysate thereof extracted from animal sources (i.e. naturally occurring proteins), in particular chosen from acid porcine, alkaline bovine, bovine hides, soda hides, acid pig skins, acid pig bones, lime bovine bones, acid bovine bones, acid bovine hides, lime pig bones, fish, or a combination thereof. For extracted gelatin the protein is further graded by bloom, which is a measure of the stiffness and strength of the gelatin. The value represents the weight (in grams) needed by a probe to deflect the surface of the gel 4 mm without breaking it, which typically lies between 30 and 300 gr Bloom. For the purposes of the invention different bloom values may be used; preferably Bloom values above 200 gr are used.

In general proteins compositions comprising proteins with a length below 10 amino acids require no solvent and can be easily dissolved in aqueous media. Additionally, the inventors have observed that protein excipients comprising a protein composition or hydrolysate thereof with a length above 100 amino acid (e.g. BSA and gelatin), may show additional beneficial biological activity in combination with certain API. Thus formulations comprising a protein excipient comprising a protein composition or hydrolysate thereof with a length above 100 amino acids may have a further enhanced solubility, dissolution rate and/or levels, achieving a state of supersaturation, maintaining said state of supersaturation over a prolonged time period (confirmed experimentally). As a consequence, the formulation may further enhance the gastrointestinal absorption of the API, which can subsequently bring about an improved bioavailability of said API, or may create the desired level of super saturation in physiological media in order to achieve effective clinical performance of injectable formulations of the drug As first reference, the full-length BSA precursor protein is 607 amino acids in length, which weighs 69324 Dalton (Da). The full-length of a mature BSA protein is 583 amino acids and weighs 66463 Da. In some embodiments the BSA protein may be cleaved to obtain shorter amino acid length, wherein BSA still retains its biological activity for the purposes of the present invention. Additionally, BSA can have its amino acid sequence modified (e.g. recombined) to, for example, further improve saturation values; thus formulations using said recombinant BSA may even obtain a higher degree of supersaturation and bioavailability compared to formulations using only native BSA.

As second reference, the helical part of fibrous collagens, homo- or heterotrimers in their native states, generally contains about 1000 amino acids per chain, which adds up to about 3000 amino acids for a well-folded molecule, weighing more than 300 kDa because of a significant amount of posttranslational modifications. In the manufacturing of gelatin, treatment of the animal raw material with dilute acid (type A process) or alkali (type B process) results in partial cleavage of the interchain cross-links that define the thermal tolerance of collagen fibrils. The structure is broken down to such an extent that "hot water-soluble collagen", i.e. gelatin, is formed. In the subsequent extraction step, hot water melts out the collagen fibrils into their constituent individual chains, at the same time serving as the solvent. Gelatin therefore is a polydisperse mixture of protein fragments of varying molecular masses, ranging from 15 to more than 400 kDa, depending on the level of chemical/thermal hydrolysis of the polypeptide chains and the level of interchain cross-link hydrolysis. Dissolution of dried gelatin in formic acid does not change its molecular weight profile over days, and upon evaporation of the formic acid solvent, the gelatin retains its gelling/melting properties of the original product. In particular, the formulation as disclosed herein provides that the API exhibits a low solubility, dissolution rate or level, supersaturation state and/or bioavailability.

As previously defined, the term "solubility" generally refers to a quantitative term related to the property of a solid, liquid, or gaseous chemical substance called solute to dissolve in a solid, liquid, or gaseous solvent. The solubility is expressed in terms of the 'dissolution level, which expresses the amount of said substance that will dissolve in a given amount of solvent. In general, if more than 0.1 g of that substance dissolves in 100 mL solvent the substance is said to be soluble; if less than 0.1 g dissolves in 100 mL solvent, the substance is said to be insoluble or, more exactly, sparingly soluble. The solubility may be measured experimentally and is known in the art. Explanation on how the solubility of the present invention was determined is presented further in the examples of this description. A correlated term is the 'dissolution rate', which expresses the solubility measured against the time period wherein said substance will dissolve in a given amount of solvent. In general very soluble substance also exhibit a high dissolution rate, although in certain substances may have a high dissolution level and yet dissolve very slowly. Selective adaptations to the dissolution level and rate may have secondary benefits towards a formulation's functionality and its pharmacokinetic properties.

The inventors have observed that the excipient according to the present invention is a stable, powder following the drying of the solution comprising said protein composition or a hydrolysate thereof and a solvent, preferably an organic acid. This protein based excipient attains solubility and dissolution rates above those achieved by traditional (e.g. polymer) excipients (confirmed experimentally). Therefore, formulations were devised to make use of said solubility and dissolution rate enhancing properties.

In particular, the formulation as disclosed herein provides that the API is selected from the following list: Flubendazole, Carbamazepine, Griseofulvin, Phenytoin, Nifedipine, Verapamil, Azithromycin, Nitrofurantoin, lopanoic acid, Itraconazole, Ibuprofen, Indomethacin, Glibenclamide, Bicalutamide, Ezetimibe, Aceclofenac, Ketoconazole, Oxfendazole, Ritonavir, Saquinavir, Fenofibrate, Cinnarizin, Darunavir, Diazepam, Bifonazole, Testosterone undecanoate, or Naproxen; more in particular from the following list: Flubendazole, Ibuprofen, Indomethacin, Ritonavir, Naproxen, Phenytoin, Nifedipine, Vemurafenib, Griseofulvin, Itraconazole, or Verapamil.

For the purposes of the invention the API may be selected from any API category. However, preferably the API exhibits a low solubility, dissolution rate and/or bioavailability; thus fully benefitting from the solubility, dissolution rate and level, supersaturation and/or bioavailability enhancing effects of said formulation to enable or improve the active properties of said API. In a particular embodiment of the present invention, said formulation comprises an API chosen from Flubendazole, Carbamazepine, Griseofulvin, Phenytoin, Nifedipine, Verapamil, Azithromycin, Nitrofurantoin, lopanoic acid, Itraconazole, Ibuprofen, Indomethacin, Glibenclamide, Bicalutamide, Ezetimibe, Aceclofenac, Ketoconazole, Oxfendazole, Ritonavir, Saquinavir, Fenofibrate, Cinnarizin, Darunavir, Diazepam, Bifonazole, Testosterone undecanoate, or Naproxen; preferably Flubendazole, Ibuprofen, Indomethacin, Ritonavir, Naproxen, Phenytoin, Nifedipine, Vemurafenib, Griseofulvin, Itraconazole, or Verapamil; most preferably Flubendazole.

The inventors have observed that the excipient according to the present invention combined with an API form a stable, amorphous formulation following the drying the solution comprising said excipient, an API and an acid. This process results in a formulation which attains solubility and dissolution rates above those achieved using traditional polymer excipients (confirmed experimentally).

Often, such a crystalline state exhibits very poor solubility and dissolution rates, requiring the use of multiple solvents or a high temperature to dissolve into a solution. By dissolving a crystalline protein composition in an acid solvent (e.g. formic acid, trifluoroacetic acid, acetic acid) the protein composition is transformed into a substantially amorphous state; said acid solvents are also capable of breaking protein-protein interactions which cannot be broken using a neutral solvent (e.g. $H_2O$). Commonly such an amorphous state exhibits an improved solubility and dissolution rates over the crystalline states. In certain cases the protein composition in an amorphous state becomes completely dissolvable even at low temperatures.

In a preferred embodiment the formulation is produced by dissolving a protein based composition or hydrolysate and an API in a solvent chosen from the following list: formic acid, acetic acid, DMSO, and/or glycerol; or a solvent mixture comprising at least one solvent chosen from the following list: formic acid, acetic acid, DMSO, and/or glycerol, and optionally, at least one (traditional) solvent chosen from the following list: alcohol, acetone, DCM, THF, methylene chloride, methyl ethyl ketone, acetonitrile, or polyethylene glycols. Formic acid and acetic acid are organic solvent; proteins typically do not dissolve (properly) in organic solvents and thus traditional solvents were used instead. Examples of traditional solvents include: alcohol, acetone, DCM, THF, methylene chloride, methyl ethyl ketone, acetonitrile, or polyethylene glycols.

However, the inventors have found that formic acid, acetic acid, DMSO, or glycerol can be used to dissolve proteins; similar observations were made for solvent mixture comprising at least formic acid, acetic acid, DMSO, and/or glycerol. Formic acid and acetic acid are found to be particularly suitable for use as solvent when producing the formulation via spray drying: while DMSO is found particularly suitable for use as solvent when producing the formulation via freeze drying. Additionally, a solvent mixture was found.

Additionally, when a formulation comprising an API and a protein composition or hydrolysate thereof is produced by first dissolving the ingredients with traditional solvents, such as alcohols (e.g. methanol, ethanol) or acetone, followed by drying said solution to form a dry formulation (e.g. solid dispersion), a too high concentration of a protein composition or hydrolysate thereof may cause a hydrolysis of the API. Additionally, certain API may simply not dissolve at all in traditional solvent; for example, Vemurafenib does not dissolve in methanol. As a result, only formulations comprising low concentrations (e.g. below 10% excipient concentration) of a protein composition or hydrolysate thereof may be successfully combined with an API without adversely affecting the API's properties. However, it was found that when an API is dissolved in an organic acid, in particular formic acid, trifluoroacetic acid, or acetic acid, the API hydrolysis may be avoided. Additionally, the organic acid allows a full solution of most (poorly soluble) API. As a result a production of dry formulations comprising a high concentration of protein composition or hydrolysate (e.g. above 50 excipient concentration) may be made possible; particularly so for the production of solid dispersions.

Additionally or alternatively, a mixture comprising a traditional solvent (e.g. alcohols such as methanol or ethanol, acetone, DCM, THF, methylene chloride, methyl ethyl ketone, acetonitrile, DMSO, polyethylene glycols) and an organic acid (e.g. formic acid, trifluoroacetic acid, acetic acid) can also be considered because the addition of the traditional solvent might have an influence on the evaporation properties (lower boiling point, lower heat of evapora-
tion, higher vapor pressure, etc) and might also improve the
solubility of the API in the organic acid.

The downside of pure organic acids is a typically high
boiling point, for instance 100.8° C. for formic acid in
comparison with 65° C. for methanol. As such, more energy
and/or a longer drying time are required to achieve a
complete evaporation of the solvent. By using a mixture as
solvent the boiling point can be lowered while maintaining
at least partially the above discussed benefits of the organic
acid.

In some particular embodiments the solvent is a solvent
mixture comprising at least 5% of organic acid to at most
100% organic acid (v/v); preferably 10% to 90% organic
acid; more preferably 15% to 90% organic acid; most
preferably 20% to 90% organic acid; most preferably 30%
to 70% organic acid; most preferably 40% to 60% organic
acid; most preferably 45% to 55% organic acid, for example
50% organic acid.

In some particularly preferred embodiments the solvent is
a solvent mixture comprising acetic acid and/or formic acid
in an amount of at least 5% to at most 90% (v/v); preferably
10% to 90% acetic acid and/or formic acid; more preferably
15% to 90% acetic acid and/or formic acid; most preferably
20% to 90% acetic acid and/or formic acid; most preferably
30% to 70% acetic acid and/or formic acid; most preferably
40% to 60% acetic acid and/or formic acid; most preferably
45% to 55% acetic acid and/or formic acid, for example 50%
acetic acid; for example 52% formic acid.

A full dissolution of proteins (without precipitation) is
achieved when a solvent mixture comprises at least 5% (v/v)
concentration of an organic acid, in particular at least 5%
(v/v) of formic acid or acetic acid; preferably comprises at
least 10% (v/v) concentration of an organic acid, in particu-
lar at least 10% (v/v) of formic acid or acetic acid; more
preferably comprises at least 15% (v/v) concentration of an
organic acid, in particular at least 15% (v/v) of formic acid
or acetic acid; most preferably comprises at least 20% (v/v)
concentration of an organic acid, for example 30% (v/v) of
formic acid; for example 40% (v/v) of acetic acid. The exact
minimal amount depends on the protein composition, for
instance, some proteins may require at least 5% (v/v) of
formic acid or acetic acid, while other may require 15%
(v/v) of formic acid or acetic acid. However, the inventors
found that an amount of at least 20% (v/v) of formic acid or
acetic acid is suitable for dissolving the commonly used
proteins (as listed herein); in particular wherein the protein
is albumin (BSA, HAS) or gelatin.

In some embodiments the solvent is a solvent mixture
comprising dimethyl sulfoxide (DMSO) in an amount of at
least 5% to at most 90% (v/v); preferably 10% to 90%
DMSO; more preferably 15% to 90% DMSO; most prefer-
ably 20% to 90% DMSO; most preferably 30% to 70%
DMSO; most preferably 40% to 60% DMSO; most prefer-
ably 45% to 55% DMSO, for example 50% DMSO.

In some embodiments the solvent is a solvent mixture
comprising at least one organic acid, preferably chosen from
acetic acid and/or formic acid, in an amount between at least
5% to at most 80% and at least one traditional solvent,
preferably chosen from alcohol, acetone, DCM, THF, meth-
ylene chloride, methyl ethyl ketone, acetonitrile, DMSO,
and/or polyethylene glycols, in an amount of at least 20% to
at most 95%, in which 100% (v/v) is the total amount of
listed solvents in the mixture; preferably 10% to 80% of an
organic acid and 20% to 90% of a traditional solvent;
preferably 15% to 80% of an organic acid and 20% to 85%
of a traditional solvent; preferably 20% to 80% of an organic acid and 20% to 80% of a traditional solvent; preferably
30% to 70% of an organic acid and 30% to 70% of a
traditional solvent; more preferably 40% to 60% of an
organic acid and 40% to 60% of a traditional solvent; most
preferably 45% to 55% of an organic acid and 45% to 55%
of a traditional solvent.

In some embodiments the solvent is a solvent mixture
comprising at least one organosulfur compound, preferably
dimethyl sulfoxide (DMSO), in an amount between at least
5% to at most 80% and at least one traditional solvent,
preferably chosen from alcohol, acetone, DCM, THF, meth-
ylene chloride, methyl ethyl ketone, acetonitrile, DMSO,
and/or polyethylene glycols, in an amount of at least 20% to
at most 95%, in which 100% (v/v) is the total amount of
listed solvents in the mixture; preferably 10% to 80% of an
organosulfur compound and 20% to 90% of a traditional
solvent; preferably 15% to 80% of an organosulfur com-
pound and 20% to 85% of a traditional solvent; preferably
20% to 80% of an organosulfur compound and 20% to 80%
of a traditional solvent; preferably 30% to 70% of an
organosulfur compound and 30% to 70% of a traditional
solvent; more preferably 40% to 60% of an organosulfur
compound and 40% to 60% of a traditional solvent; most
preferably 45% to 55% of an organosulfur compound and
45% to 55% of a traditional solvent.

In some preferred embodiments the solvent is a solvent
mixture comprising formic acid in an amount between at
least 20% to at most 80%, and at least one traditional
solvent, preferably chosen from alcohol, acetone, DCM,
THF, methylene chloride, methyl ethyl ketone, acetonitrile,
DMSO, and/or polyethylene glycols, in an amount of at least
20% to at most 80%, in which 100% (v/v) is the total amount
of listed solvents in the mixture; preferably 30% to 70%
formic acid and 30% to 70% of at least one traditional
solvent; more preferably 40% to 60% formic acid and 40%
to 60% at least one traditional solvent; most preferably 45%
to 55% formic acid and 45% to 55% of at least one
traditional solvent; for example 50% formic acid and 50% of
alcohol. A mixture comprising at least 20% (v/v) concen-
tration of formic acid allows for a full dissolution of proteins
(without precipitation).

In some preferred embodiments the solvent is a solvent
mixture comprising acetic acid in an amount between at
least 20% to at most 80%, and at least one traditional
solvent, preferably chosen from alcohol, acetone, DCM,
THF, methylene chloride, methyl ethyl ketone, acetonitrile,
DMSO, and/or polyethylene glycols, in an amount of at least
20% to at most 80%, in which 100% (v/v) is the total amount
of listed solvents in the mixture; preferably 30% to 70%
acetic acid and 30% to 70% of at least one traditional
solvent; more preferably 40% to 60% acetic acid and 40%
to 60% at least one traditional solvent; most preferably 45%
to 55% acetic acid and 45% to 55% of at least one traditional
solvent; for example 50% acetic acid and 50% of alcohol. A
mixture comprising at least 20% (v/v) concentration of
acetic acid allows for a full dissolution of proteins (without
precipitation).

In some particular embodiments the solvent is a binary
solvent mixture, comprising one organic acid, preferably
chosen from acetic acid or formic acid, and one other
(traditional) solvent, preferably chosen from alcohol,
acetone, DCM, THF, methylene chloride, methyl ethyl
ketone, acetonitrile, DMSO, or polyethylene glycols. The
binary mixture comprising at least 5%, preferably at least
10%, more preferably at least 15%, most preferably at least
20% (v/v) concentration of formic acid or acetic acid allows for a full dissolution of proteins (without precipitation); in particular wherein the protein is albumin (BSA, HAS) or gelatin.

In some particularly preferred embodiments the binary mixture comprises acetic acid or formic acid in an amount between at least 5% to at most 90%, and one traditional solvent, preferably chosen from alcohol, acetone, DCM, THF, methylene chloride, methyl ethyl ketone, acetonitrile, DMSO, and/or polyethylene glycols, in an amount between at least 10 to at most 95%; in which 100% (v/v/v) is the total amount of listed solvents in the mixture; preferably 20% to 90% of formic acid or acetic acid, and 10% to 80 of one traditional solvent; preferably 10% to 80% of formic acid or acetic acid, and 30% to 90 of one traditional solvent; more preferably 15% to 60% of formic acid or acetic acid, and 40% to 85 of one traditional solvent; for example 40% of acetic acid, 30% of alcohol and 30% of acetone; most preferably 20% to 50% of formic acid or acetic acid, and 50% to 80 of one traditional solvent; for example 40% of acetic acid and 60% alcohol; for example 50% of formic acid and 50% of acetone.

In some other particularly preferred embodiments the solvent is a binary solvent mixture comprising acetic acid in an amount between at least 20% to at most 80% and a traditional solvent, preferably chosen from an alcohol, acetone, DCM, THF, methylene chloride, methyl ethyl ketone, acetonitrile, DMSO, or polyethylene glycol, in an amount of at most 80% to at least 20%, in which 100% (v/v) is the total amount of listed solvents in the mixture; preferably 30% to 70% acetic acid and 70% to 30% of an alcohol or acetone; more preferably 40% to 60% acetic acid and 60% to 40% of an alcohol or acetone; most preferably 45% to 55% acetic acid and 55% to 45% of an alcohol or acetone; for example 45% acetic acid and 55% of an alcohol; for example 50% acetic acid and 50% of acetone. A binary mixture comprising at least 20% (v/v) concentration of acetic acid allows for a full dissolution of proteins (without precipitation); in particular wherein the protein is albumin (BSA, HAS) or gelatin.

In some other particular preferred embodiments the solvent is a binary solvent mixture comprising formic acid in an amount between at least 20% to at most 80%, and traditional solvent, preferably chosen from an alcohol, acetone, DCM, THF, methylene chloride, methyl ethyl ketone, acetonitrile, DMSO, or polyethylene glycol, in an amount of at most 80% to at least 20%, in which 100% (v/v) is the total amount of listed solvents in the mixture; preferably 30% to 70% formic acid and 70% to 30% of an alcohol or acetone; more preferably 40% to 60% formic acid and 60% to 40% of an alcohol or acetone; most preferably 45% to 55% formic acid and 55% to 45% of an alcohol or acetone. A binary mixture comprising at least 20% (v/v) concentration of formic acid allows for a full dissolution of proteins (without precipitation); in particular wherein the protein is albumin (BSA, HAS) or gelatin.

In some particular embodiments the solvent is a binary solvent mixture, comprising one organosulfur compound, preferably DMSO, and one other (traditional) solvent, preferably chosen from alcohol, acetone, DCM, THF, methylene chloride, methyl ethyl ketone, acetonitrile, DMSO, or polyethylene glycols. The binary mixture comprising at least 5%, preferably at least 10%, more preferably at least 15%, most preferably at least 20% (v/v) concentration of DMSO allows for a full dissolution of proteins (without precipitation); in particular wherein the protein is albumin (BSA, HAS) or gelatin.

In some particularly preferred embodiments the binary mixture comprises DMSO in an amount between at least 5% to at most 80%, and one traditional solvent, preferably chosen from alcohol, acetone, DCM, THF, methylene chloride, methyl ethyl ketone, acetonitrile, DMSO, and/or polyethylene glycols, in an amount between at least 20 to at most 95%; in which 100% (v/v/v) is the total amount of listed solvents in the mixture; preferably 10% to 70% of DMSO, and 30% to 90 of one traditional solvent; more preferably 15% to 60% of DMSO, and 40% to 85 of one traditional solvent; for example 40% of acetic acid, 30% of alcohol and 30% of acetone; most preferably 20% to 50% of DMSO, and 50% to 80 of one traditional solvent; for example 40% of DMSO and 60% alcohol; for example 50% of DMSO and 50% of acetone.

In some particular embodiments the solvent is a ternary solvent mixture, comprising one organic acid, preferably chosen from acetic acid or formic acid, and two other (traditional) solvents, preferably chosen from alcohol, acetone, DCM, THF, methylene chloride, methyl ethyl ketone, acetonitrile, DMSO, and/or polyethylene glycols In some particularly preferred embodiments the solvent is a ternary solvent mixture comprising one organic acid, preferably chosen from acetic acid or formic acid in an amount between at least 5% to at most 80%, and two other (traditional) solvents, preferably chosen from alcohol, acetone, DCM, THF, methylene chloride, methyl ethyl ketone, acetonitrile, DMSO, and/or polyethylene glycols, in an amount between at least 20 to at most 95%; in which 100% (v/v/v) is the total amount of listed solvents in the mixture; preferably 10% to 70% of formic acid or acetic acid, and 30% to 90 of two traditional solvents; more preferably 15% to 60% of formic acid or acetic acid, and 40% to 85 of two traditional solvents; for example 40% of acetic acid, 30% of alcohol and 30% of acetone; most preferably 20% to 50% of formic acid or acetic acid, and 50% to 80 of two traditional solvents; for example 40% of acetic acid, 30% of ethanol and 30% of acetone; for example 50% of formic acid, 25% of methanol and 30% of DCM. In some other particular embodiments the solvent is a ternary solvent mixture, comprising two organic acids, preferably at least one chosen from acetic acid or formic acid, more preferably are acetic acid and formic acid, and one other (traditional) solvent, preferably chosen from alcohol, acetone, DCM, THF, methylene chloride, methyl ethyl ketone, acetonitrile, and/or polyethylene glycols.

In some particularly preferred embodiments the solvent is a ternary solvent mixture comprising two organic acids, preferably chosen from acetic acid and/or formic acid, more preferably are acetic acid and formic acid, in an amount between at least 5% to at most 80%, and one other (traditional) solvents, preferably chosen from alcohol, acetone, DCM, THF, methylene chloride, methyl ethyl ketone, acetonitrile, DMSO, and/or polyethylene glycols, in an amount between at least 20 to at most 95%; in which 100% (v/v/v) is the total amount of listed solvents in the mixture; preferably 10% to 70% of formic acid and acetic acid, and 30% to 90 of two traditional solvents; more preferably 15% to 60% of formic acid and acetic acid, and 40% to 85 of two traditional solvents; for example 40% of acetic acid, 30% of alcohol and 30% of acetone; most preferably 20% to 50% of formic acid or acetic acid, and 50% to 80 of two traditional solvents; for example 40% of acetic acid, 30% of ethanol and 30% of acetone; for example 50% of formic acid, 25% of methanol and 30% of DCM.

In some particularly preferred embodiments the ternary mixture comprises acetic acid in an amount between at least 5% to at most 70%, formic acid in an amount between at least 5% to at most 70%, and two other (traditional) solvents, preferably chosen from alcohol, acetone, DCM, THF, methylene chloride, methyl ethyl ketone, acetonitrile, and/or polyethylene glycols in an amount between at least 25% to at most 90%; in which 100% (v/v/v) is the total amount of listed solvents in the mixture; preferably 10% to 60% of formic acid, 10% to 60% of acetic acid, and 30% to 80% of two other (traditional) solvents; more preferably 15% to 60% of formic acid, 15% to 60% of acetic acid, and 25% to 70% of two other (traditional) solvents; most preferably 20% to 50% of formic acid, 20% to 50% of acetic acid, and 30% to 60% of two other (traditional) solvents; such as 25% formic acid, 25% acetic acid, and 50% of two other (traditional) solvents; such as 50% formic acid, 25% acetic acid, and 25% of two other (traditional) solvents; such as 25% formic acid, 50% acetic acid, and 25% of two other (traditional) solvents.

In some other particular embodiments the solvent is a ternary solvent mixture, comprising one organosulfur compound, preferably dimethyl sulfoxide (DMSO), in an amount between at least 5% to at most 80%, and two other (traditional) solvents, preferably chosen from alcohol, acetone, DCM, THF, methylene chloride, methyl ethyl ketone, acetonitrile, DMSO, and/or polyethylene glycols in an amount between at least 20 to at most 95%; in which 100% (v/v/v) is the total amount of listed solvents in the mixture.

In some other embodiments the ternary mixture comprises DMSO in an amount between at least 5% to at most 80%, and two (traditional) solvents, preferably chosen from alcohol, acetone, DCM, THF, methylene chloride, methyl ethyl ketone, acetonitrile, DMSO, and/or polyethylene glycols, in an amount between at least 20 to at most 95%; in which 100% (v/v/v) is the total amount of listed solvents in the mixture; preferably 10% to 70% of DMSO, and 30% to 90 of two (traditional) solvents; more preferably 15% to 60% of DMSO, and 40% to 85 of two (traditional) solvents; for example 40% of acetic acid, 30% of alcohol and 30% of acetone; most preferably 20% to 50% of DMSO, and 50% to 80 of two (traditional) solvents; for example 40% of DMSO, 30% of ethanol and 30% of acetone; for example 50% of DMSO, 25% of methanol and 30% of DCM.

In some other particular embodiments the solvent is a quaternary solvent mixture, comprising at least one organic acid, preferably chosen from acetic acid and formic acid, and at least two other (traditional) solvent, preferably chosen from alcohol, acetone, DCM, THF, methylene chloride, methyl ethyl ketone, acetonitrile, DMSO, and/or polyethylene glycols. The quaternary mixture comprising at least 5%, preferably at least 10%, more preferably at least 15%, most preferably at least 20% (v/v) concentration of formic acid and/or acetic acid allows for a full dissolution of proteins (without precipitation); in particular wherein the protein is albumin (BSA, HAS) or gelatin.

In some other particular embodiments the solvent is a quaternary solvent mixture, comprising two organic acids, preferably chosen from acetic acid and/or formic acid, preferably are acetic acid and formic acid, and two other (traditional) solvents, preferably chosen from alcohol, acetone, DCM, THF, methylene chloride, methyl ethyl ketone, acetonitrile, DMSO, and/or polyethylene glycols.

In some other particular embodiments the solvent is a quaternary solvent mixture, comprising at least one organosulfur compound, preferably DMSO, and at least three other (traditional) solvents, preferably chosen from alcohol, acetone, DCM, THF, methylene chloride, methyl ethyl ketone, acetonitrile, DMSO, and/or polyethylene glycols. The quaternary mixture comprising at least 5%, preferably at least 10%, more preferably at least 15%, most preferably at least 20% (v/v) concentration of DMSO allows for a full dissolution of proteins (without precipitation); in particular wherein the protein is albumin (BSA, HAS) or gelatin.

In some particular preferred embodiments wherein the formulation is obtained via spray drying, the solvent comprises an organic acid, preferably chosen from acetic acid and formic acid.

In some particular preferred embodiments wherein the formulation is obtained via freeze drying, the solvent comprises an organosulfur compound, preferably DMSO.

In some other embodiments the formulation according to the present invention comprises a ratio of API to excipient between about at least 5% API and at most 95% excipient (w/w), to at least 95% API and at most 5% excipient (w/w), wherein 100% is defined as the total mass of the API and excipient. In some other embodiments the formulation according to the present invention comprises a ratio of API to excipient between about at least 10% API and at most 90% excipient (w/w), to at least 90% API and at most 10% excipient (w/w). In some other embodiments the formulation may comprise a ratio of API to excipient of about 50% API and about 50% excipient (w/w).

The inventors have found that these ratios (and the concentrations) offer an optimal balance between the excipient properties (e.g. enhanced solubility, dissolution rates and bioavailability) and the API dosage. Most importantly, these ratios were found to improve the solubility, permeability and/or dissolution (rate) of class II, class III and class IV APIs. Moreover, these concentrations of the provided (API and protein) materials offer an optimal balance between the aforementioned properties and production costs and timings of the formulation.

In some particular embodiments the formulation comprises a mass ratio (w/w) of API to excipient (w/w) between at least 5% API and at most 95% excipient, to at most 60% API and at least 40% excipient; wherein 100% is defined as the total mass of the API and excipient. In some particular embodiments the formulation comprises a mass ratio (w/w) of API to excipient (w/w) between at least 10% API and at most 90% excipient, to at most 60% API and at least 40% excipient. In some other particular embodiments the formulation comprises a mass ratio (w/w) of API to excipient (w/w) between at least 10% API and at most 90% excipient, to at most 60% API and at least 40% excipient. In some other particular embodiments the formulation comprises a mass ratio (w/w) of API to excipient (w/w) between at least 10% API and at most 90% excipient, to at most 40% API and at least 60% excipient In some other particular embodiments the formulation comprises a mass ratio (w/w) of API to excipient (w/w) between at least 5% API and at most 95% excipient, to at most 50% API and at least 50% excipient; wherein 100% is defined as the total mass of the API and excipient. In some particular embodiments the formulation comprises a mass ratio (w/w) of API to excipient (w/w) between at least 10% API and at most 90% excipient, to at most 50% API and at least 50% excipient. In some other particular embodiments the formulation comprises a mass ratio (w/w) of API to excipient (w/w) between at least 10% API and at most 90% excipient, to at most 50% API and at least 50% excipient. In some other particular embodiments the formulation comprises a mass ratio (w/w) of API to excipient (w/w) between at least 10% API and at most 90% excipient, to at most 40% API and at least 60% excipient.

In some other particular embodiments the formulation comprises a mass ratio (w/w) of API to excipient (w/w) between at least 10% API and at most 90% excipient, to at most 30% API and at least 70% excipient. In some other preferred embodiments the formulation comprises a ratio of API to excipient (w/w) between at least 10% API and at most 90% excipient, to at most 20% API and at least 80% excipient.

In some more particular embodiments the formulation may comprise a mass ratio (w/w) of API to excipient of about 50% API and about 50% excipient (w/w); wherein 100% is defined as the total mass of the API and excipient. In some other more particular embodiments the formulation may comprise a mass ratio (w/w) of API to excipient of about 40% API and about 60% excipient (w/w). In some other more particular embodiments the formulation may comprise a mass ratio (w/w) of API to excipient of about 30% API and about 70% excipient (w/w). In some more preferred embodiments the formulation may comprise a ratio of API to excipient of about 20% API and about 80% excipient (w/w). In some other more preferred embodiments the formulation may comprise a ratio of API to excipient of about 10% API and about 90% excipient (w/w). Higher amount of excipient can cause higher improvements for the solubility, dissolution rate, permeability and/or bioavailability; thus generally speaking a higher proportion (or weight ratio) of excipient relative to API may be preferred over a lower proportion. The inventors have found that the formulation according to the present invention allows for higher excipient to API ratios as compared to and achievable by employing aqueous based solvents. In a particular embodiment the formulations according to the present invention comprises 5% API, 10% API, 15% API, 20% API, 25% API, 30% API, 35% API, 40% API, 45% API or 50% API and 95% excipient, 90% excipient, 85% excipient, 80% excipient, 75% excipient, 70% excipient, 65% excipient, 60% excipient, 55% excipient or 50% excipient.

The inventors have found that such preferred ratios may result in an amorphous state of the formulation according to the present invention and thereby may exhibit improved solubility, dissolution rates and levels, achieving a supersaturation state and maintaining said state, and/or bioavailability when compared to formulations comprised of ratio different to the preferred ratios.

In some particular embodiments the formulation according to the present invention further comprises at least one hydrophilic carrier (HC).

In some embodiments the formulations according to the present invention comprises 5% HC, 10% HC, 15% HC, 20% HC, 25% HC, 30% HC, 35% HC, 40% HC, 45% HC or 50% HC (w %). In some embodiments the formulation comprises a ratio of excipient to API to HC is 80% to 10% to 10% (w/w/w); is 70% to 20% to 10%; is 60% to 30% to 10%; is 50% to 40% to 10%; is 40% to 30% to 10%; is 30% to 60% to 10%; is 20% to 70% to 10%; is 10% to 80% to 10%. In some embodiments the formulation comprises a ratio of excipient to API to HC is 70% to 10% to 20% (w/w/w); is 60% to 20% to 20%; is 50% to 30% to 20%; is 40% to 20% to 20%; is 30% to 50% to 20%; is 20% to 60% to 20%; is 10% to 70% to 20%. In some embodiments the formulation comprises a ratio of excipient to API to HC is 60% to 10% to 30%; is 50% to 20% to 30%; is 40% to 30% to 30%; is 30% to 40% to 30%; is 20% to 50% to 30%; is 10% to 60% to 30%.

In particular, the formulation as disclosed herein provides that said API is Flubendazole, Ibuprofen, Indomethacin, Naproxen, Phenytoin, Nifedipine, Vemurafenib, or Vera-pamil and wherein said protein based excipient obtained from a protein composition or a hydrolysate thereof which comprises BSA and/or gelatin. More in particular, the formulation as disclosed herein provides that said API is Flubendazole and wherein said protein based excipient obtained from a protein composition or a hydrolysate thereof which comprises BSA and/or gelatin.

In particular, the formulation as disclosed herein provides that said formulation is dosed in a solid-dosage form, preferably a tablet, lozenge, pill or capsule.

In some embodiments the formulation further comprises a solid-dosage form; preferably a solid-dosage form suitable for oral administration. In some preferred embodiments the formulation further comprises the form of a tablet, lozenge, pill or capsule. Advantageously the produced solid-dosage forms are suitable for unit-dose packaging, such as blisters packs; wherein each unit-dose is a formulation that contains a predetermined amount of API sufficient for one regular dose application or use.

The unit-doses are preferably produced, packaged and administered as (individual) solid dosage forms. Typically the unit-dose dimensions are adapted for oral administration (e.g. ease of swallowing as well as patient acceptance and compliance with treatment regimen). Exemplary dimension of tablets and capsules may range from $1 \times 1 \times 1$ mm$^3$ up to $20 \times 20 \times 20$ mm$^3$; for example $5 \times 5 \times 5$ mm$^3$; for example $10 \times 10 \times 10$ mm$^3$; for example $15 \times 15 \times 15$ mm$^3$. Typically the unit-dose shapes are adapted for oral administration, that is, tablets and capsules that have a larger cross sectional area (e.g., tablets that are rounder) would generally be more difficult to swallow than tablets or capsules of the same volume but with smaller cross sectional area. Advantageously, the shape has rounded corners to avoid hurting the user.

Having the API substantially amorphous in a solid dosage form may facilitate immediate supersaturation, and may further help maintain this degree of supersaturation. Consequently, having the formulation substantially amorphous in a solid dosage form may exhibit similar benefits. For oral administration a solid-dosage form is the preferred form applied by the industry and market. All steps for processing and producing a solid dosage form are also known in the art. The excipient and formulations as described by the present invention have shown compatibility with attaining and maintaining the structural and chemical properties expected of such a solid dosage form.

Having the API or the formulation substantially amorphous in a solid dosage form may facilitate beneficial interactions with traditional (polymer) excipients. For example, the presence of at least one excipient such as an interacting polymer may facilitate immediate supersaturation, and/or may further help maintain this degree of supersaturation. This process may be easily scalable and directly amenable for creating a commercial product. Traditional (polymer) excipients do not reach the amorphous state observed for the protein excipient as described by the present invention. However, by mixing a protein excipient and with a traditional (polymer) excipient the amorphous state of the formulation may be improved accordingly. In particular amounts of gelatin or (serum) albumin may increase the amorphous state of the formulation substantially (verified experimentally). In particular embodiments the formulation according to the present invention further comprises at least one stabilizer. Delivering a stabile solid dosage can often present a challenge when producing a solid dosage form. Stabilizers as used herein may include, but are not limited to, antioxidants, sequestrants, emulsifiers and surfactants, UV absorbers, quenchers, scavengers, and the like. The choice of stabilizer depends mainly on the properties of the API (e.g. sensitivities, activity) and processing of the formulation.

In particular embodiments of the formulation according to the present invention further comprise at least one additional excipient not described by the present invention. By combining different excipients an improved (synergistic) effect may be observed, which would further improve the solubility, dissolution rate and/or bioavailability exceeding that of the excipients when used separately. Commonly non-protein excipients are designer polymers excipients. The use of polymer excipients is known in the art and examples may include, but are not limited to, Polyvinyl pyrrolidone (PVP) Polyethylene oxide (PEO), Hydroxypropyl Cellulose (HPC), Hydroxypropylmethylcellulose Acetate Succinate (HPMCAS), Ethyl cellulose (EC), Cellulose acetate butyrate (CAB), Cellulose Acetate Phthalate (CAP), Polyvinyl alcohol (PVA), Poly(ethylene glycol) (PEG), Poly(vinyl acetate) (PVAc), Methacrylates, Polylactide (PLA), Polyglycolide (PGA), Copolymers of PLA/PGA, Polycaprolactone (PCL), Ethylene Vinyl Acetate (EVA), Polyrethanes (TPU), Polyethylene (PE), Soluplus®, and the like.

Having the API or the formulation substantially amorphous in a solid dosage form may facilitate beneficial interactions with traditional (polymer) excipients. For example, the presence of at least one excipient such as an interacting polymer may facilitate immediate supersaturation, and/or may further help maintain this degree of supersaturation. This process may be easily scalable and directly amenable for creating a commercial product. Traditional (polymer) excipients do not reach the amorphous state observed for the protein excipient as described by the present invention. However, by mixing a protein excipient and with a traditional (polymer) excipient the amorphous state of the formulation may be improved accordingly. In particular amounts of gelatin or (serum) albumin may increase the amorphous state of the formulation substantially (verified experimentally in the examples).

In some particular embodiments the formulation according to the present invention further comprises at least one taste masking ingredient. Delivering effective protection from bitter tastes or unpleasant odors can often present a challenge when formulating a formulation. The formulation as described herein may ensure effective taste masking without compromising on the release times of the API once administered (orally). Typical taste masking ingredients may include, but are not limited to, Aspartame, Acesulfame potassium, Sucralose, Citric acid, Zinc sulfate, Cyclodextrin (e.g. Beta, Gamma, Hydroxyl Propyl, etc.), flavor additives (e.g. lemon, mint, etc.), and the like.

In some particular embodiments the formulation according to the present invention further comprises at least one coating layer. Delivering effective protection for outside influences may be an important requirement for a formulation. Several coating layers may further improve the chemical properties of the formulation; for instance by offering a catalytic effect to the solubility; or further prevent the formulation from dissolving prior to reaching its desired target, for example by protecting an intestinal formulation against stomach fluids. Additionally, some coating layers may also serve as a moisture protective ingredient. When exposed to moisture, a solid dosage form (e.g. tablets) can swell and may crack. A moisture protective may counteract excessive moisture intake and thus prevent cracking of the solid dosage form. The use of a coating layer is known in the art and examples may include, but are not limited to, Methacrylate formulations, Hydroxypropyl methylcellulose formulations (HPMC), Polyvinyl alcohol formulations (PVA), Kollicoat® and the like.

In some particular embodiments the formulation according to the present invention further comprises at least one surfactant. A surfactant can be used to reduce the surface tension of a liquid in which the formulation is dissolved The surfactants as used herein may include, but are not limited to, pH modifiers, fillers, complexing agents, solubilizers, pigments, lubricants, glidants, flavor agents, plasticizers, taste masking agents, release-modifying polymers, and the like.

In particular, the formulation as disclosed herein provides that said formulation is characterized by having a particle size between 1 μm and 1 mm; preferably between 5 μm and 50 μm; most preferably between 10 μm and 20 μm, for example 15 μm.

As used herein the term "particle size" refers to the size of the individual particles comprised in a powder. Said particles have a diameter ranging between a nanometer and several millimeters. For the present invention the particle size is preferably in the order of micrometers. Related is the 'particle-size distribution' (PSD) of a powder or particles dispersed in fluid; which comprises a list of values or a mathematical function that defines the relative amount, typically by mass, of particles present according to size.

The PSD may affect the reactivity of solids participating in chemical reactions, and needs to be tightly controlled in pharmaceutical products.

For fast release, generally the smaller the particle size the faster the API enters a solution. However, for API exhibiting a low solubility and/or bioavailability the faster they enter a solution, the higher the local temporary concentration, and the bigger the pressure to precipitate out into crystals. Thus the inventors have found that for certain API it is instead better to have a larger particle size up to a millimeter. Certain processing techniques, such as the drying methods, allow the particle size to be steered through the process parameters. The benefit of a custom particle size is that this way also the flowing properties of the formulation can be manipulated, for instance through the inclusion of additives.

In some particular embodiments the protein based excipient according to the present invention is characterized by having a particle size of at least 0.1 μm to at most 1.0 mm; or at least 1 μm to at most 50 μm; or at least 5 μm to at most 40 μm, for example 20 μm or 30 μm. In a particular embodiment the protein based excipient according to the present invention is characterized by having a particle size of at least 5 μm to at most 25 μm; more preferably at least 7 μm to at most 15 μm; most preferably about 10 μm.

In general a lower particle size can be associated with an improved dissolution level and rate, which may further improve achieving a state of supersaturation and help maintaining said supersaturation state. Obviously, any processing steps which seek to decrease the particle size, e.g. by altering the solvent, the drying method, or mixing method, may also further contribute to the benefits disclosed by the present invention. However, additional post-processing steps which may physically stress to the native protein, resulting in a loss of the quaternary, tertiary and/or secondary structure which is present in their native state or a loss of the protein's biological activity, will generally be detrimental for the purposes of the present inventions. Examples may include, further cutting, milling, slicing, pressing, grinding, and the like.

In a particular embodiment the BSA based excipient is characterized by having a particle size of at least 0.1 μm to at most 1.0 mm; or at least 1 µm to at most 50 µm; or at least 5 µm to at most 40 µm; preferably about 10 µm.

In a particular embodiment the gelatin based excipient is characterized by having a particle size of at least 0.1 µm to at most 1.0 mm; or at least 1 µm to at most 50 µm; or at least 5 µm to at most 40 µm; preferably about 15 µm.

The disclosed particle size can be steered to control the processing scale of the formulation in powder form. By obtaining a sufficiently low particle size which is substantially amorphous higher total solid contents can be more easily processed in comparison with traditional (polymer) excipients. In particular an increment of 25% in extra cost efficiency and time reduction may be achieved.

According to a further aspect, the present invention relates to the use of a protein composition or a hydrolysate thereof comprising proteins—as per monomer—of at least 10 amino acids in length as a protein based excipient. Advantageously, proteins—as per monomer—are at least 20 amino acids in length; more preferably at least 50 amino acids in length; most preferably at least 100 amino acids in length, for example at least 250 amino acids or at least 500 amino acids in length.

In some embodiments, the formulation is provided in a solid-dosage form, preferably in a form adapted for oral administration such as tablet, lozenge, pill or capsule, or as components for reconstituting an injectable. Advantageously, the solid-dosage form is a unit-dose that contains a predetermined amount of API sufficient for one regular application or use of said API, and wherein the unit-dose is suitable for unit-dose packaging, such as blisters packs.

According to a further aspect, the present invention relates to a method for producing a pharmaceutical formulation comprising
  a protein based excipient obtained from a protein composition or a hydrolysate thereof which comprises proteins—as per monomer—of at least 10 amino acids in length; and
  an active pharmaceutical ingredient (API);
characterized therein that said protein based excipient and said API are both substantially amorphous;
said method comprising at least the steps of:
  (a) dissolving said API using a solvent to obtain a solution; and
  (b) drying the solution of step (a) to obtain a powder that is substantially amorphous.

Preferably, the drying serves to form a solid dispersion comprising a protein based excipient as excipient and an API. Advantageously, the proteins—as per monomer—are at least 20 amino acids in length; more preferably at least 50 amino acids in length; most preferably at least 100 amino acids in length, for example at least 250 amino acids or at least 500 amino acids in length, In a particular embodiment of the present invention, said protein composition or hydrolysate thereof is chosen from soy protein, pea protein, blood proteins, Immunoglobulins, milk proteins, gelatine, keratin, corn, wheat, hemp, rye, oats, peanut, barley, casein, albumin, whey protein (lactalbumin), Hydrolysed Whey Protein Isolate (HWPI), hydrolyzed collagen, plasma proteins, serum albumin, bovine serum albumin (BSA), human serum albumin (HSA), egg albumin, fish albumin, elastin, collagen, recombinant or artificial proteins, recombinant versions of natural or artificial binding scaffolds, and/or a combination thereof; preferably HSA, BSA, gelatine and/or a combination thereof.

In some particular embodiments the solvent used to dissolve the protein composition or hydrolysate thereof, and/or the API is an organic acid; preferably the solvent is formic acid or acetic acid. The organic acid solvents are particularly well suitable for preparation of a (protein and API) solution for spray drying.

In another particular embodiment the solvent is an organosulfur compound, preferably dimethyl sulfoxide (DMSO). The organosulfur solvents are particularly well suitable for preparation of a (protein and API) solution for freeze drying.

In some embodiments the solvent used to dissolve the protein composition or hydrolysate thereof, and/or the API is a mixture comprising at least 2.5% of an organic acid to at most 100% of an organic acid (v/v), preferably chosen from acetic acid or formic acid; preferably 5% to 99% organic acid, preferably 10% to 90% organic acid, preferably 15% to 90% organic acid; preferably 20% to 90% organic acid; preferably 10% to 80% organic acid; preferably 15% to 80% organic acid; preferably 20% to 80% organic acid; preferably 10% to 70% organic acid; preferably 15% to 70% organic acid; preferably 20% to 70% organic acid; more preferably 30% to 70% organic acid; more preferably 30% to 60% organic acid; more preferably 40% to 70% organic acid; more preferably 40% to 60% organic acid; most preferably 45% to 55% organic acid.

In some embodiments the solvent used to dissolve the protein composition or hydrolysate thereof, and/or the API is a mixture comprising at least one organic acid, preferably chosen from acetic acid and/or formic acid, in an amount between at least 5% to at most 80% and another solvent, preferably chosen from an alcohol or acetone, in an amount of at least 20% to at most 95%, in which 100% (v/v) is the total amount of solvents in the mixture; preferably 10% to 80% organic acid and 20% to 90% of another solvent; preferably 15% to 80% organic acid and 20% to 85% of another solvent; more preferably 20% to 80% organic acid and 20% to 80% of another solvent; more preferably 20% to 70% organic acid and 30% to 80% of another solvent; more preferably 30% to 70% organic acid and 30% to 70% of another solvent; more preferably 30% to 60% organic acid and 40% to 70% of another solvent; more preferably 40% to 70% organic acid and 30% to 60% of another solvent; most preferably 40% to 60% organic acid and 40% to 60% of another solvent; most preferably 45% to 60% organic acid and 40% to 55% of another solvent; most preferably 45% to 55% organic acid and 45% to 55% of another solvent.

In some particular embodiments the solvent used to dissolve the protein composition or hydrolysate thereof, and/or the API is a binary solvent mixture, comprising one organic acid, preferably chosen from acetic acid or formic acid, and another solvent, preferably chosen from alcohol or acetone. In some preferred embodiments the binary mixture comprises an organic acid, preferably chosen from formic acid or acetic acid, in an amount between at least 5% to at most 80% and another solvent, preferably chosen from an alcohol or acetone, in an amount of at least 20% to at most 95%, in which 100% (v/v) is the total amount of solvents in the mixture; preferably 10% to 80% organic acid and 20% to 90% of another solvent; preferably 15% to 80% organic acid and 20% to 85% of another solvent; more preferably 20% to 80% organic acid and 20% to 80% of another solvent; more preferably 20% to 70% organic acid and 30% to 80% of another solvent; more preferably 30% to 70% organic acid and 30% to 70% of another solvent; more preferably 30% to 60% organic acid and 40% to 70% of another solvent; more preferably 40% to 70% organic acid and 30% to 60% of another solvent; most preferably 40% to 60% organic acid and 40% to 60% of another solvent; most preferably 45% to 60% organic acid and 40% to 55% of another solvent; most preferably 45% to 55% organic acid and 45% to 55% of another solvent.

In some particular embodiments the solvent used to dissolve the protein composition or hydrolysate thereof, and/or the API is a ternary solvent mixture, comprising one organic acid, preferably chosen from acetic acid or formic acid, and two other solvents, preferably chosen from alcohol or acetone; for example acetic acid and alcohol and a third non-listed solvent. Alternatively, the ternary solvent mixture comprises two organic acids, preferably chosen from acetic acid and/or formic acid (for example acetic acid and formic acid) and one other solvent, preferably chosen from alcohol or acetone.

In some preferred embodiments the ternary solvent mixture comprises one organic acid, preferably chosen from acetic acid or formic acid, in an amount between at least 5% to at most 80%, and two other solvents, preferably chosen from alcohol or acetone, in a combined amount between at least 20% to at most 95%; in which 100% (v/v/v) is the total amount of solvents in the mixture; preferably 10% to 80% of one organic acid and 20% to 90% of two other solvents; preferably 15% to 80% one organic acid and 20% to 85% of two other solvents; more preferably 20% to 80% one organic acid and 20% to 80% of two other solvents; more preferably 20% to 70% one organic acid and 30% to 80% of two other solvents; more preferably 30% to 70% one organic acid and 30% to 70% of two other solvents; more preferably 30% to 60% one organic acid and 40% to 70% of two other solvents; more preferably 40% to 70% one organic acid and 30% to 60% of two other solvents; most preferably 40% to 60% one organic acid and 40% to 60% of two other solvents; most preferably 45% to 60% one organic acid and 40% to 55% of two other solvents; most preferably 45% to 55% one organic acid and 45% to 55% of two other solvents. For example, a ternary mixture that contains 20% of formic acid, 40% of alcohol and 40% of acetone; for example, a ternary mixture that contains 40% of acetic acid, 40% of alcohol and 20% of acetone; for example, a ternary mixture that contains 50% of formic acid, 25% of alcohol and 25% of acetone.

In some other preferred embodiments the ternary solvent mixture comprises two organic acids, preferably chosen from acetic acid or formic acid, more preferably acetic acid and formic acid, in a combined amount between at least 5% to at most 80%, and one other solvents, preferably chosen from alcohol or acetone, in an amount between at least 20% to at most 95%; in which 100% (v/v/v) is the total amount of solvents in the mixture; preferably 10% to 80% of two organic acids and 20% to 90% of one other solvent; preferably 15% to 80% two organic acids and 20% to 85% of one other solvent; more preferably 20% to 80% two organic acids and 20% to 80% of one other solvent; more preferably 20% to 70% two organic acids and 30% to 80% of one other solvent; more preferably 30% to 70% two organic acids and 30% to 70% of one other solvent; more preferably 30% to 60% two organic acids and 40% to 70% of one other solvent; more preferably 40% to 70% two organic acids and 30% to 60% of one other solvent; most preferably 40% to 60% two organic acids and 40% to 60% of one other solvent; most preferably 45% to 60% two organic acids and 40% to 55% of one other solvent; most preferably 45% to 55% two organic acids and 45% to 55% of one other solvent. For example, a ternary mixture that contains 20% of formic acid, 20% of acetic acid and 60% of alcohol; for example, a ternary mixture that contains 25% of formic acid, 25% of acetic acid and 50% of acetone; for example, a ternary mixture that contains 20% of formic acid, 50% of acetic acid and 30% of acetone.

In some particular embodiments the solvent used to dissolve the protein composition or hydrolysate thereof, and/or the API is a quaternary solvent mixture, comprising at least one organic acid, preferably chosen from acetic acid and/or formic acid, and at least other solvent, preferably chosen from alcohol and/or acetone; in a way that the quaternary solvent mixture comprises a total of four solvents.

In some more particular embodiments the solvent used to dissolve the protein composition or hydrolysate thereof, and/or the API is a quaternary solvent mixture, comprising two organic acids, preferably chosen from acetic acid and/or formic acid, and two other solvents, preferably chosen from alcohol and/or acetone.

In some preferred embodiments the quaternary solvent mixture comprises one organic acid, preferably chosen from acetic acid or formic acid, in an amount between at least 5% to at most 80%, and three other solvents, preferably chosen from alcohol and/or acetone, in a combined amount between at least 20% to at most 95%; in which 100% (v/v/v) is the total amount of solvents in the mixture; preferably 10% to 80% of one organic acid and 20% to 90% of two other solvents; preferably 15% to 80% one organic acid and 20% to 85% of three other solvents; more preferably 20% to 80% one organic acid and 20% to 80% of three other solvents; more preferably 20% to 70% one organic acid and 30% to 80% of three other solvents; more preferably 30% to 70% one organic acid and 30% to 70% of three other solvents; more preferably 30% to 60% one organic acid and 40% to 70% of three other solvents; more preferably 40% to 70% one organic acid and 30% to 60% of three other solvents; most preferably 40% to 60% one organic acid and 40% to 60% of three other solvents; most preferably 45% to 60% one organic acid and 40% to 55% of three other solvents; most preferably 45% to 55% one organic acid and 45% to 55% of three other solvents. For example, a quaternary mixture that contains 20% of formic acid, 30% of alcohol, 30% of acetone and 20% of acetonitrile; for example 30% of acetic acid, 40% of acetone and 30% of alcohol of which 15% is ethanol and 15% is methanol.

In some preferred embodiments the quaternary solvent mixture comprises two organic acids, preferably chosen from acetic acid and/or formic acid, more preferably acetic acid and formic acid, in a combined amount between at least 5% to at most 80%, and two other solvents, preferably chosen from alcohol and/or acetone, in a combined amount between at least 20% to at most 95%; in which 100% (v/v/v) is the total amount of solvents in the mixture; preferably 10% to 80% of two organic acids and 20% to 90% of two other solvents; preferably 15% to 80% two organic acids and 20% to 85% of two other solvents; more preferably 20% to 80% two organic acids and 20% to 80% of two other solvents; more preferably 20% to 70% two organic acids and 30% to 80% of two other solvents; more preferably 30% to 70% two organic acids and 30% to 70% of two other solvents; more preferably 30% to 60% two organic acids and 40% to 70% of two other solvents; more preferably 40% to 70% two organic acids and 30% to 60% of two other solvents; most preferably 40% to 60% two organic acids and 40% to 60% of two other solvents; most preferably 45% to 60% two organic acids and 40% to 55% of two other solvents; most preferably 45% to 55% two organic acids and 45% to 55% of two other solvents. For example, a quaternary mixture that contains 20% of formic acid, 20% of acetic acid, 30% of acetone and 30% of alcohol; for example 30% of formic acid, 30% of acetic acid, and 40% of alcohol of which 15% is ethanol and 15% is methanol.

Essentially any acid suitable for dissolving a protein composition or hydrolysate thereof without too adversely affecting the protein structure (i.e. denaturizing, aggregation, disintegrating, burning, etc.) may be suitable for the purposes of the present invention. However, the inventors have found that formic acid, trifluoroacetic acid, and acetic acid exhibit very desirable properties for the purposes of the present invention. Said acids dissolve the proteins to a desirable protein solution without substantially denaturing said proteins (i.e. retaining their biological activity), thereby providing a protein solution which can be dried to obtain the protein based excipient as described by the present invention. In particular formic acid and acetic acid were found to exhibit very desirable properties for dissolving albumin (e.g. HSA, BSA) and gelatin.

Similar considerations were made for dissolving the API; that is, essentially any acid suitable for dissolving API without too adversely affecting the API chemical structure or biological activity may be suitable for the purposes of the present invention. In particular formic acid and acetic acid were found to exhibit desirable properties for dissolving Flubendazole, Carbamazepine, Griseofulvin, Phenytoin, Nifedipine, Verapamil, Azithromycin, Nitrofurantoin, lopanoic acid, Itraconazole, Ibuprofen, Indomethacin, Glibenclamide, Bicalutamide, Ezetimibe, Aceclofenac, Ketoconazole, Oxfendazole, Ritonavir, Saquinavir, Fenofibrate, Cinnarizin, Darunavir, Diazepam, Bifonazole, Testosterone undecanoate, or Naproxen; more in particular for dissolving Flubendazole, Ibuprofen, Indomethacin, Ritonavir, Naproxen, Phenytoin, Nifedipine, Vemurafenib, Griseofulvin, Itraconazole, or Verapamil.

The term "drying" refers to any method or technique which promotes a mass transfer of a liquid medium, such as water or another solvent, through evaporation. Specifically for the purposes of the present invention, drying involves any method which transforms the liquid state of a solution (e.g. protein solution, API solution, protein-API solution) into a solid, preferably powdered state (e.g. dried protein excipient, dried API, dried formulation). Care may be necessary for the drying method not to inflict any undesired damage to the excipient or the API, which may be caused by physical conditions such as excessive heat. Preferably the drying method is chosen from spray drying, freeze drying, vacuum drying, flash drying, paddle drying, air drying, condensation drying, and the like.

Essentially any drying method suitable for drying a protein solution, or an API solution or a protein-API solution without too adversely affecting the chemical structure of the solution(s) may be suitable for the purposes of the present invention. However, the inventors have found that spray drying displays very desirable properties for the purposes of the present invention. The inventors have also found that freeze drying displays desirable properties for the purposes of the present invention.

Spray drying dries said protein solution without substantially denaturing the dissolved proteins (i.e. retain their biological activity), thereby obtaining a dried protein based excipient as described by the present invention. Spray drying is a versatile drying method that can be easily adapted to different feedstock (e.g. proteins, API) and product specifications (e.g. particle size). Additionally, spray drying has a (very) high drying speed and allows for a high level of control over bulk density and residual solvent levels. More importantly, it allows for easy and reliable quality control, which is of great importance for industries like pharmaceuticals. In particular spray drying was found to display very desirable properties for drying albumin (e.g. HSA, BSA) and gelatin.

Similarly, freeze drying also dries said protein solution without substantially denaturing the dissolved proteins and/or API. Additionally, freeze drying also allows for comparably less harsh and continuous processing conditions. In particular freeze drying was found to display very desirable properties for drying albumin (e.g. HSA, BSA) and gelatin.

Spray drying also dries said API solution without too adversely affecting the chemical structure and biological activity of the API, thereby obtaining a dried API which is substantially amorphous as described by the present invention. In particular spray drying was found to display very desirable properties for drying a solution comprising Flubendazole, Carbamazepine, Griseofulvin, Phenytoin, Nifedipine, Verapamil, Azithromycin, Nitrofurantoin, lopanoic acid, Itraconazole, Ibuprofen, Indomethacin, Glibenclamide, Bicalutamide, Ezetimibe, Aceclofenac, Ketoconazole, Oxfendazole, Ritonavir, Saquinavir, Fenofibrate, Cinnarizin, Darunavir, Diazepam, Bifonazole, Testosterone undecanoate, or Naproxen; more in particular for drying a solution comprising Flubendazole, Ibuprofen, Indomethacin, Ritonavir, Naproxen, Phenytoin, Nifedipine, Vemurafenib, Griseofulvin, Itraconazole, or Verapamil.

Similarly, freeze drying also dries said API solution without (too) adversely affecting the chemical structure and biological activity of the API, thereby obtaining a dried API which is substantially amorphous as described by the present invention. In particular freeze drying was found to display very desirable properties for drying a solution comprising Flubendazole, Carbamazepine, Griseofulvin, Phenytoin, Nifedipine, Verapamil, Azithromycin, Nitrofurantoin, lopanoic acid, Itraconazole, Ibuprofen, Indomethacin, Glibenclamide, Bicalutamide, Ezetimibe, Aceclofenac, Ketoconazole, Oxfendazole, Ritonavir, Saquinavir, Fenofibrate, Cinnarizin, Darunavir, Diazepam, Bifonazole, Testosterone undecanoate, or Naproxen; more in particular for drying a solution comprising Flubendazole, Ibuprofen, Indomethacin, Ritonavir, Naproxen, Phenytoin, Nifedipine, Vemurafenib, Griseofulvin, Itraconazole, or Verapamil.

The term "spray drying" as used herein refers to a preferred method of drying for the present invention, wherein a dry powder is produced from a liquid solution (or suspension or slurry) with a hot gas. The standard laboratory setup for a person skilled in the art to practice spray drying typically comprises (1) a solution or suspension to be dried, (2) gas used for drying, (3) spray nozzles, for spraying said solution or suspension; (4) a drying chamber, (5) a cyclone chamber (6) connector parts between drying chamber and cyclone, and (7) a collecting vessel. Other components or parts not detailed may also be further comprised depending on production parameters (i.e. the solution or gas types, spray nozzles types, production scale and times, etc.). Examples of alternative components include different spray nozzles, e.g., single-fluid high pressure swirl nozzles, ultrasonic nozzles; or other components such as rotary disks, atomizer wheels. In general the spray drying set-up is commonly known in the art and may comprise various models and techniques recognized by those skilled in the art.

In some embodiments the spray drying is performed at a temperature of at least 60° C. to at most 240° C.; or at least 110° C. to at most 160° C.; preferably at least 130° C. to at most 150° C. In a most preferred embodiment the spray drying is performed at a temperature of about 140° C. The inventors have found that a temperature of 140° C. provides an optimal temperature for effectively spray drying the protein solution without causing undesired chemical or structural changes to the excipient.

The term "freeze drying" as used herein refers to a preferred method of drying for the present invention, wherein a dry powder is produced from a liquid solution (or suspension or slurry) by freezing the solution and then reducing the surrounding pressure to allow the frozen solvent in the material to sublimate directly from the solid phase to the gas phase. Freeze drying is sometimes also referred to as "lyophilisation", "lyophilization", or "cryodesiccation". Typically freeze drying is a four step process that involves: (1) pretreatment, (2) freezing, (3) primary drying (with sublimation) and (4) secondary drying (with adsorption). The standard laboratory setup for a person skilled in the art to practice freeze drying typically comprises (1) a solution or suspension to be dried, and (2) freeze drying equipment (e.g. manifold freeze-dryer, the rotary freeze-dryer and/or the tray style freeze-dryer). Other components or parts not detailed may also be further comprised depending on production parameters (i.e. the solution types, storage equipment and containers, production scale and times, etc.). In general the freeze drying set-up is commonly known in the art and may comprise various models and techniques.

In some embodiments the freeze drying is performed at a temperature of at least −110° C. to at most −50° C.; preferably at least −110° C. to at most −60° C.; preferably at least −110° C. to at most −70° C.; preferably at least −110° C. to at most −75°; preferably at least −110° C. to at most −80° C.; more preferably at least −100° C. to at most −60° C.; more preferably at least −100° C. to at most −70° C.; more preferably at least −100° C. to at most −75° C.; more preferably at least −100° C. to at most −80° C.; most preferably at least −90° C. to at most −60° C.; most preferably at least −90° C. to at most −70° C.; most preferably at least −90° C. to at most −75° C.; most preferably at least −90° C. to at most −80° C. In a most preferred embodiment the spray drying is performed at a temperature of about −85° C.; for example −83° C.; for example −87° C.; for example −85° C. The inventors have found that the listed preferred values for temperatures allow for effectively freeze drying the protein solution without causing undesired chemical or structural changes to the excipient. In some embodiments the freeze drying is performed at a pressure of at least 0.001 mbar to at most 0.030 mbar; preferably at least at least 0.002 mbar to at most 0.020 mbar; preferably at least 0.004 mbar to at most 0.015 mbar; most preferably at least 0.005 mbar to at most 0.010 mbar. In a most preferred embodiment the spray drying is performed at a pressure of about 0.008 mbar; for example 0.009 mbar; for example 0.007 mbar; for example 0.008 mbar. The inventors have found that the listed preferred pressure values allow for effectively freeze drying the protein solution without causing undesired chemical or structural changes to the excipient.

Additionally, prior to freeze drying the solution is frozen and stored for at least 12 hours; preferably at least 24 hours; more preferably at least 36 hours; most preferably at least 48 hours; at a temperature of at least −40 to at most −10° C.; preferably at least −35 to at most −15° C.; more preferably at least −30 to at most −20° C.; most about −25° C.; for example −23° C.; for example −27° C.; for example −25° C. The storage step allows for maximizing surface areas of the solutions.

In some preferred embodiments the protein based excipient is characterized in that the excipient is obtained through dissolving or solubilizing a protein composition or a hydrolysate thereof in an organic solvent to obtain a protein solution and spray drying said protein solution to obtain the protein based excipient. In some other preferred embodiments the protein based excipient is characterized in that the excipient is obtained through dissolving or solubilizing a protein composition or a hydrolysate thereof in formic acid to obtain a protein solution and spray drying said protein solution to obtain the protein based excipient. In some other preferred embodiments the protein based excipient is characterized in that the excipient is obtained through dissolving or solubilizing a protein composition or a hydrolysate thereof in acetic acid to obtain a protein solution and spray drying said protein solution to obtain the protein based excipient.

In some other preferred embodiments the protein based excipient is characterized in that the excipient is obtained through dissolving or solubilizing a protein composition or a hydrolysate thereof in DMSO to obtain a protein solution and freeze drying said protein solution to obtain the protein based excipient.

Commonly it is assumed that dissolving a protein in an organic acid at pH<1 followed by drying would affect its tertiary and secondary structure, hence producing powders composed of denatured protein. The inventors have surprisingly observed that proteins retain their structure and biological functionality after the process; in particular gelatin and (serum) albumin. Since their biological activity (i.e. the interaction with foreign molecules, such as the API, or the ability to form a three-dimensional meshwork), relies on the fully folded structure of the protein molecule, it was observed that the excipients obtained from a protein dried from a solution with an organic acid and/or DMSO remained unaffected for at least several hours. These findings using gel permeation analysis are demonstrated in the examples section.

By drying the amorphous state of the protein composition dissolved in an organic acid is retained, thereby forming a powder that is substantially amorphous and substantially not denatured; in particular completely amorphous and not denatured. The resulting powder retains many properties which are preferred for use as an excipient; in particular a protein based excipient. The same effects are observed for a powder obtained from a singular protein source protein (e.g. BSA or gelatin), but also for a protein composition comprising multiple sources of proteins (e.g. BSA and gelatin).

In some particular embodiments the process for making the formulation according to the present invention further comprises a stabilizing process for producing a solid dosage form, such as a tablet, pill, lozenge or capsule, advantageously with the dimensional parameters suitable for oral administration. A stabilizing step includes moulding, compression, and the like.

In some particular embodiments wherein the formulation is spray dried, the spray drying process produces a powder that can formed into a solid dosage form; preferably the spray drying process is followed by a solid dosage forming process, such as compression or molding.

In some particular wherein the formulation is freeze dried, the freeze drying process produces a powder that can formed into a solid dosage form. Alternatively, the freeze drying process dries the feedstock directly into a solid dosage form, such as pills or tablets. In a preferred embodiment the DMSO dissolved formulation comprising the protein based excipient and API (as an amorphous solid dispersion) is freeze dried directly into a solid dosage form; for example freeze dried directly into blisters to produce a tablet or pill. In some particular embodiments the method of step (a)

further comprises the steps of: dissolving said API in combination with at least one hydrophilic carrier (HC) using a solvent to obtain a solution.

In some embodiments the hydrophilic carrier is selected from the following list of polymer excipients known in the art, but are not limited to, Polyvinyl pyrrolidone (PVP) Polyethylene oxide (PEO), Hydroxypropyl Cellulose (HPC), Hydroxypropylmethylcellulose Acetate Succinate (HPMCAS), Ethyl cellulose (EC), Cellulose acetate butyrate (CAB), Cellulose Acetate Phthalate (CAP), Polyvinyl alcohol (PVA), Poly(ethylene glycol) (PEG), Poly(vinyl acetate) (PVAc), Methacrylates, Polylactide (PLA), Polyglycolide (PGA), Copolymers of PLA/PGA, Polycaprolactone (PCL), Ethylene Vinyl Acetate (EVA), Polyrethanes (TPU), Polyethylene (PE), Soluplus®, and the like.

In particular, the method as disclosed herein provides that the protein based excipient is prepared through the steps of:

(i) dissolving an protein composition or hydrolysate thereof using a solvent to obtain a solution; and (ii) drying the solution of step (i) to obtain said protein based excipient.

In particular, the method as disclosed herein provides that the solutions of steps (a) and (i) are dissolved using a common or different solvent.

In particular, the method as disclosed herein provides that the API and protein based excipient are either:

dissolved and dried together in the same solvent, thereby forming said pharmaceutical formulation;

dissolved separately in the same or a different solvent and subsequently dried together, thereby forming said pharmaceutical formulation;

dissolved in the same or a different solvent and dried separately and subsequently mixed, thereby forming said pharmaceutical formulation.

In particular, the method as disclosed herein provides that the solvent is an organic acid; preferably formic acid, trifluoroacetic acid, or acetic acid.

In particular, the method as disclosed herein provides that the solvent is an organosulfur compound; preferably DMSO.

In particular embodiments the method according to the present invention is characterized in that the protein based excipient is obtained through dissolving or solubilizing a protein composition or a hydrolysate thereof in a solvent to obtain a protein solution and drying said protein solution to obtain a protein based excipient, and further characterized in that the amorphous API is obtained through dissolving or solubilizing a API in a solvent, similar or different from the solvent used for the protein solution, to obtain an API solution and drying said API solution to obtain an API which is substantially amorphous, and further combining said dried excipient and said dried API to obtain a formulation which is substantially amorphous according to an embodiment of the invention.

Alternatively, in some other embodiments the method according to the present invention is characterized in that the formulation is obtained through dissolving or solubilizing a protein composition or a hydrolysate thereof in a solvent to obtain a protein solution, dissolving or solubilizing an API in a common or different solvent and subsequently mixing the protein solution with the API and drying said mixture to obtain a formulation which is substantially amorphous according to an embodiment of the invention.

Alternatively, in some other embodiments the method according to the present invention is characterized in that the formulation is obtained through dissolving or solubilizing a protein composition or a hydrolysate thereof together with an API in a common solvent and drying said protein-API solution to obtain a formulation which is substantially amorphous according to an embodiment of the invention.

Alternatively, in some other embodiments the method according to the present invention is characterized in that the formulation is obtained through dissolving or solubilizing an API in a solvent and drying said API solution to obtain an API which is substantially amorphous, and further combining said dried API with a provided protein based excipient which is preferably substantially not denaturized to obtain a formulation which is substantially amorphous according to an embodiment of the invention. Additionally, the dissolving or solubilizing of said API is further improved by an addition of a hydrophilic carrier to the solution.

In some particular embodiments the formulation further comprises a co-solubilizer. Certain APIs may prove difficult to dissolve in an acid or a protein solution. A co-solubilizer may be used to facilitate this. In particular, said co-solubilizer is chosen form a cyclodextrin, sorbitan monostearate, a polyoxyethylene-polyoxypropylene block copolymer, polyoxyethyleneglyceroltriricinoleate 35, dimethylformamide, and the like.

The solubility and dissolution rate of the API used in the formulation according to the present invention directly affects the bioavailability of the API. Therefore, it is very important to increase the solubility and the dissolution rate of the API, especially for APIs exhibiting a low solubility and/or bioavailability. Achieving a state of supersaturation, and subsequently maintaining said supersaturation state for as long as possible, results in even more favorable results of the API. Additionally, an improvement in bioavailability and supersaturation increases the in-take speed of the API; which results in a lowered total weight/volume (dosage) required of the API in a formulation.

Alternatively, the excipient according to the present invention as described herein may be combined with at least one designer polymer excipient to obtain a formulation which potentially even surpasses the solubility and/or bioavailability enhancing properties of both excipient types separately. It also further facilitate achieving a state of supersaturation, and subsequently further helps maintaining said supersaturation state for as long as possible. Thus the formulation may form a solid dispersion.

The present invention encompasses several embodiments on obtaining the formulation, and those skilled in the art may appreciate further variations in the formulation and on the preparation method, obtaining similar effects as described herein. Exemplary variations for developing the formulation may include:

(i) adding additional components to the formulation, such as at least one additional (non-protein based) excipient, stabilizer, taste masking ingredient, coating layer, moisture protective ingredient, surfactant, etc.;

(ii) controlling the rate and degree of supersaturation of the formulation by optimizing said protein based excipient's properties; e.g. selecting different proteins, different protein sources, different protein compositions, etc.;

(iii) implementing selective adjustments to the protein excipient for steering the pharmacokinetic properties of the formulation, for example to control the absorption (i.e. control the rate and concentration of API entering the blood circulation), the liberation (i.e. control the moment and location of API release from the formulation), the distribution (i.e. promote or prevent the dispersion of the API throughout the fluids and tissues of the body), the metabolization (i.e. protect or promote the digestion of the API the fluids and tissues of the body) and the excretion (i.e. safely remove unabsorbed API from the body for some cases where API may irreversibly accumulate in body tissue);

(iv) adjusting the formulation properties and processing cost, time and/or scale by optimizing the processing method, such as altering solvents, solution and drying methods, etc.

According to a further aspect, the present invention relates to a formulation as disclosed herein for use as a medicament. In particular, said formulation is used for the treatment of problems with the gastrointestinal tract (digestive system), problems with the cardiovascular system, problems with the central nervous system, problems with the musculo-skeletal system, problems with the respiratory system, problems with the endocrine system, problems with the reproductive system, problems with the urinary system, problems with the immune system, problems with obstetrics and problems with gynecology (contraception), and/or for problems with the eye, ear, nose, oropharynx or skin. The formulation as described by the present invention may be a product for treating infections and infestations (antibiotic, antifungal, antiparasitic), pain and consciousness (analgesic drugs), allergic disorders, nutritional disorders, and/or neoplastic disorders.

The formulation as described by the present invention may be a product for diagnostic use.

EXAMPLES

Example 1: Determining Preferred Protein Sources

Various proteins from all domains of nature (e.g. animal, vegetable and microbial origin) are amenable for dissolution in an organic acid followed by (spray or freeze) drying and re-dissolution in a liquid system.

In the following experiment 5% solutions of various proteins were dissolved in formic acid and solvent-casted into protein films. The proteins were selected from gelatin, BSA (albumin), pea, soy, whey and zein (corn). The protein films were then dissolved at 37° C. in 0.1N HCl with a pH of 1.5 for 90 minutes, after which the pH was adjusted to 6.8 over a time period up to 330 minutes.

The dissolution of the protein films was evaluated using spectrophotometry (absorbance at 280 nm), and plotted as a function of time.

Figure 1:
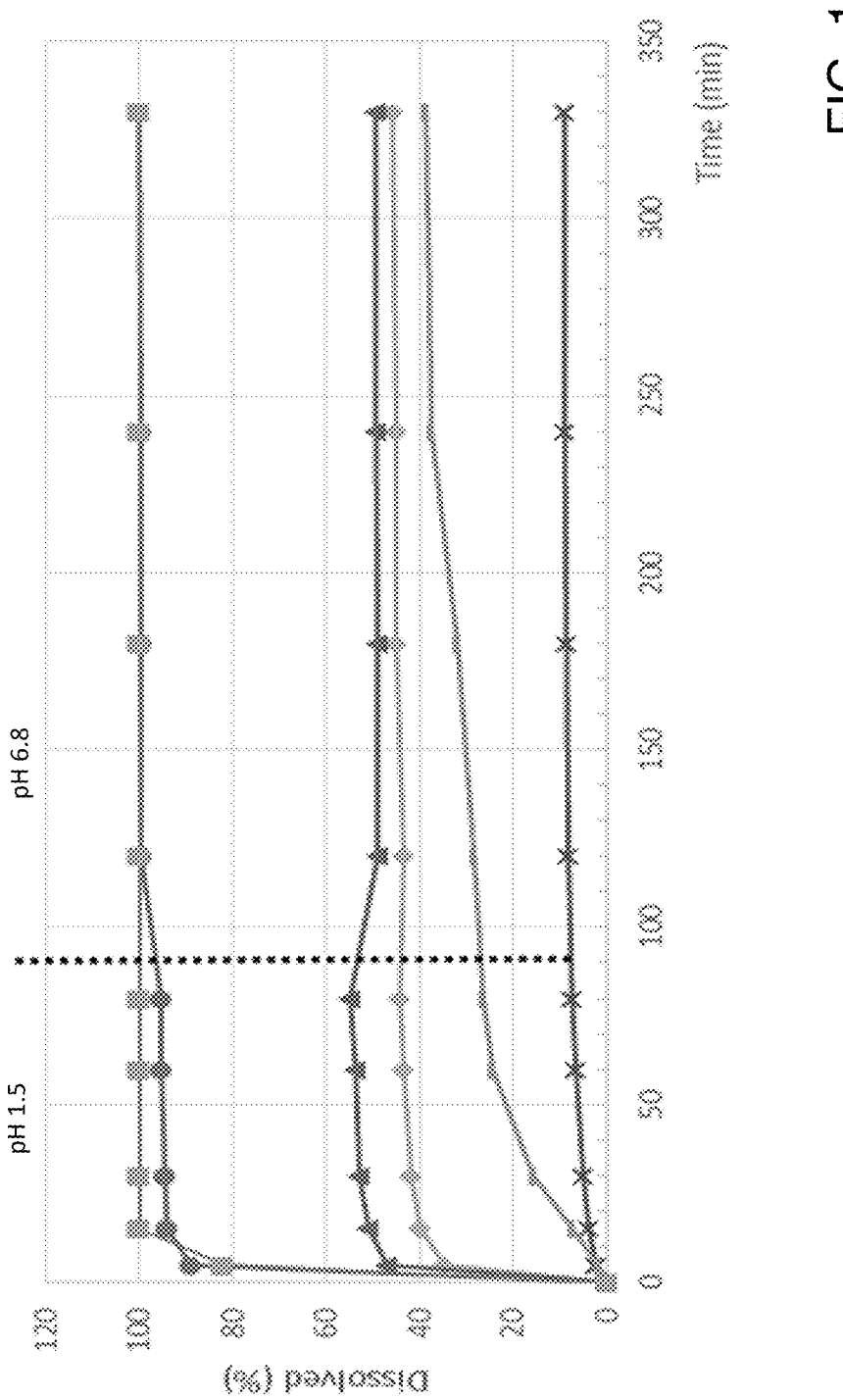
FIG. 1: Graph of a dissolution profile displaying the average dissolution (%) of various protein sources in function of the dissolution time (min) and pH value. The results can be found discussed further in Example 1 and the legend is as follows: square—gelatin; circle BSA (albumin); triangle—pea; diamond—soy; stripe—whey; cross—zein (corn).

The dissolution profiles are set out in FIG. 1, which displays the average dissolution (%) of the various protein sources in function of the dissolution time (minutes) and pH value.

The legend is as follows: square—gelatin; circle—BSA (albumin); triangle—pea; diamond—soy; stripe—whey; cross—zein (corn).

To summarize the results, the gelatin and BSA protein films reach a (near) complete dissolution both in low and high pH values. Pea, soy and whey protein films display an intermediate dissolution level between 40 to 60%. Zein protein films display the lowest dissolution level of the series, reaching about 10%.

Based on the data presented here the gelatin and BSA protein films may be considered the preferred proteins to serve as protein based excipients for fast release formulations. Although several other protein sources, such as pea and soy, also displayed compatibility with such purposes, these proteins and very poorly water soluble films such as those obtained from zein could be used for formulations aimed at sustained or controlled release profiles. In such specific embodiments, wherein a formulation with a lower dissolution rate or level would be desired, the latter protein sources may even be preferred.

Example 2: Determining the Effects of Processing Technology (Spray Drying and Freeze Drying) on the Protein's Structure The effects of the processing technology (i.e., the solvent and drying method) on the native structure of the protein used to obtain a protein based excipient were verified.

For the purposes of the present invention different solvents may be suitable to dissolve a protein composition or hydrolysate thereof, and/or an API; although an organic acid such as formic acid or acetic acid or an organosulfur compound, such as DMSO may be preferred. Likewise, different drying techniques may be suitable for drying a protein solution, an API solution, or an API-protein solution; however, industry standard techniques such as spray drying or freeze drying may be preferred. For the purposes of this experiment, BSA was the protein source; when spray drying was chosen as the drying method formic acid served as the solvent; and freeze drying was chosen as the drying method DMSO served as the solvent.

The native structure of the BSA based excipient was evaluated using gel permeation chromatography, capable of separating the dominant monomeric fraction from the dimeric and trimeric molecules. An increased portion of the latter molecules (i.e., dimers and trimers) serves as an indicator for a structure loss of BSA.

First the effects of formic acid and DMSO as solvents were studied in comparison with a neutral solvent, namely $H_2O$. BSA was dissolved using either formic acid or water and spray dried under identical conditions or was dissolved using DMSO and freeze dried. Next, the obtained BSA based excipient powder was dissolved in a phosphate buffer and analyzed using HPLC-based gel filtration chromatography.

Figure 2:
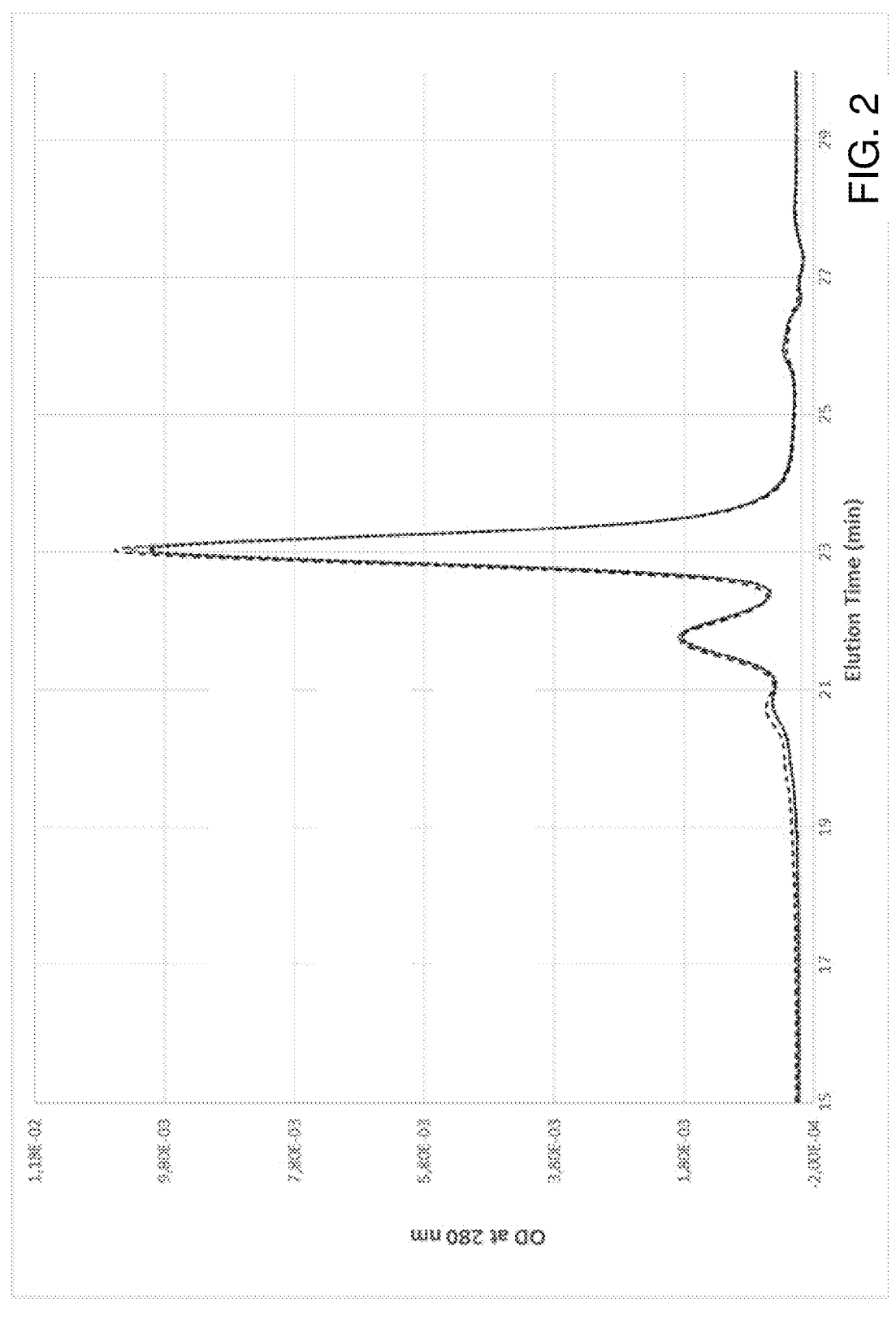
FIG. 2: Gel filtration chromatograms displaying the absorbance (AU) of bovine serum albumin (BSA) in function of elution time (min). The results can be found discussed further in Example 2 and the legend is as follows: full line—BSA spray dried from a 5% (w/v) solution in $H_2O$; dashed line—BSA spray dried from a 5% (w/v) solution in formic acid; dotted line—BSA freeze dried from a 5% (w/v) solution in DMSO.

The results are shown in FIG. 2, which displays the absorbance (AU) of BSA (albumin) in function of time (min). The grey line represents BSA dissolved in $H_2O$; the dashed black line represents BSA dissolved in formic acid, while the dotted line represents BSA dissolved in DMSO. There are no significant differences between the two samples, indicating that neither formic acid nor DMSO does cause denaturation of BSA in comparison with $H_2O$. Similar results are expected for acetic acid.

Next the effect of formic acid was compared for different incubation periods; namely 0, 4, 8 and 24 hours. BSA was dissolved using formic acid and aliquots were pH neutralized at the indicated time intervals, followed by an analysis using HPLC-based gel filtration chromatography.

Figure 3:
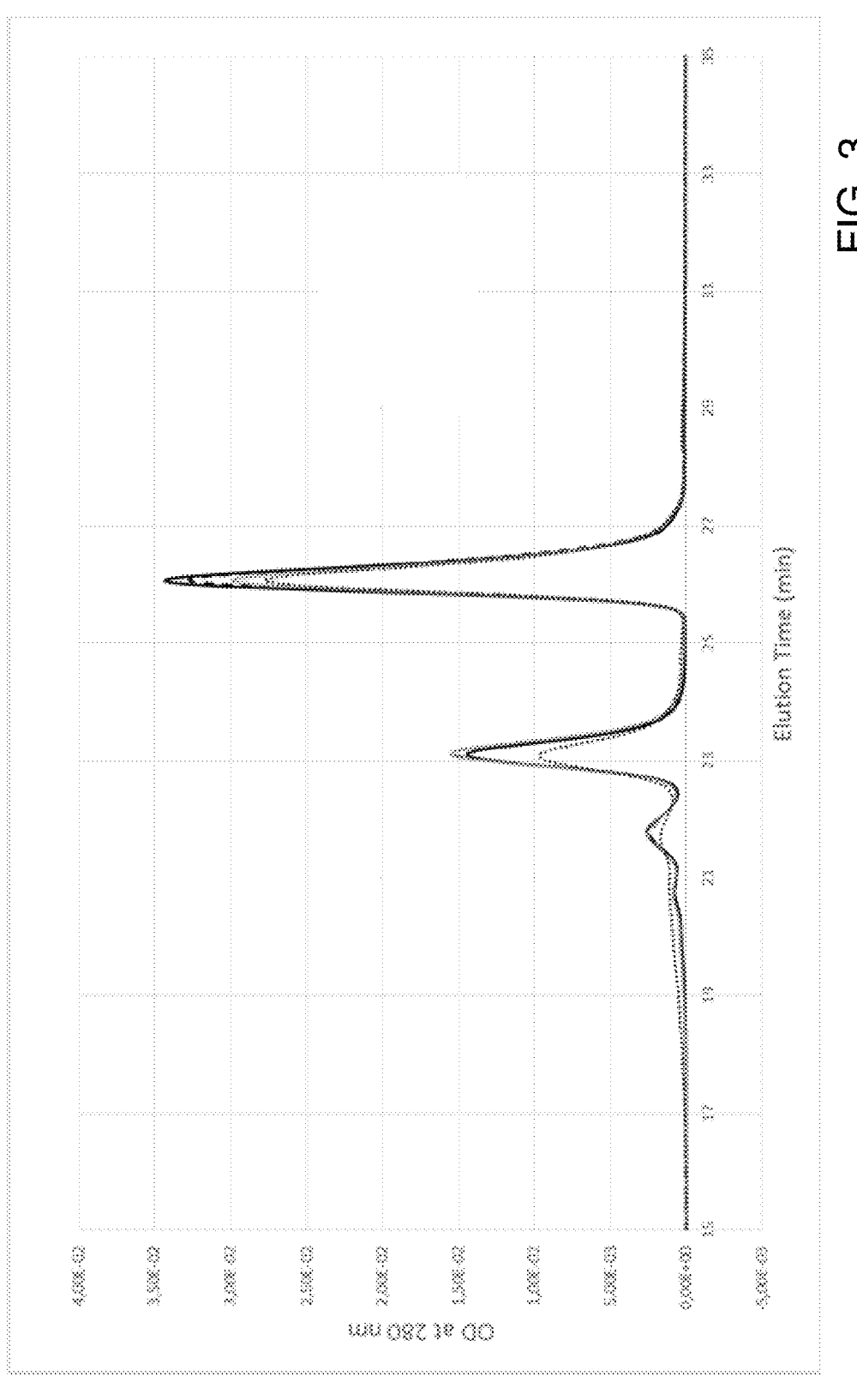
FIG. 3: Gel filtration chromatograms displaying the absorbance (AU) of bovine serum albumin (BSA) in function of time (min) sampled from a solution in formic acid at various time intervals. The results can be found discussed further in Example 2 and the legend is as follows: black full—0 hours; black dashed—4 hours; grey full—8 hours; black dotted—24 hours.

The results are shown in FIG. 3, which displays the absorbance (AU) of BSA (albumin) dissolved in formic acid in function of time (min). The black line represents 0 hours, black dashed line 4 hours, the grey line 8 hours and the dotted black line 24 hours. It can be inferred that 0, 4 and 8 hours of incubation in formic acid does not seem to affect the quaternary structure of BSA significantly. About 24 hours of incubation does reveal some signs of degradation of BSA, as indicated by a higher fraction of larger aggregates, i.e., less monomers present.

In conclusion, the solvent formic acid does not affect BSA's native structure up to an incubation period of 8 hours at room temperature. Similar results were observed for acetic acid, and may be expected from similar organic acids.

Example 3: Verifying the Effects of Processing Technology on the Protein's Biological Activity Example 2 already revealed that up to 8 hours of incubation in formic acid did not seem to affect the quaternary structure of BSA significantly. However, for the purposes of the present invention it is preferred if the protein based excipient at least partially retains its biological activity. More preferably, if it at least partially retains its biological activity in low pH value conditions which are present in the gastrointestinal system. This biological activity may be beneficial for achieving a state of supersaturation and maintaining said supersaturation state for a prolonged time period.

For the following experiment the binding strength of a protein based excipient to a model API was verified. For the purposes of this experiment, BSA was the protein source, Flubendazole was used as the model API, formic acid served as the solvent and spray drying was chosen as the drying method. BSA was first dissolved in formic acid together with various concentrations of Flubendazole (FLU), then the BSA-API solutions were solvent evaporated and the dried formulations were dissolved in buffers of either of the pH values, pH 7.0 (neutral), pH 4.0 (acidic) and pH 1.0 (highly acidic). The fraction of FLU-bound BSA was determined on the basis of tryptophan quenching using a spectrofluorometer, a method to measure equilibrium constants for BSA-API formulations.

Figure 4:
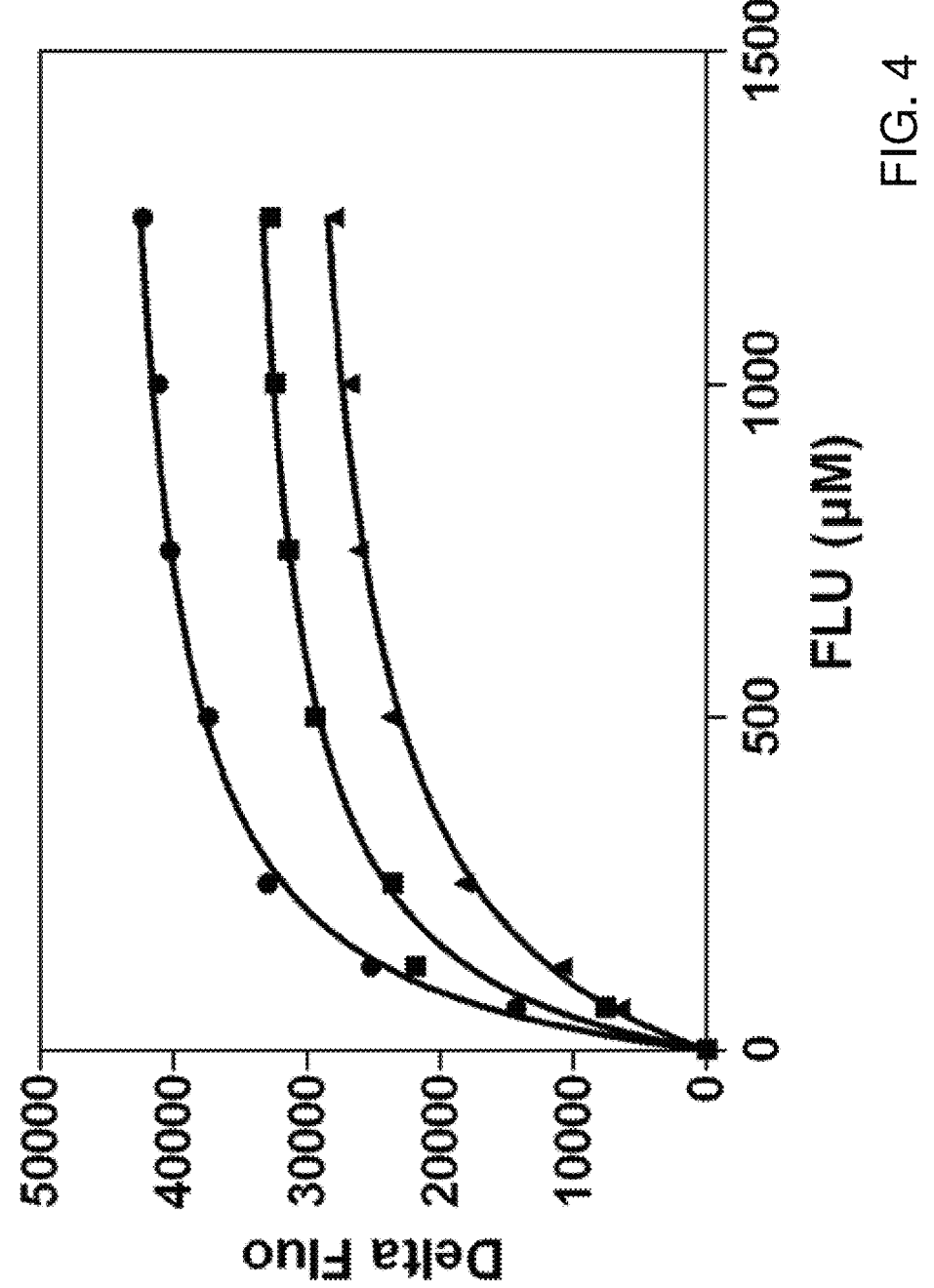
FIG. 4: Binding curves displaying the level of tryptophan quenching (relative A fluorescence units) of bovine serum albumin (BSA) set at various pH values, derived from pH-controlled re-dissolved films casted from a 5% solution in formic acid, in function of the Flubendazole (FLU) Molar concentration ($\mu$M). The results can be found discussed further in Example 3 and the legend is as follows: circle—pH 7.0; square—pH 4.0; triangle—pH 1.0.

The results are shown in FIG. 4, in which the level of FLU-dependent tryptophan quenching is displayed in function of the FLU molar concentration ($\mu$M). The circles represent the data obtained at pH 7.0; the squares represent pH 4.0; and the triangles represent pH 1.0. The binding affinity is observed to decrease two-fold from pH 7.0 to pH 1.0, as deduced by comparing the binding strength, dissociation constant $K_d$, of 116 $\mu$M at pH 7, with the $K_d$ of 234 $\mu$M at pH 1; whereas the dissociation constant $K_d$, at pH 4.0 is in-between with a value of 133 $\mu$M. However, at all pH-values BSA is noted to retain its biological activity (i.e., binding affinity), hence its native conformation at pH 1.0.

In conclusion, although the binding affinity of a BSA based excipient is seen to be reduced at a highly acidic environment resembling the one prevalent in the stomach (i.e. pH 1.0), its biological activity is retained in any studied case. Similar results may be observed for other protein sources (e.g. gelatin) and other API's (e.g. Carbamazepine, Griseofulvin, Phenytoin, Nifedipine, Verapamil, Azithromycin, Nitrofurantoin, Iopanoic acid, Itraconazole, Naproxen).

Example 4: Determining the Effects of a Protein Based Excipient on the Formulation's Supersaturation State Different proteins or protein compositions from various protein sources were prepared in various concentrations to evaluate the extent of the effects of a protein based excipient comprised in a formulation with regards to achieving a supersaturation state and maintaining said supersaturation state. Achieving a high supersaturation may be considered an indicator for an improved bioavailability of an API comprised in said formulation.

The protein based excipients were all based on gelatin extracted from various sources; the raw materials for the gelatin protein composition were extracted from porcine skin or bovine bone and/or a combination thereof; all produced by Rousselot®. Flubendazole was again selected as the model API.

The dissolution profile and supersaturation state (i.e., the available concentration) was tested using a dissolution media which simulates the juice present in the human stomach before (i.e. fasted state) eating food; namely FaSSGF (1.6 pH) available from Bio-relevant®. A suitable method for determining the concentration is Reversed phase High-performance liquid chromatography (RP-HPLC), which separates molecules based on hydrophobicity causing different retention times as they flow out the column. The further working principles of RP-HPLC are known in the art. The RP-HPLC set-up used an Eclipse Zorbax Agilent 5 $\mu$m (4.6×150 mm) column with a flow Rate of 1 ml/min. The injection volume was 20 $\mu$l with the mobile phase containing ACN/TFA 0.1% (55:45) and an elution time of Flubendazole about ±1.9 min. The wavelength for measurements was set at 280 nm.

Prior to the experiments, the solubility of Flubendazole in FaSSGF was determined to serve as the baseline reference value. The reference solution was prepared by bringing an excess of Flubendazole in 8 ml FaSSGF solution. This solution was rotated during 72 hours and a 1 ml sample was taken every 24 hours. These reference samples were filtered through a Polytetrafluoroethylene (PTFE) 0.45 $\mu$m filter to determine the concentration of Flubendazole through the tested RP-HPLC method. The equilibrium concentration was reached whenever the Flubendazole concentration was observed to remain unchanged. Said reference value was 11.2 $\mu$g/ml of Flubendazole in FaSSGF medium.

Next, the effect of the gelatin based excipients on the formulation's supersaturation state was determined. Hence, a gelatin based excipient from various gelatin sources was added to obtain 0.1% protein solutions (8 mg w/v); namely porcine skin gelatins characterized by a Bloom value of 50, 75, and 225 g, bovine bone gelatins characterized by a Bloom value of 150, and 225 g, and gelatin peptides obtained from either porcine skin or bovine bone collagen characterized by an average molecular weight of 5000 Da. As compared to the equilibrium solubility, a twenty fold excess of Flubendazole (225 $\mu$g/ml final concentration) from a formic acid-dissolved concentrated stock solution was added to each solution to probe the time window of supersaturation. All the solutions were rotated and 1 ml samples were taken at the following time intervals: at 5, 15, 30, 60 and 120 minutes. Each sample was filtered through the PTFE 0.45 $\mu$m filter, diluted 1:100 with mobile phase and analyzed using RP-HPLC.

Figure 5:
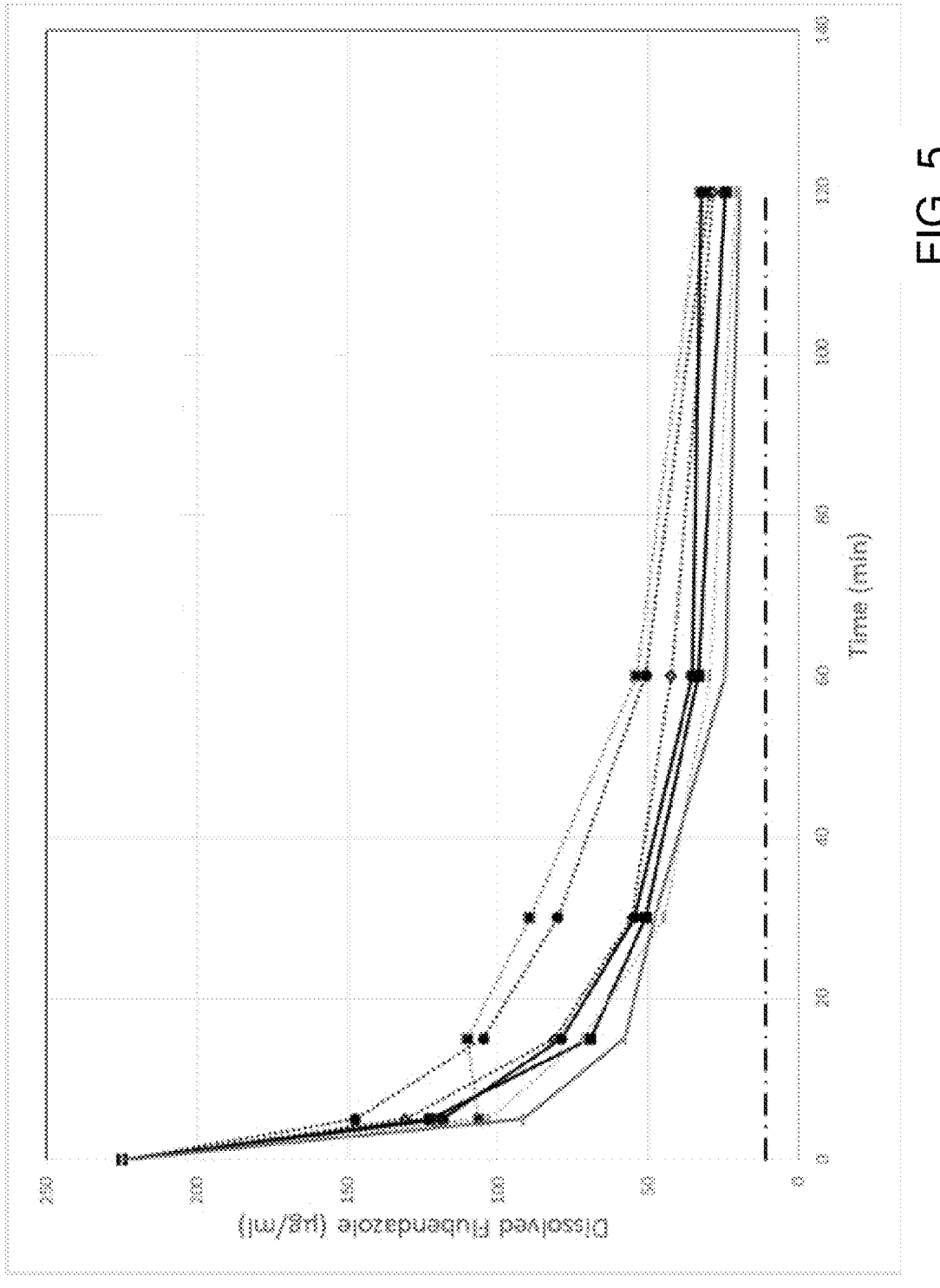
FIG. 5: Graph of a supersaturation profile displaying the average concentration of dissolved Flubendazole (FLU) ($\mu$g/ml) originated from a 225 $\mu$g/ml spike of amorphous FLU (FLU stock dissolved in formic acid) in FaSSGF medium for each series comprising a different gelatin-based excipient in function of the dissolution time (min). The results can be found discussed further in Example 3 and the legend is as follows: circle—pH 7.0; square—pH 4.0; triangle—pH 1.0.

The results are displayed in FIG. 5, which displays the average concentration of Flubendazole ($\mu$g/ml) in function of the incubation time (min) in FaSSGF medium for each formulation comprising a different gelatin based excipient. The high concentrations indicate that a state of supersaturation is reached, and a plateau indicates said supersaturation state is maintained over a prolonged period of time.

In FaSSGF media a degree of supersaturation is maintained for all excipients during the time of the experiment, and characterized by a time-dependent exponential-type decay, with after 2 hours of agitation, the highest concentrations of Flubendazole maintained in the presence of the porcine skin gelatins with low (50, and 75 g) Bloom, and the bovine bone gelatin of high (225 g) Bloom with respectively 32 $\mu$g/ml (3×Cmax), 29 $\mu$g/ml (2,6×Cmax), and 32 $\mu$g/ml (3×Cmax).

In general, the results showed a considerable improvement in the available concentration of the poorly soluble API Flubendazole. All formulations comprising a gelatin based excipient and Flubendazole reached higher Flubendazole concentrations over those observed for the reference samples comprising only Flubendazole. Additionally, certain gelatin based excipients reached even significantly higher Flubendazole concentrations and maintained said high concentrations over a prolonged period of time.

The above results were verified using a protein based excipient obtained from a whey protein composition. For the following experiment two samples of a formulation comprising a whey based protein excipient and Flubendazole were prepared under identical conditions. One sample was kept as physical mixture and one was casted as a solid film. Afterwards both samples were released into 0.1 N HCl at 37° C. to verify and maintain a state of Flubendazole super saturation. Samples were taken at the following time intervals: at 2, 5, 10, 20, 30, 60 and 120 minutes, and analyzed using RP-HPLC.

Figure 6:
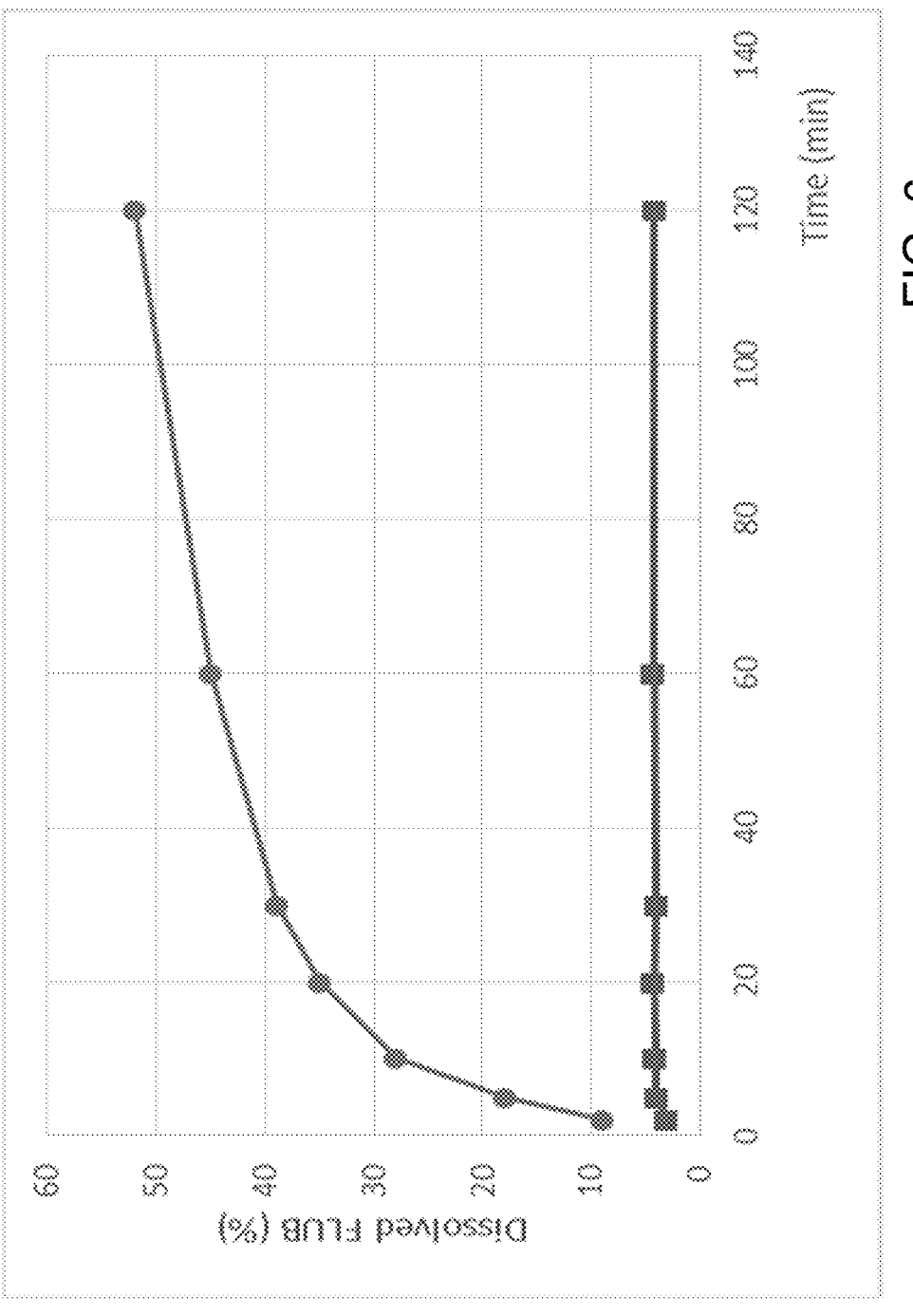
FIG. 6: Graph of a dissolution profile displaying the average dissolution (%) of Flubendazole (FLUB) mixed with a whey protein based excipient in function of the dissolution time (min). The results can be found discussed further in Example 4 and the legend is as follows: square—whey protein FLUB physical mixture; circle—whey protein FLUB film.

The results are displayed in FIG. 6, which displays the average dissolution (%) of Flubendazole (FLUB) mixed with a whey protein based excipient in function of the dissolution time (min). The legend is as follows: square—whey protein Flubendazole physical mixture; circle—whey protein Flubendazole film.

These results clearly demonstrate that formulations comprising a whey protein based excipient and Flubendazole create and maintain Flubendazole super saturation in 0.1 N HCl at 37° C. Moreover, the beneficial effects are exhibited in particular for solvent casted formulations.

As a general conclusion, the results reveal that protein based excipients are in fact capable of promoting a state of supersaturation in a gastrointestinal environment, and may further help maintain said supersaturation state over a prolonged period of time.

These findings suggest that the bioavailability of poorly soluble APIs (e.g. Flubendazole, Carbamazepine, Griseofulvin, Phenytoin, Nifedipine, Verapamil, Azithromycin, Nitrofurantoin, Iopanoic acid, Itraconazole, Ibuprofen, Indomethacin, Glibenclamide, Bicalutamide, Ezetimibe, Aceclofenac, Ketoconazole, Oxfendazole, Ritonavir, Fenofibrate, Cinnarizin, Darunavir, Diazepam, Testosterone undecanoate, or Naproxen) prepared in a formulation further comprising at least one protein based excipient (e.g. BSA, gelatin) may be increased accordingly. Moreover, in case the protein excipient is made from human serum albumin (HSA), the said benefits may yield high API concentrations in physiological media in order to achieve effective clinical performance of injectable formulations of the drug. Indeed, since said formulation is solely comprised of non-allergic protein excipient and API, surfactants and other potentially allergic and/or toxic excipients are avoided leading to a safer product having reduced allergic potential and other side effects.

Example 5: Structural Properties of Formulations Comprising a Gelatin Based Excipient Three gelatin based excipients were retained to further evaluate the structural properties (e.g. solid state and powder particle size) of formulations comprising said excipients after processing; in particular porcine skin gelatin with Bloom=50 g, porcine skin gelatin with Bloom=75 g, and bovine bone gelatin with Bloom=225 g. Flubendazole was again selected as the model API, formic acid served as the solvent and spray drying was chosen as the drying method.

The three gelatin samples were all dissolved in formic acid together with Flubendazole for four different (%/%) ratios; namely, [90-10], [80-20], [70-30] and [60-40] excipient/API (%). Next the protein-API solutions were spray dried under identical conditions to obtain powder formulations with a very high yield. The reference sample to set the standard calibration parameters comprised of gelatin dissolved in formic acid without an API.

For the spray drying apparatus, both spray-drying with a biofluid and an ultrasonic nozzle were tested and yielded similar results. The solid state (i.e., crystalline or amorphous) of the formulations was evaluated using X-ray Powder Diffraction (XPRD) technology. This technique utilizes the constructive interference of X-rays with the crystallographic arrangement to identify the structure and phase formulation of the spray dried powder formulation. The working principles of XRD or XRPD are known in the art. Accordingly, the XRD experiments were carried out using an automated X'pert PRO diffractometer (PANalytical, The Netherlands) equipped with a Cu tube (K$\alpha$ $\lambda$=1.5418 Å) with the generator set at 45 kV and 40 mA. Samples were applied on spinning zero background sample holders. Measurements were performed in a continuous scan mode from 4° to 40° with 0.0167° step size and 400 s per step counting time.

A suitable method for determining the particle size distribution (PSD) of the spray dried powder formulation is dry powder laser diffraction technology. The particle size distributions were determined by measuring the angular variation in intensity of light scattered as a laser beam passed through the powder sample. The working principles of dry powder laser diffraction are known in the art. Accordingly, the excipient powders were dispersed with compressed air at 3 bar through a RODOS dry disperser before sizing with a HELOS laser diffraction sensor (Sympatec, The Netherlands) with a measurement range: 0.9-175 µm. The angular scattering intensity data was subsequently analyzed to calculate the size of the particles responsible for creating the scattering pattern. The particle size is reported as a volume equivalent sphere diameter. The solid state analysis and particle size (PS) determination results for formulations comprising various ratios of a gelatin based excipient (Exc. conc.) and Flubendazole (API conc.) are presented below in table 1.

TABLE 1

| | Structural properties of formulations comprising a gelatin based excipient | | | |
|---|---|---|---|---|
| Excipient | Exc. conc. (%) | API conc. (%) | PS (µm ± 0.01) | Amorph. (yes/no) |
| 50PS30 | 90 | 10 | 15.06 | + |
| | 80 | 20 | 14.03 | + |
| | 70 | 30 | 14.03 | − |
| | 60 | 40 | 13.01 | − |
| 75PS18 | 90 | 10 | 13.58 | + |
| | 80 | 20 | 12.80 | + |
| | 70 | 30 | 13.66 | − |
| | 60 | 40 | 12.27 | − |
| 225LB30 | 90 | 10 | 17.72 | + |
| | 80 | 20 | 22.76 | − |
| | 70 | 30 | 21.02 | − |
| | 60 | 40 | 19.27 | − |

To summarize table 1: the mean particle size (PS) of the formulations comprising a 50PS30 based excipient and Flubendazole is about 14.03 µm; a 75PS18 based excipient and Flubendazole is about 13.1 µm; and a 225LB30 based excipient and Flubendazole is about 20.2 µm; thus the general average PS of gelatin based excipient types is about 15.8 µm.

All formulations comprising gelatin with a relative excipient ratio of 90% were found to be completely amorphous.

However, when the relative excipient ratio was reduced to 70% or below, at least a part of the powder particles were found to be semi-crystalline.

In general a lower PS and substantially amorphous state can be associated with a better solubility and dissolution rates, and thus by extension may help achieve a state of supersaturation easier. Thus in conclusion, the results teach that formulations comprising a higher excipient to API ratio (%/%) may prove further beneficial for the purposes of the present invention. Only the formulations showing a complete amorphous state were retained for further testing of their solubility and dissolution profiles.

Example 6: Structural Properties of (Spray Dried) Formulations Comprising a BSA Based Excipient Similar to example 5, the structural properties of formulations comprising BSA based excipients were evaluated after processing. The raw materials for the BSA protein composition were extracted from bovine origin. Flubendazole was again selected as the model API, formic acid served as the solvent and spray drying was chosen as the drying method. The BSA samples were all dissolved in formic acid together with Flubendazole for four different (%/%) ratios; namely, [90-10], [80-20], [70-30] and [60-40] excipient/API (%). Next the protein-API solutions were spray dried under identical conditions to obtain powder formulations with a very high yield. The reference sample to set the standard calibration parameters comprised of BSA dissolved in formic acid without an API.

The properties were again evaluated using XPRD and dry powder laser diffraction technology; using the same parameters as set out for example 5. The result of both measurements is set out below in Table 2.

TABLE 2

Structural properties of formulations comprising a BSA based excipient

| Excipient | Exc. conc. (%) | API conc. (%) | PS ($\mu$m ± 0.01) | Amorph. (yes/no) |
|---|---|---|---|---|
| BSA | 90 | 10 | 9.58 | + |
| BSA | 80 | 20 | 8.89 | + |
| BSA | 70 | 30 | 8.60 | + |

To summarize Table 2: the mean particle size (PS) of the formulations comprising a BSA based excipient and Flubendazole is about 9.1 $\mu$m. All formulations were found to be completely amorphous, regardless of the relative ratio.

In conclusion, the results teach that formulations comprising a BSA based excipient and an API may prove particularly beneficial for the purposes of the present invention.

Example 7: Dissolution Profiles of (Spray Dried) Formulations Comprising a BSA or Gelatin Based Excipient The formulations from examples 5 and 6 showing an amorphous state were tested for their solubility and dissolution levels; namely porcine gelatin Blooms 50 g or 225 g:FLU (ratios of 80:20%, or 90:10%, respectively), and BSA (70-90%):FLU (30-10%).

For the gelatin-based formulations, the dissolutions were performed in 400 ml HCl 0.1M @ 37° C. over an 80 minutes time period. For the BSA-based formulations, the dissolutions were performed in 400 ml HCl 0.1M @ 37° C. for 90 minutes at which point the pH of the medium was adapted by solid $Na_3PO_4$ to a value of 6.8. The complete dissolution took 5 hours 30 min. All tests were performed in duplicate and samples were taken at 5'; 15'; 30'; 60'; 80' (gelatin based-formulations) or at 5'; 15'; 30'; 60'; 80'; 120'; 180'; 240' and 330' (BSA-based formulations). Afterwards the samples were filtered with 0.45 $\mu$m PTFE filters. The stock solution contained 350 $\mu$g/ml Flubendazole. The standards were prepared from stock solution, diluted in ACN/TFA 0.1% (55:45) and linearity observed between 1 $\mu$g/ml and 350 $\mu$g/ml.

All tests were performed in multiples for statistical purposes; the first series comprised a total of first, 625 mg amorphous solid dispersion containing 20% Flubendazole and 80% pig skin gelatin of Bloom=50 g; second, 625 mg amorphous solid dispersion containing 20% Flubendazole and 80% pig skin gelatin of Bloom=225 g; and third, 625 mg powder containing 20% Flubendazole and 80% pig skin gelatin of Bloom=50 g (i.e. physical mixture). The second series comprised a total of first, 1250 mg amorphous solid dispersion containing 10% Flubendazole and 90% BSA; second, 625 mg amorphous solid dispersion containing 20% Flubendazole and 80% BSA; third, 416 mg powder containing 30% Flubendazole and 70% BSA; and fourth, 625 mg powder containing 20% Flubendazole and 80% BSA (i.e. physical mixture).

The dissolution profiles were determined using RP-HPLC, similar to example 4. The RP-HPLC set-up used an Eclipse Zorbax Agilent 5 $\mu$m (4.6×150 mm) column with a flow Rate of 1 ml/min. The injection volume was 20 $\mu$l with the mobile phase containing ACN/TFA 0.1% (55:45) and an elution time of Flubendazole about ±1.9 min. The wavelength for measurements was set at 280 nm.

Figure 7A:
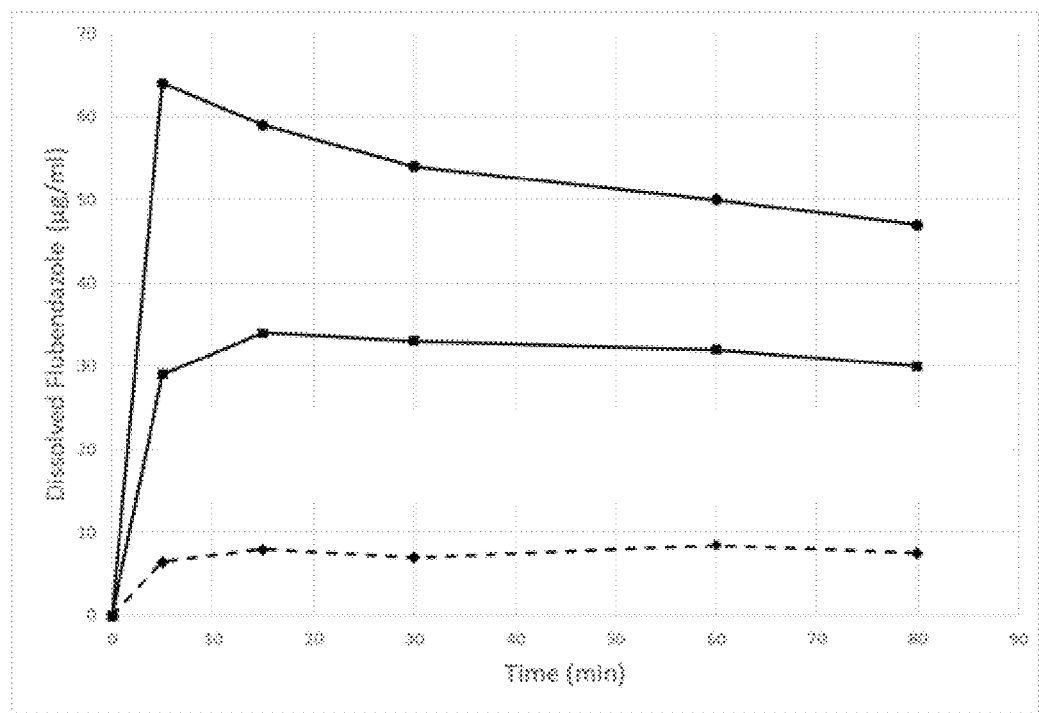
FIGS. 7A-7B: Graphs of dissolution profiles (in 0.1 N HCl, pH 1.5) displaying (FIG. 7A) the dissolved Flubendazole (FLU) concentration $C_{Flub}$ ($\mu$g/ml) or (FIG. 7B) the dissolved percentage of total FLU (%) for each series of protein-based (spray dried) formulations in function of the dissolution time (min); the displayed values represent the calculated averages for each experiment. The results can be found discussed further in Example 7 and the legend is as follows: The full line marked with a circle corresponds to a spray dried formulation comprising 80% pig skin gelatin (Bloom=50 g) and 20% FLU; the full line marked with a square corresponds to a spray dried formulation comprising 90% pig skin gelatin (Bloom=225 g) and 10% FLU; a dashed line corresponds to a formulation comprising a physical mixture of 80% pig skin gelatin (Bloom=50 g) and 20% FLU.
Figure 7B:
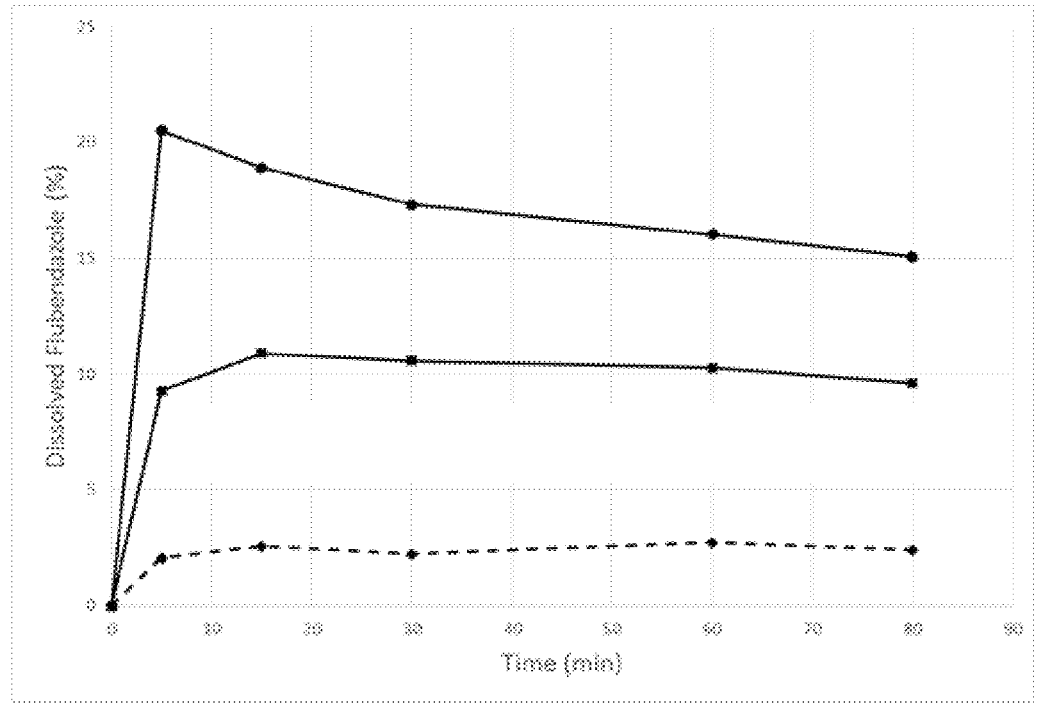
Figure 8A:
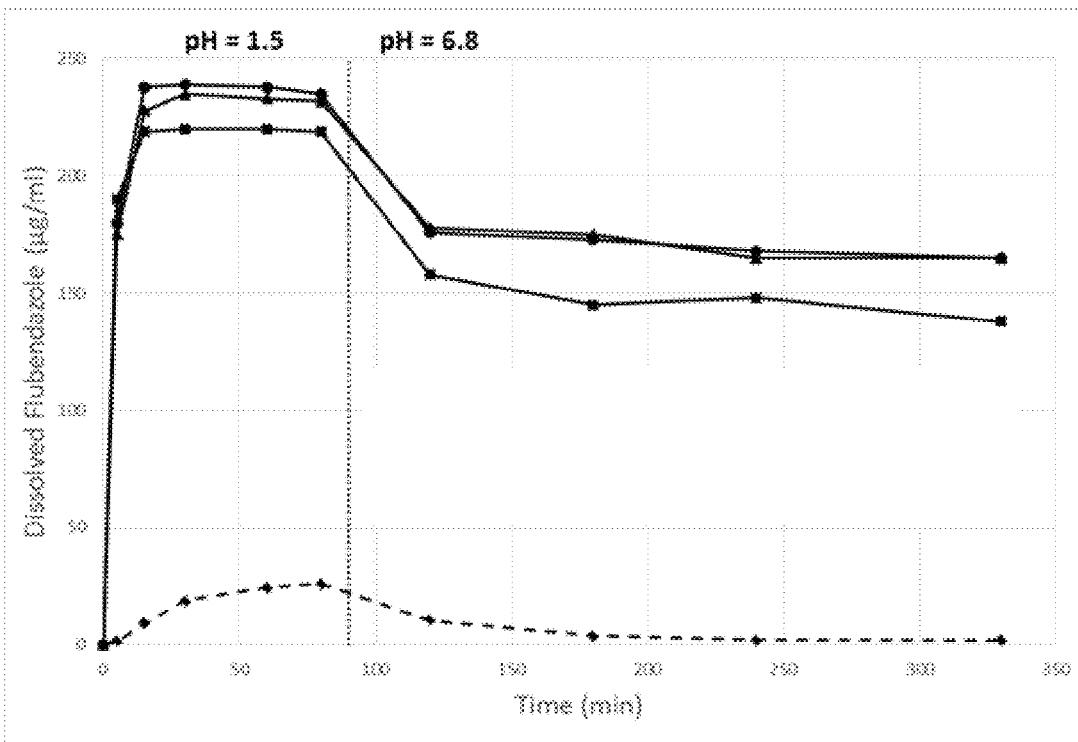
FIGS. 8A-8B: Graph of dissolution profiles (first 90 minutes in 0.1 N HCl, pH 1.5, then 250 minutes in $PO_4^{2-}$ buffer, pH 6.8 ($Na_3PO_4$ addition)) displaying (FIG. 8A) the dissolved Flubendazole (FLU) concentration $C_{Flub}$ ($\mu$g/ml) or (FIG. 8B) the dissolved percentage of total FLU (%) for each series of BSA-based (spray dried) formulations in function of the dissolution time (min); the displayed values represent the calculated averages for each experiment. The results can be found discussed further in Example 7 legend is as follows: The full line marked with a circle corresponds to a spray dried formulation comprising 90% BSA and 10% FLU; the full line marked with a triangle corresponds to a spray dried formulation comprising 80% BSA and 20% FLU; the full line marked with a square corresponds to a spray dried formulation comprising 70% BSA and 30% FLU; a dashed line corresponds to a formulation comprising a physical mixture of 80% BSA and 20% FLU.
Figure 8B:
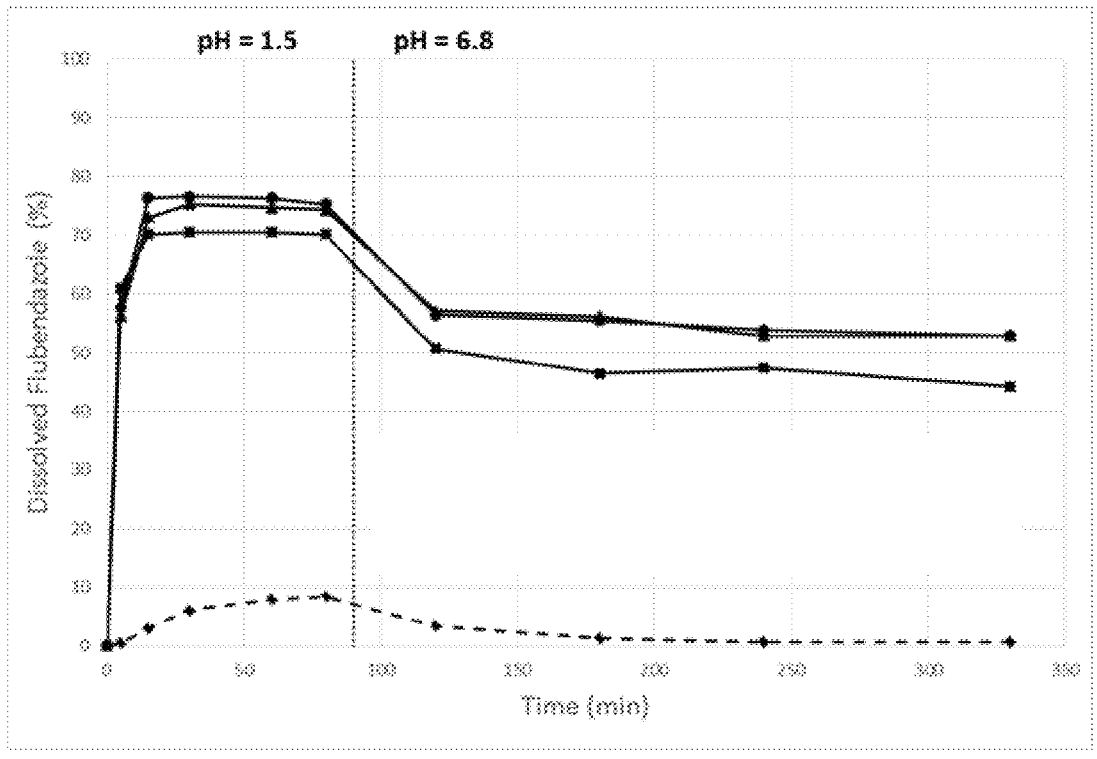

The dissolution profiles are set out in FIGS. 7A-7B and FIGS. 8A-8B. FIG. 7A is a graph of a dissolution profile displaying the Flubendazole concentration $C_{Flub}$ ($\mu$g/mi) for each series of gelatin-based formulations in function of the dissolution time (min); the displayed values represent the calculated averages for each experiment. FIG. 7B is a graph of a dissolution profile displaying the average percentage release of Flubendazole (%) for each series of gelatin-based formulations in function of the dissolution time (min); the displayed values represent the calculated averages for each experiment. FIG. 8A is a graph of a dissolution profile displaying the Flubendazole concentration $C_{Flub}$ ($\mu$g/ml) for each series of BSA-based formulations in function of the dissolution time (min); the displayed values represent the calculated averages for each experiment. FIG. 8B is a graph of a dissolution profile displaying the average percentage release of Flubendazole (%) for each series of BSA-based formulations in function of the dissolution time (min); the displayed values represent the calculated averages for each experiment.

The legend of FIGS. 7A-7B is as follows: The full line marked with a circle corresponds to a spray dried formulation comprising 80% pig skin gelatin (Bloom=50 g) and 20% FLU; the full line marked with a square corresponds to a spray dried formulation comprising 90% pig skin gelatin (Bloom=225 g) and 10% FLU; a dashed line corresponds to a formulation comprising a physical mixture of 80% pig skin gelatin (Bloom=50 g) and 20% FLU. The legend of FIGS. 8A-8B is as follows: The full line marked with a circle corresponds to a spray dried formulation comprising 90% BSA and 10% FLU; the full line marked with a triangle corresponds to a spray dried formulation comprising 80% BSA and 20% FLU; the full line marked with a square corresponds to a spray dried formulation comprising 70%

BSA and 30% FLU; a dashed line corresponds to a formulation comprising a physical mixture of 80% BSA and 20% FLU.

Generally for all protein-based excipients, the results from the dissolution tests showed a considerable improvement in the dissolution of the poorly soluble API Flubendazole in a spray dried amorphous solution. A plateau is indicative of a supersaturation state being achieved and maintained over a prolonged period of time. Hence, an improved Flubendazole solubility was observed as characterized by a faster dissolution rate, as indicated by the initial slope, and a higher dissolution level, as indicated the higher maximal Flubendazole concentration.

For all three ratios (90-80-70%) tested in the series of BSA-dependent formulations, the $C_{max}$ (i.e., maximal Flubendazole concentration) values were all observed to increase to peak in low pH values, and decrease in higher pH, although still remaining high.

More specifically, the formulations comprising high ratios of BSA based excipient, i.e. 90 and 80%, were seen to reach very high release rates of around 80% and a $C_{max}$ of 240 µg/ml. The formulation comprising a lower, 70% ratio of BSA based excipient showed slightly diminished results with a peak release rate of around 70% and $C_{max}$ of 220 µg/ml; however, the latter results are still several, almost 20 times higher than any comparable reference value.

The cause for the relative improvement is found that BSA binds Flubendazole with a bond strength $K_d$ of about ~234 µM at a pH value of 1, about ~133 µM at a pH value of 4, and about ~116 µM at a pH value of 7, values generally corresponding to the pH profile associated with the passage of an oral dosage form through the GIT. This strongly indicates that BSA will interact with Flubendazole in both the stomach and small intestines, thereby dissolving Flubendazole to almost 20 times the reference values.

Thus in conclusion it is revealed that protein based excipients are in fact capable of promoting a state of supersaturation in a gastrointestinal environment, and may further help maintain said supersaturation state over a prolonged period of time. These findings suggest that the bioavailability of poorly soluble APIs (e.g. Flubendazole, Carbamazepine, Griseofulvin, Phenytoin, Nifedipine, Verapamil, Azithromycin, Nitrofurantoin, Iopanoic acid, Itraconazole, Ibuprofen, Indomethacin, Glibenclamide, Bicalutamide, Ezetimibe, Aceclofenac, Ketoconazole, Oxfendazole, Ritonavir, Fenofibrate, Cinnarizin, Darunavir, Diazepam, Testosterone undecanoate, or Naproxen) prepared in a formulation further comprising at least one protein based excipient may be increased accordingly. Moreover, in case the protein excipient is made from human serum albumin (HSA), the said benefits may yield high API concentrations in physiological media in order to achieve effective clinical performance of injectable formulations of the drug. Indeed, since said formulation is solely comprised of non-allergic protein excipient and API, surfactants and other potentially allergic and/or toxic excipients are avoided leading to a safer product having reduced allergic potential and other side effects.

Example 8: Combinations of the Protein Based Excipient with Polymer Based Excipients and Structural Properties of Spray Dried Formulations Comprising Said Combinations The structural properties of different formulations comprising first an API and second a polymer based excipient, or a protein based excipient, or a combination of a protein and a polymer based excipient were analyzed and compared.

The polymer based excipient chosen was Soluplus®; produced by Badische Anilin und Soda Fabrik (BASF). The protein based excipients were all based on gelatin extracted from various sources; the raw materials for the gelatin protein composition were extracted from porcine skin or bovine bone and/or a combination thereof; all produced by Rousselot®. Flubendazole was again selected as the model API.

Different solid dispersions were produced using the methods as disclosed previously (e.g. spray drying). Afterwards their properties were again evaluated using XRD using the same parameters as set out for example 5.

Figure 9:
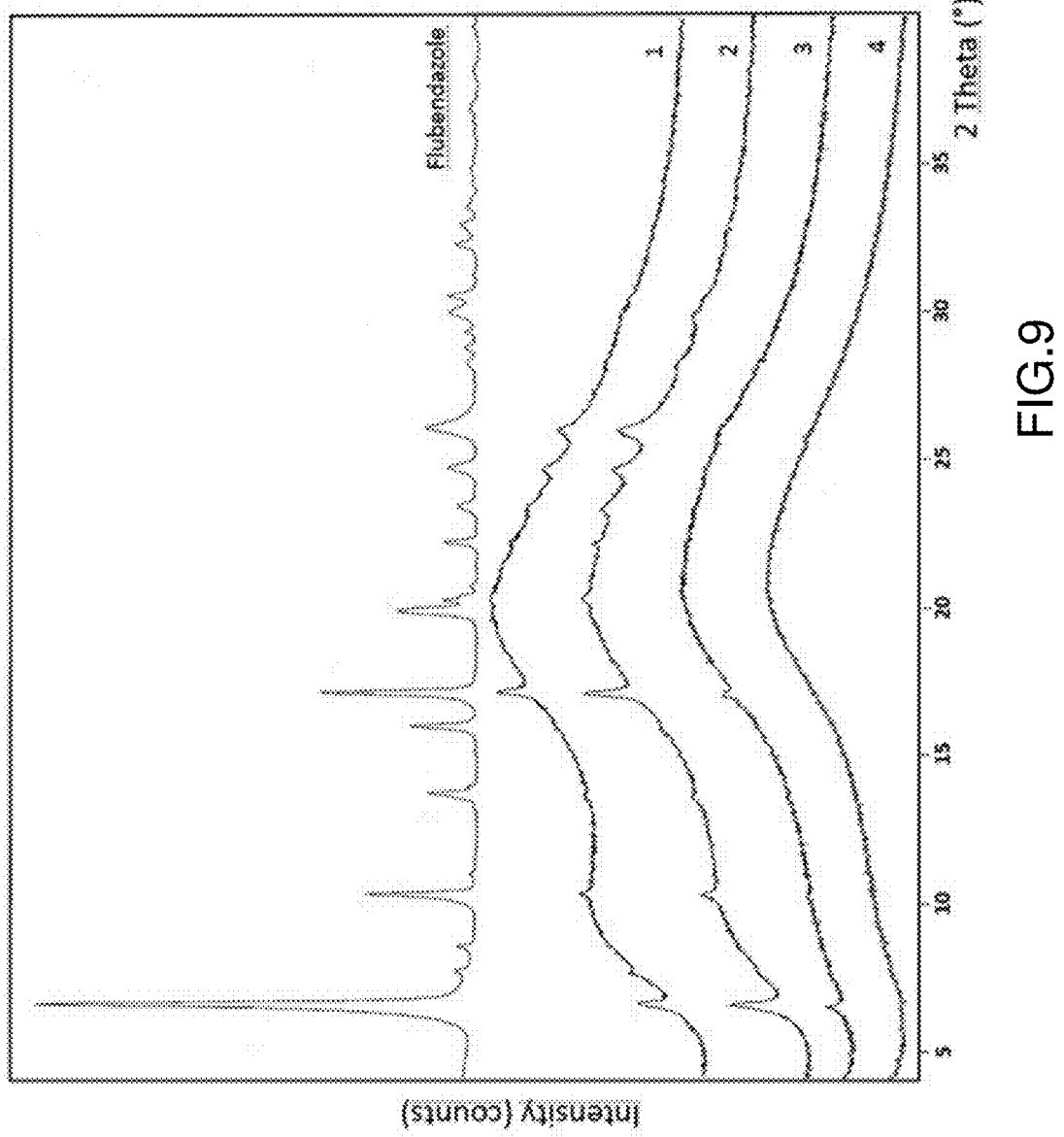
FIG. 9: Graph of XRD patterns of the formulations comprising (1) 80% Soluplus®; 20% Flubendazole (FLU); (2) 40% polymer: 40% gelatin: 20% FLU; (3) 10% polymer.

The results are set out in FIG. 9, which shows a graph of XRD patterns of the formulations comprising (1) 80% Soluplus®: 20% Flubendazole (FLU); (2) 40% polymer: 40% gelatin: 20% FLU; (3) 10% polymer: 70% gelatin: 20% FLU; (4) 80% gelatin: 20% FLU (4).

It is revealed that the formulation comprising the only polymer based excipient (ref 1) is in fact not completely amorphous, unlike the formulation comprising only the protein based excipient (ref. 4) which is completely amorphous. However, by combining the polymer based excipient with a protein based excipient in a common formulation the degree of amorphous state may be increased, and is also observed to improve with the increased relative ratio of protein based excipient to polymer based excipient.

Thus in conclusion it is revealed that protein based excipients are in fact capable of further promoting the amorphous state in combination with an API and a polymer based excipient. The combined formulations comprising a BSA based excipient, a polymer based excipient and an API may prove particularly beneficial for the purposes of the present invention.

Example 9: Verifying Compatibility with Poorly Soluble APIs

Different poorly soluble APIs were selected to evaluate the effects of a protein based excipient as a solubility enhancer. First, a selection was made of various APIs belonging to Class II (i.e. poorly soluble, highly permeable) that were considered most representative for their class. For each of the API a formulation was produced in combination with an excipient, which was afterwards film casted for testing. The optimal API/excipient concentration was selected based on the results from Example 4, that is, each formulation comprised 20% API and 80% BSA (w/w). The following API were selected: Ibuprofen, Indomethacin, Naproxen, Phenytoin, Nifedipine, Griseofulvin, and Verapamil.

Additionally, for each formulation the solvent system was adjusted to achieve optimal dissolution for mixing, drying and casting of the formulation. Particular care was taken to achieve a faster solution of each of the selected API without risking any adverse effects on their functionality. For Indomethacin the preferred solvent system was found to be a mixture of 25% formic acid (FA), 50% acetic acid (AA) and 25% Dichloromethane (DCM); for Naproxen of 100% FA; for Phenytoin of 25% FA, 25% AA and 50% acetone; for Nifedipine of 100% FA; for Verapamil of 100% FA; for Griseofulvin 100% FA; and for Ibuprofen of 15% FA and 85% AA.

The results of the solubility test for each formulation are found displayed in FIGS. 10-16; in particular Ibuprofen (FIG. 10); Indomethacin (FIG. 11); Naproxen (FIG. 12);

Phenytoin (FIG. 13), Nifedipine (FIG. 14); Verapamil (FIG. 15) and Griseofulvin (FIG. 16). The dissolution was again tested in two pH media: the first period starting from 0 min up to 90 min represents measurement done at a pH of 1.5, and the second period running from 90 min onwards repevaporation of the solvent system. The operational parameters, however, were kept constant for sake of comparison according to the following spray drying set-up: airflow of 0.3 m³/min, pump speed of 60%, nozzle air supply around liquid of 8.0 l/min, and a bi-fluid nozzle size of 0.4 mm.

TABLE 3

| production parameters for Vemurafenib/Itraconazol (API) with BSA (excipient) | | | | | | |
|---|---|---|---|---|---|---|
| Process parameters | Parameter values | | | | | |
| Concentrations API/BSA (w/w) | Sample 1: 30%/70% | Sample 2: 30%/70% | Sample 3: 30%/70% | Sample 4: 40%/60% | Sample 5: 50%/50% | Sample 6: 30%/70% |
| Solvent system (v/v) | 100% FA | 80% meth 20% FA | 100% FA | 80% meth 20% FA | 80% meth 20% FA | 100% FA |
| Temp air (° C.) | 140 | 140 | 140 | 140 | 140 | 200 |
| Temp drying chamber (° C.) | 65.4-67.3 | 71.5-71.8 | 80.3-95.8 | 73.5-76.0 | 73.5-79.3 | 104-110.7 |
| Temp before cyclone (° C.) | 43.0-46.0 | 44.9-45.7 | 46.9-59.0 | 44.6-48.9 | 46.5-50.7 | 58.2-67.1 |
| Pressure cyclone (bar) | 21.1-22.6 | 20.3-20.2 | 21.0-20.9 | 20.8-20.9 | 20.6 | 22.1-19.4 | resent measurements performed at a pH of 7.2; the pH was verified during each period. In each of the Figs. the dotted line visually represents the pH transition.

The results show an improved to greatly improved dissolution for all formulations when casted as films in comparison with the powder form of the API. As a general conclusion, the results reveal that protein based excipients are in fact capable of enhancing the solubility of Class II API in a gastrointestinal environment, which may further help maintain a supersaturation state over a prolonged period of time. Moreover, when taking into account that for a Class II API a direct correlation between (in-vitro) solvation and (in-vivo) bioavailability has been scientifically documented, it is expected that the solubility enhancing effects of the excipient will likely also provide bioavailability enhancing effects to the Class II API. Moreover, in case the protein excipient is made from human serum albumin (HSA), the said benefits may yield high API concentrations in physiological media in order to achieve effective clinical performance of injectable formulations of either BCS class II or IV drugs. Indeed, since said formulation is solely comprised of non-allergic protein excipient and API, surfactants and other potentially allergic and/or toxic excipients are avoided leading to a safer product having reduced allergic potential and other side effects.

Example 10: Determining Optimal Production Parameters for Solid Dispersion

The development of amorphous solid dispersions for an API with BSA as excipient was tested by producing samples via spray drying with varying production parameters. Two API were selected from the Class II API group to serve as model API; namely Vemurafenib and Itraconazol. For each formulation six samples were produced, thus obtaining a total of 12 samples.

The varying production parameters are found listed in Table 3, and contain the different API/excipient concentrations (w/w), in particular formulations comprising from at least 30% API to 70% BSA, up to 50% API to 50% BSA; different solvent systems, in particular formic acid (FA) or a mixture comprising formic acid (FA) and methanol (meth); and different spray drying temperatures, adjusted to the No processing issues were encountered during the spray drying of the samples reflecting in good processing yields (>83% for Vemurafenib and >95% for Itraconazol). It was, however, noted that Itraconazol required a higher level of agitation to achieve a 100% dissolution in comparison with Vemurafenib. After production of the formulations as solid dispersions, several tests were performed to evaluate the physical properties of the each sample, the results of which are found summarized below.

First, for the samples comprising Vemurafenib:

A Differential Scanning Calorimetry (DSC) method was used for the determination of the amorphicity of the films. The samples with 10% and 20% API (ref. sample 1, 2, 4 and 5) demonstrate the most promising DSC results, with no crystal melt peak present.

The assay values were determined using HPLC. For all six samples good assay values between 89-103% were observed. To verify the sample preparation procedure, a spiked placebo sample was prepared containing 10/90% w/w API/BSA. The spiked amount of API could be retrieved, therefore sample preparation was deemed suitable.

An accelerated screening stability test indicated that all samples demonstrated nice texture and good flow when stored for one month at 25° C. and 60% room humidity (RH), however, some agglomeration was observed at 40° C. and 75% RH.

Second, for the samples comprising Itraconazol:

All six samples demonstrated promising DSC results, with no melt peak present.

For all six samples assay values between 88-91% were measured.

All samples demonstrated nice texture and good flow when stored for one month at 25° C. and 60% RH, however, some agglomeration was observed at 40° C. and 75% RH.

Example 11: Comparative Dissolution Testing

The bioavailability of spray dried powders of an API in presence of BSA as excipient was tested using the optimal parameters selected from Example 9. Four samples were manufactured with two different API, namely Vemurafenib and Itraconazol, with a varying API/excipient concentrations (w/w %), For the Vemurafenib/BSA formulation: Sample 1 containing 10% Vemurafenib (spray dried powder) and 90% BSA (±8000 mg) was produced using the corresponding operational parameters of Sample 1 from Example 10, and Sample 2 containing 20% Vemurafenib and 80% BSA (±4000 mg)), was produced using the corresponding operational parameters of Sample 2 from Example 10. Additionally, the results were compared with those of a commercially available product containing Vemurafenib (Brand name: Zelboraf 240 mg film-coated tablets), which was exposed to the same testing conditions and served as the comparator reference.

For the Itraconazol/BSA formulation: Sample 1 containing 30% Itraconazol (spray dried powder) and 70% BSA (±1111 mg) was produced using the corresponding operational parameters of Sample 2 from Example 10, and Sample 2 containing 40% Itraconazol and 60% BSA (±833 mg) was produced using the corresponding operational parameters of Sample 4 from Example 10. Similarly, the results were compared with those of a commercially available product containing Itraconazol (Brand name: Sporanox 100 mg capsules), which was exposed to the same testing conditions and served as the reference.

The comparative dissolution testing was executed in a two stage dissolution method using HPLC method with UV detection (302 nm) with the following operational conditions: Kromasil 100-5C18—250×4.6 mm; 30° C. temperature; 1 mL/min flow rate; 10 µL Injection volume. To simulate the most expected solution environment the dissolution test was executed at the physiologically most relevant pH of 1.2 (HCl buffer) and 7.2 (USP phosphate buffer). The first period starting from 5 min up to 90 min represents measurement performed at pH 1.2, and the second period running from 95 min up to 150 min represent measurements done at pH 7.2; the pH was verified during each period.

The dissolution results for Vemurafenib are presented in FIG. 17. In general the two different spray dried powders have very similar dissolution profiles. The squares represent the results for sample 1 (10% Vemurafenib and 90% BSA); the triangles for sample 2 (20% Vemurafenib and 80% BSA); and the diamonds represent the Zelboraf reference sample. The dissolution profiles indicate a superior dissolution behavior both at pH 1.2 and 7.2, in comparison with the reference sample (ref. Zelboraf).

The dissolution results for Itraconazol are presented in FIG. 18. The squares represent the results for sample 1 (30% Itraconazol and 70% BSA); the triangles for sample 2 (40% Itraconazol and 60% BSA); and the diamonds represent the Sporanox reference sample Similar to Vemurafenib, the dissolution profiles indicate a superior dissolution behavior both at pH 1.2 and 7.2, in comparison with the reference sample (ref. Sporanox).

Example 12: Improving Wettability of Spray Dried Formulations

When performing Examples 10 and 11 it was observed that certain APIs having a poor wettability, such as Itraconazole, require a high level of agitation (e.g. stirring) to achieve a 100% dissolution when using formic acid as a solvent for processing into (amorphous) solid dispersions. The addition of a hydrophilic carrier to the formulation resolved this problem.

To determine the optimal amount different formulations were spray dried using formic acid as solvent. PEG 10K was selected to serve as hydrophilic carrier, BSA was selected as the excipient, and Itraconazole as the model API. Approximately 5 ml of formic acid was weighed for every solution together with a varying degree of PEG 10K to form a total of 8 samples. Sample 1 contained 80% BSA and 20% Itraconazole; Sample 2 contained 70% BSA, 20% Itraconazole and 10% PEG 10K; Sample 3 contained 60% BSA, 20% Itraconazole and 20% PEG 10K; Sample 4 contained 50% BSA, 20% Itraconazole and 30% PEG 10K; Sample 5 contained 60% BSA, 30% Itraconazole and 10% PEG 10K; Sample 6 contained 50% BSA, 30% Itraconazole and 20% PEG 10K; Sample 7 contained 40% BSA, 30% Itraconazole and 30% PEG 10K; and Sample 8 contained 40% BSA, 40% Itraconazole and 20% PEG 10K.

FIG. 19 shows a graph of a dissolution profile displaying the average dissolution (%) of the listed formulations without any agitation or stirring in function of the dissolution time (min). The average dissolution (%) at 15 min and at 120 min was measured and is further presented as block diagrams in FIG. 20 for ease of comparison.

As a general conclusion the addition of a hydrophilic carrier greatly improves the wettability of the spray dried formulations. Substituting too much BSA for HC however starts compromising the attainable levels of super saturation.

Example 13: Structural Properties of (Freeze Dried) Formulations Comprising a Gelatin Based Excipient The development of amorphous solid dispersions for an API with gelatin as excipient was tested by producing samples via freeze drying with varying production parameters. Ten poorly soluble API were selected from the Class II API group to serve as model API; namely Carbamazepine, Cinnarizine, Darunavir (ethanolate), Diazepam, Fenofibrate, Griseofulvin, Indomethacin, Ketoconazole, Naproxen, and Nifedipine. The protein based excipients were all based on gelatin extracted from porcine skin (Bloom=50 g); all produced by Rousselot®.

Different solid dispersions were produced using freeze drying. For each model API a set of six samples was created, namely sample 1 (ref: pure), which contained a pure API sample serving as reference, and then five formulations comprising the API and gelatin: sample 2 containing 40% API and 60% gelatin (ref: mean 40%); sample 3 containing 30% API and 70% gelatin (ref: mean 30%); sample 4 containing 20% API and 80% gelatin (ref: mean 20%); sample 5 containing 10% API and 90% gelatin (ref: mean 10%); and sample 6 containing 5% API and 90% gelatin (ref: mean 5%).

The solutions were prepared using dimethyl sulfoxide (DMSO) as solvent. For each of the APIs (see also FIG. 1 and Example 1), amorphous solid dispersions of different drug loading (5%, 10%, 20%, 30% and 40%—calculated as $(mass_{API}/mass_{gelatin\ 50PS})*100$) were prepared. In order to achieve this, the different ratios of API over gelatin 50PS were dissolved in DMSO for all API. 1 mL of DMSO was used for every 100 mg of gelatin 50PS present, except for Cinnarizine 10% (2 mL), 20% (3 mL), 30% (4 mL), 40% (4 mL), Itraconazole 10% (2 mL), 20% (3 mL), 30% (4 mL), 40% (4 mL) and Ketoconazole 20% (2 mL), 30% (2 mL) and 40% (2 mL). For these particular API more DMSO was needed to improve the solubility.

Next, freeze drying was used to produce (amorphous) solid dispersions. Each of the solutions was initially frozen at −26° C. in closed plastic recipients, maximizing the solutions' surface areas, and subsequently kept at approximately −26° C. temperature for at least 24 h in a freezer. During this procedure the light sensitive compounds such as cinnarizine, ketoconazole and nifedipine were protected from light using Aluminum paper. In a next step, each frozen sample was transferred (while kept on ice) to an ALPHA 1-4 LSC, CHRIST. freeze-dryer obtained from Martin Christ Gefriertrocknungsanlagen GmbH (Osterode am Harz, Germany). There, plastic recipients were opened, covered with self-perforated (needle) para film and placed on the freeze-drying shelves. The freeze-dryer was then closed and the following operational conditions were maintained for seven consecutive days: −85° C. at 0.008 mbar. After seven days, the formulations were gathered from the freeze-dryer and prepared experimental analysis.

Once gathered, the structural properties of the formulations were evaluated using XRD using the same parameters as set out for example 5.

Two exemplary results were selected and presented in FIG. 21 and FIG. 22, which shows a graph of XRD patterns of the formulations comprising Indomethacin and Darunavir (ethanolate), respectively. For FIG. 21 in particular, the bottom line represents sample 1 (pure Indomethacin) and serves as reference, next, from the bottom up, the following lines represent sample 6 (mean 5%), sample 5 (mean 10%), sample 4 (mean 20%), sample 3 (mean 30%), and sample 2 (mean 40%), respectively, Similarly for FIG. 22, the bottom line represents sample 1 (pure Darunavir), next, from the bottom up, the following lines represent sample 6 (mean 5%), sample 5 (mean 10%), sample 4 (mean 20%), sample 2 (mean 40%), and sample 3 (mean 30%), respectively, The remaining eight model API were also evaluated and showed similar results.

It is revealed that all formulations comprising an API together with gelatin as a protein based excipient are substantially to completely amorphous, unlike the reference sample comprising only the API (cfr. 4), which displays numerous traces of crystallinity.

Thus in conclusion it is revealed that protein based excipients are in fact capable of further promoting the amorphous state in combination with an API. It is also revealed that freeze drying is a suitable method to produce amorphous solid dispersions for the former, and that DMSO is a particularly well suited solvent for freeze drying.

Example 14: Dissolution Profiles of (Freeze Dried) Formulations Comprising a Gelatin Based Excipient Different poorly soluble APIs were selected from the class II API group to evaluate the effects of gelatin as a protein based excipient for enhancing the solubility. The ten samples produced according to the method detailed in Example 13 were selected for further testing; namely, Carbamazepine, Cinnarizine, Darunavir (ethanolate), Diazepam, Fenofibrate, Griseofulvin, Indomethacin, Ketoconazole, Naproxen, and Nifedipine. The protein based excipients were all based on gelatin extracted from porcine skin (Bloom=50 g); all produced by Rousselot®.

The dissolution was tested in double distilled water set to pH 7.0. The results of the dissolution test for each formulation are found displayed in FIGS. 23-32; in particular Carbamazepine (FIG. 23); Cinnarizine (FIG. 24); Darunavir (FIG. 25); Diazepam (FIG. 26), Fenofibrate (FIG. 27); Griseofulvin (FIG. 28); Indomethacin (FIG. 29); Ketoconazole (FIG. 30); Naproxen (FIG. 1), and Nifedipine (FIG. 32).

The results show an improved to greatly improved dissolution for all formulations when freeze dried in comparison with the pure (powder) form of the API. As a general conclusion, the results reveal that protein based excipients are in fact capable of enhancing the solubility of Class II API, which may further help maintain a supersaturation state over a prolonged period of time. Moreover, when taking into account that for a Class II API a direct correlation between (in-vitro) solvation and (in-vivo) bioavailability has been scientifically documented, it is expected that the solubility enhancing effects of the excipient will likely also provide bioavailability enhancing effects to the Class II API. Moreover, in case the protein excipient is made gelatin, the added benefits may yield high API concentrations in physiological media in order to achieve effective clinical performance of injectable formulations of either BCS class II or IV drugs. Indeed, since said formulation is solely comprised of non-allergic protein excipient and API, surfactants and other potentially allergic and/or toxic excipients are avoided leading to a safer product having reduced allergic potential and other side effects.

Example 15: Dissolution Profiles of (Freeze Dried) Formulations Comprising a BSA Based Excipient The development of amorphous solid dispersions for an API with BSA as excipient was tested by producing samples via freeze drying. Itraconazole served as the model API.

A formulation comprising the API and BSA containing 20% API and 80% BSA was prepared using dimethyl sulfoxide (DMSO) as solvent. Next the solution was freeze dried to produce a solid dispersion. For the freeze drying apparatus, identical conditions were applied as explained for example 13. Following the drying step, the structural properties of the formulation was again evaluated using XRD using the same parameters as set out for example 5. It is revealed that freeze drying is a suitable method to produce amorphous solid dispersions comprising itraconazole and BSA.

The results of the solubility test for the freeze dried Itraconazole:BSA solid dispersion is shown in FIG. 33. The dissolution was again tested in two pH media: the first period starting from 0 min up to 90 min represents measurement done at a pH of 1.5, and the second period running from 90 min onwards represent measurements performed at a pH of 6.8; the pH was verified during each period (pH transition is indicated by dashed line).

The results show a greatly improved dissolution for itraconazole out of the freeze dried solid dispersion in comparison with the powder form of the API.

As a general conclusion, the results reveal that protein based excipients are in fact capable of enhancing the solubility of Class II API in a gastrointestinal environment, which may further help maintain a supersaturation state over a prolonged period of time.

The invention claimed is:

1. A formulation comprising:
   a whey protein based excipient obtained from a whey protein composition or a hydrolysate thereof which comprises whey protein monomers of at least 100 amino acids in length; and
   a Class II or Class IV active pharmaceutical ingredient (API) according to the biopharmaceutics classification system;
   wherein said whey protein based excipient and said API form a homogenous and amorphous solid dispersion wherein said whey protein based excipient and said API are both completely amorphous, as verified by X-ray powder diffraction (XRD) and form a completely homogenous mixture, as verified by differential scanning calorimetry (DSC), and wherein the mass ratio (w/w) of said API to said whey protein based excipient is between at least 10% API and at most 90% whey protein based excipient (10/90) to at most 40% API and at least 60% whey protein based excipient (40/60).

2. The formulation according to claim 1, wherein the whey protein based excipient is completely not denaturized and/or retains at least part of its biological activity.

3. The formulation according to claim 1, wherein the whey protein based excipient is substantially not denaturized.

4. The formulation according to claim 3, wherein the whey protein based excipient substantially retains its biological activity.

5. The formulation according to claim 3, wherein the whey protein based excipient almost completely retains its biological activity.

6. The formulation according to claim 1, wherein the whey protein based excipient completely retains its biological activity.

7. The formulation according to claim 1, wherein the whey protein monomers are at least 250 amino acids in length.

8. The formulation according to claim 1, wherein the whey protein monomers are at least 500 amino acids in length.

9. The formulation according to claim 1, wherein the whey protein monomers are at least 700 amino acids in length.

10. The formulation according to claim 1, wherein the API exhibits poor solubility, a slow dissolution level and/or poor bioavailability.

11. The formulation according to claim 1, wherein the API is classified as poorly or not soluble, poorly or not permeable, and/or slowly dissolving according to the biopharmaceutics classification system.

12. The formulation according to claim 1, wherein the API is a class II API according to the biopharmaceutics classification system.

13. The formulation according to claim 1, wherein the API is selected from the group consisting of Flubendazole, Carbamazepine, Griseofulvin, Phenytoin, Nifedipine, Verapamil, Azithromycin, Nitrofurantoin, Iopanoic acid, Itraconazole, Ibuprofen, Indomethacin, Glibenclamide, Bicalutamide, Ezetimibe, Aceclofenac, Ketoconazole, Oxfendazole, Ritonavir, Fenofibrate, Cinnarizin, Darunavir, Diazepam, Testosterone undecanoate, and Naproxen.

14. The formulation according to claim 1, wherein said whey protein based excipient is characterized by having a particle size between 1 μm and 1 mm.

15. The formulation according to claim 1, wherein said whey protein based excipient is characterized by having a particle size between 5 μm and 50 μm.

16. The formulation according to claim 1, wherein said whey protein based excipient is characterized by having a particle size between 10 μm and 20 μm.

17. The formulation according to claim 1, wherein said formulation is provided in a solid-dosage form.

18. The formulation according to claim 17, wherein said formulation is provided in a form adapted for oral administration selected from the group consisting of a tablet, a lozenge, a pill, a capsule, and components for reconstituting as an injectable.

19. The formulation according to claim 17, wherein the solid-dosage form is a unit-dose that contains a predetermined amount of API sufficient for one regular application or use of said API, and wherein the unit-dose is suitable for unit-dose packaging.

20. The formulation according to claim 19, wherein the unit-dose packaging is a blister pack.

\* \* \* \* \*